(12) United States Patent
O'Dwyer

(10) Patent No.: US 10,799,536 B2
(45) Date of Patent: Oct. 13, 2020

(54) METHOD OF TREATING MULTIPLE MYELOMA USING NATURAL KILLER CELLS EXPRESSING A CHIMERIC ANTIGEN RECEPTOR FOR CD38

(71) Applicant: Onkimmune Limited, Donegal Town (IE)

(72) Inventor: Michael Eamon Peter O'Dwyer, Galway (IE)

(73) Assignee: ONK Therapeutics Limited, Galway (IE)

( * ) Notice: Subject to any disclaimer, the term of this patent is extended or adjusted under 35 U.S.C. 154(b) by 0 days.

(21) Appl. No.: 15/837,576

(22) Filed: Dec. 11, 2017

(65) Prior Publication Data

US 2018/0161371 A1 Jun. 14, 2018

Related U.S. Application Data

(60) Provisional application No. 62/432,302, filed on Dec. 9, 2016.

(51) Int. Cl.
| | |
|---|---|
| A61K 48/00 | (2006.01) |
| A61K 35/17 | (2015.01) |
| A61K 39/00 | (2006.01) |
| A61K 35/15 | (2015.01) |
| A61P 35/00 | (2006.01) |
| A61K 38/17 | (2006.01) |
| C07K 16/28 | (2006.01) |
| C12N 5/00 | (2006.01) |
| A61K 35/12 | (2015.01) |

(52) U.S. Cl.
CPC .............. *A61K 35/17* (2013.01); *A61K 35/15* (2013.01); *A61K 38/177* (2013.01); *A61K 39/0011* (2013.01); *A61P 35/00* (2018.01); *C07K 16/2896* (2013.01); *A61K 2035/124* (2013.01); *A61K 2039/505* (2013.01); *A61K 2039/5156* (2013.01); *A61K 2039/5158* (2013.01); *C07K 2317/56* (2013.01); *C07K 2317/565* (2013.01); *C07K 2319/70* (2013.01)

(58) Field of Classification Search
USPC ........................................ 424/93.21; 435/325
See application file for complete search history.

(56) References Cited

FOREIGN PATENT DOCUMENTS

| WO | WO 2006/099875 | * | 9/2006 |
|---|---|---|---|
| WO | WO 2006/099875 A1 | | 9/2006 |
| WO | WO 2009/077857 A2 | | 6/2009 |
| WO | WO 2011/154453 | * | 12/2011 |
| WO | WO 2011/154453 A1 | | 12/2011 |

OTHER PUBLICATIONS

Tettamanti (British J. Haematology, 2013, vol. 161, p. 389-401).*
Glienke (Frontiers in Pharm., Feb. 12, 2015, vol. 6, Article 21, p. 1-7).*
Chu (Leukemia, 2014, vol. 28, No. 4, p. 917-927).*
Rezvani (Mol. Therapy, Aug. 2017, vol. 25, No. 8, p. 1769-1781).*
Mehta (Frontiers in Immunol., Feb. 2018, vol. 9, Article 283, p. 1-12).*
Drent (Haennatologica, Feb. 8, 2016, vol. 101, No. 5, p. 616-625).*
Lokhorst (Targeting CD38 with Daratumumab Monotherapy in Multiple Myeloma. N. Engl. J. Med. 2015, 373, 1207-1219).*
Decked (SAR650984, a novel humanized CD38-targeting antibody, demonstrates potent antitumor activity in models of multiple myeloma and other CD38+ hematologic malignancies. Clin. Cancer Res. 2014, 20, 4574-4583).*
Krejcik ("Daratumumab depletes CD38+ immune regulatory cells, promotes T-cell expansion, and skews T-cell repertoire in multiple myeloma". Blood, 2016, vol. 128, p. 384-394).*
Drent ("A Rational Strategy for Reducing On-Target Off-Tumor Effects of CD38-Chimeric Antigen Receptors by Affinity Optimization". Mol. Ther., 2017, vol. 25, p. 1946-1958).*
Malavasi (Blood, "CD38 and antibody therapy: What can basic science add?", 2016, vol. 128, 36).*
Liu (Leukemia, 2018, vol. 32, p. 520-531).*
Harrer (Human Gene Therapy, 2018, vol. 29, No. 5, p. 547-558).*
Klingemann (Frontiers in Immunol., Mar. 14, 2016, vol. 7, No. 91, p. 1-7).*
Feng (Mol. Immunol., 2010, vol. 47, p. 2388-2396).*
Chu (Cancer Immunol. Res., Apr. 2015, vol. 3, No. 4, p. 333-344).*
Hu (ACTA Pharmacologica Sinica, 2018, vol. 39, p. 167-176).*
E-selectin, 2018.*
HECA452 Ab against CLA & PSGL1, 2018.*
Groth (Clin. Cancer Res., Feb. 15, 2012, vol. 18, No. 4, p. 1028-1038).*
Hudecek (Clin. Cancer Res., 2013, vol. 19, p. 3153-3164.*
Caruso (Cancer Res., 2015, vol. 75, p. 3505-3518).*
Liu (Cancer Res., 2015, vol. 75, p. 3596-3607).*
Van de Donk (Blood, Feb. 11, 2016, vol. 127, No. 6, p. 681-695).*
Kobayashi (Oct. 2014, vol. 453, No. 4, p. 798-803).*
Kim, J.H., et al., "High Cleavage Efficiency of a 2A Peptide Derived from Porcine Teschovirus-1 in Human Cell Lines, Zebrafish and Mice," *PLoS One* 6:e18566, Public Library of Science, United States (2011).
Truneh, A., et al., "Temperature-sensitive Differential Affinity of TRAIL for Its Receptors," *J. Biol. Chem.* 275:23319-23325, The American Society for Biochemistry and Molecular Biology, Inc., United States (2000).
Vink, T., et al,. "A simple, robust and highly efficient transient expression system for producing antibodies," *Methods* 65:5-10, Elsevier Inc., Netherlands (2014).
Zhao, Z., et al., "Structural design of engineered costimulation determines tumor rejection kinetics and persistence of CAR T cells," *Cancer Cell* 28:415-428, Cell Press, United States (2015).

(Continued)

*Primary Examiner* — Michael C Wilson
(74) *Attorney, Agent, or Firm* — Sterne, Kessler, Goldstein & Fox P.L.L.C.

(57) ABSTRACT

Disclosed herein are engineered natural killer cells that have been modified to express chimeric antigen receptors (CARs). The cells optionally contain other modifications that improve tumor specific cytotoxicity and homing to tumor sites. Also contemplated are methods for using the engineered natural killer cells to treat patients with cancer.

12 Claims, 26 Drawing Sheets

Specification includes a Sequence Listing.

(56) References Cited

OTHER PUBLICATIONS

Casneuf, T., et al., "Effects of daratumumab on natural killer cells and impact on clinical outcomes in relapsed or refractory multiple myeloma," *Blood Advances* 1(23):2105-2114, The American Society of Hematology, United States (2017).

Stikvoort, A., et al., "CD38 Specific Chimeric Antigen Receptor KHYG-1 Natural Killer Cells: A Potential 'Off the Shelf' Therapy for Multiple Myeloma," ASH Annual Meeting Poster Abstract and Poster, Session 653, Dec. 2, 2018, American Society of Hematology (2018).

Heo et al., "Potential therapeutic implications of IL-6/IL-6R/gp130-targeting agents in breast cancer," retrieved from www.impactjournals.com/oncotarget, Oncotarget, vol. 7, No. 13, Jan. 31, 2016, 14 pages.

Wang, Y., et al. "Fratricide of NK Cells in Daratumumab Therapy for Multiple Myeloma Overcome by Ex Vivo Expanded Autologous NK Cells," *Clin Cancer Res*.; 24(16): 4006-4017 (Aug. 2018).

Bostrom, J., et al., "Variants of the Antibody Herceptin That Interact with HER2 and VEGF at the Antigen Binding Site," Science 323: 1610-1614, American Association for the Advancement of Science, United States (Mar. 2009).

Lamdan, H., et al., "Affinity maturation and fine functional mapping of an antibody fragment against a novel neutralizing epitope on human vascular endothelial growth factor," Molecular BioSystems 9:2097-2106, RSC Publishing, United States (May 2013).

Raposo, B., et al., "Epitope-Specific antibody response is controlled by immunoglobulin Vh polymorphisms," J Exp Medicine 211(3):405-411, Rockefeller University Press, United States (Feb. 2014).

Senn, B.M., et al., "Combinatorial immunoglobulin light chain variability creates sufficient B cell diversity to mount protective antibody responses against pathogen infections,"0 Eur J. Immunol 33:950-961, Wiley VCH Verlag GmbH & Co. KgaA, Germany (Jan. 2003).

Yoshinaga, K., et al., "Ig L-Chain Shuffling for Affinity Maturation of Phage Library-derived Human Anti-human MCP-1 Antibody Blocking its Chemotactic Activity," J. Biochem 143:593-601, Japanese Biochemical Society, Japan (Jan. 2008).

Klingemann, H., "Are natural killer cells superior CAR drivers?," OncoImmunology 3:e28147, Landes Biosciences, United States (2014).

Yang, S., et al., "Development of Retargeted CD38-Specific NK-92 Cell Line for Potential Anti-Myeloma Immunotherapy," Blood 106:5104, American Society of Hematology, United States (2005).

* cited by examiner

```
                          SEQUENCE LISTING

<160> NUMBER OF SEQ ID NOS: 43

<210> SEQ ID NO 1
<211> LENGTH: 121
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Arg Phe Leu Gly Ile Ala Asn Tyr Ala Gln Lys Phe
    50                  55                  60

Gln Gly Arg Val Thr Leu Ile Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Pro Gly Glu Arg Asp Pro Asp Ala Val Asp Ile Trp Gly
            100                 105                 110

Gln Gly Thr Met Val Thr Val Ser Ser
        115                 120

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30
```

```
Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
                100                 105
```

<210> SEQ ID NO 3
<211> LENGTH: 121
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ser
 1               5                  10                  15

Ser Val Lys Val Ser Cys Lys Pro Ser Gly Gly Thr Phe Arg Ser Tyr
                 20                  25                  30

Ala Ile Ser Trp Val Arg Gln Ala Pro Gly Gln Gly Leu Glu Trp Met
             35                  40                  45

Gly Arg Ile Ile Val Phe Leu Gly Lys Val Asn Tyr Ala Gln Arg Phe
 50                  55                  60

Gln Gly Arg Val Thr Leu Thr Ala Asp Lys Ser Thr Thr Thr Ala Tyr
 65                  70                  75                  80

Met Glu Leu Ser Ser Leu Arg Ser Glu Asp Thr Ala Val Tyr Tyr Cys
                 85                  90                  95

Thr Gly Glu Pro Gly Ala Arg Asp Pro Asp Ala Phe Asp Ile Trp Gly
                100                 105                 110

Gln Gly Thr Met Val Thr Val Ser Ser
            115                 120
```

<210> SEQ ID NO 4
<211> LENGTH: 107
<212> TYPE: PRT
<213> ORGANISM: Homo sapiens

<400> SEQUENCE: 4

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Trp
                 20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gly Gly Thr Lys Val Glu Ile Lys
                100                 105
```

```
<210> SEQ ID NO 5
<211> LENGTH: 121
<212> TYPE: PRT
<213> ORGANISM: Homo sapiens

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Arg Phe Leu Gly Lys Thr Asn His Ala Gln Lys Phe
    50                  55                  60

Gln Gly Arg Val Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Pro Gly Asp Arg Asp Pro Asp Ala Val Asp Ile Trp Gly
            100                 105                 110

Gln Gly Thr Met Val Thr Val Ser Ser
        115                 120

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 7
<211> LENGTH: 122
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60
```

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120

<210> SEQ ID NO 8
<211> LENGTH: 45
<212> TYPE: DNA
<213> ORGANISM: Homo sapiens

<400> SEQUENCE: 8
ctgctgctgc atgcggcgcg cccggacatc cagatgaccc agagc            45

<210> SEQ ID NO 9
<211> LENGTH: 45
<212> TYPE: DNA
<213> ORGANISM: Homo sapiens

<400> SEQUENCE: 9
ctgctgctgc atgcggcgcg cccggacatc cagctgaccc agagc            45

<210> SEQ ID NO 10
<211> LENGTH: 45
<212> TYPE: DNA
<213> ORGANISM: Homo sapiens

<400> SEQUENCE: 10
ctgctgctgc atgcggcgcg cccggccatc cagctgaccc agagc            45

<210> SEQ ID NO 11
<211> LENGTH: 45
<212> TYPE: DNA
<213> ORGANISM: Homo sapiens

<400> SEQUENCE: 11
ctgctgctgc atgcggcgcg cccggtgatc tggatgaccc agagc            45

<210> SEQ ID NO 12
<211> LENGTH: 45
<212> TYPE: DNA
<213> ORGANISM: Homo sapiens

<400> SEQUENCE: 12
ctgctgctgc atgcggcgcg cccggagatc gtgctgaccc agagc            45

<210> SEQ ID NO 13
<211> LENGTH: 45
<212> TYPE: DNA
<213> ORGANISM: Homo sapiens

<400> SEQUENCE: 13
ctgctgctgc atgcggcgcg cccggagatc gtgatgaccc agagc            45

<210> SEQ ID NO 14
<211> LENGTH: 45
<212> TYPE: DNA
<213> ORGANISM: Homo sapiens -continued

<400> SEQUENCE: 14
ctgctgctgc atgcggcgcg cccggacatc gtgatgaccc agagc         45

<210> SEQ ID NO 15
<211> LENGTH: 51
<212> TYPE: DNA
<213> ORGANISM: Homo sapiens

<400> SEQUENCE: 15
gcggcggagg atctggggga ggcggctctc aggtgcagct ggtgcagagc g    51

<210> SEQ ID NO 16
<211> LENGTH: 52
<212> TYPE: DNA
<213> ORGANISM: Homo sapiens

<400> SEQUENCE: 16
gcggcggagg atctggggga ggcggctctg aagtgcagct ggtgcagtct gg   52

<210> SEQ ID NO 17
<211> LENGTH: 52
<212> TYPE: DNA
<213> ORGANISM: Homo sapiens

<400> SEQUENCE: 17
cagatcctcc gccgccagat ccgcctccgc ccttgatctc caccttggtg cc   52

<210> SEQ ID NO 18
<211> LENGTH: 52
<212> TYPE: DNA
<213> ORGANISM: Homo sapiens

<400> SEQUENCE: 18
cagatcctcc gccgccagat ccgcctccgc ccttgatttc cagcttggtg cc   52

<210> SEQ ID NO 19
<211> LENGTH: 52
<212> TYPE: DNA
<213> ORGANISM: Homo sapiens

<400> SEQUENCE: 19
cagatcctcc gccgccagat ccgcctccgc ccttgatgtc caccttggtg cc   52

<210> SEQ ID NO 20
<211> LENGTH: 52
<212> TYPE: DNA
<213> ORGANISM: Homo sapiens

<400> SEQUENCE: 20
cagatcctcc gccgccagat ccgcctccgc ccttgatttc cagccgggtg cc   52

<210> SEQ ID NO 21
<211> LENGTH: 60
<212> TYPE: DNA
<213> ORGANISM: Homo sapiens

<400> SEQUENCE: 21
ggggcgggtg taggcggccg cggagctggt gttgttgtgc tggacacggt gaccattgtg   60

<210> SEQ ID NO 22
<211> LENGTH: 60
<212> TYPE: DNA
<213> ORGANISM: Homo sapiens -continued

<400> SEQUENCE: 22
ggggcgggtg taggcggccg cggagctggt gttgttgtgc tagacacggt cacgagggtg    60

<210> SEQ ID NO 23
<211> LENGTH: 107
<212> TYPE: PRT
<213> ORGANISM: Homo sapiens

<400> SEQUENCE: 23

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Tyr
                85                  90                  95

Thr Phe Gly Gln Gly Thr Lys Leu Glu Ile Lys
            100                 105

<210> SEQ ID NO 24
<211> LENGTH: 23
<212> TYPE: DNA
<213> ORGANISM: Homo sapiens

<400> SEQUENCE: 24
gagtcacagg tggcatttgg cgg                                             23

<210> SEQ ID NO 25
<211> LENGTH: 23
<212> TYPE: DNA
<213> ORGANISM: Homo sapiens

<400> SEQUENCE: 25
cgaatcgcag gtggtcgcac agg                                             23

<210> SEQ ID NO 26
<211> LENGTH: 23
<212> TYPE: DNA
<213> ORGANISM: Homo sapiens

<400> SEQUENCE: 26
cactcacctt tgcagaagac agg                                             23

<210> SEQ ID NO 27
<211> LENGTH: 23
<212> TYPE: DNA
<213> ORGANISM: Homo sapiens

<400> SEQUENCE: 27
ccttgtgccg ctgaaatcca agg                                             23

<210> SEQ ID NO 28
<211> LENGTH: 107
<212> TYPE: PRT
<213> ORGANISM: Homo sapiens -continued

```
<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 29
<211> LENGTH: 10
<212> TYPE: PRT
<213> ORGANISM: Homo sapiens

<400> SEQUENCE: 29

Phe Gly Gly Thr Phe Ser Ser Tyr Ala Ile
1               5                   10

<210> SEQ ID NO 30
<211> LENGTH: 10
<212> TYPE: PRT
<213> ORGANISM: Homo sapiens

<400> SEQUENCE: 30

Ile Ile Arg Phe Leu Gly Ile Ala Asn Tyr
1               5                   10

<210> SEQ ID NO 31
<211> LENGTH: 16
<212> TYPE: PRT
<213> ORGANISM: Homo sapiens

<400> SEQUENCE: 31

Cys Ala Gly Glu Pro Gly Glu Arg Asp Pro Asp Ala Val Asp Ile Trp
1               5                   10                  15

<210> SEQ ID NO 32
<211> LENGTH: 10
<212> TYPE: PRT
<213> ORGANISM: Homo sapiens

<400> SEQUENCE: 32

Ser Gly Tyr Ser Phe Ser Asn Tyr Trp Ile
1               5                   10

<210> SEQ ID NO 33
<211> LENGTH: 11
<212> TYPE: PRT
<213> ORGANISM: Homo sapiens

<400> SEQUENCE: 33

Ile Ile Tyr Pro His Asp Ser Asp Ala Arg Tyr
1               5                   10
```

```
<210> SEQ ID NO 34
<211> LENGTH: 16
<212> TYPE: PRT
<213> ORGANISM: Homo sapiens

<400> SEQUENCE: 34

Cys Ala Arg His Val Gly Trp Gly Ser Arg Tyr Trp Tyr Phe Asp Leu
1               5                   10                  15

<210> SEQ ID NO 35
<211> LENGTH: 7
<212> TYPE: PRT
<213> ORGANISM: Homo sapiens

<400> SEQUENCE: 35

Gln Ser Ile Gly Ser Ser Leu
1               5

<210> SEQ ID NO 36
<211> LENGTH: 9
<212> TYPE: PRT
<213> ORGANISM: Homo sapiens

<400> SEQUENCE: 36

Leu Ile Lys Tyr Ala Ser Gln Ser Phe
1               5

<210> SEQ ID NO 37
<211> LENGTH: 10
<212> TYPE: PRT
<213> ORGANISM: Homo sapiens

<400> SEQUENCE: 37

His Gln Ser Ser Ser Leu Pro Tyr Thr Phe
1               5                   10

<210> SEQ ID NO 38
<211> LENGTH: 7
<212> TYPE: PRT
<213> ORGANISM: Homo sapiens

<400> SEQUENCE: 38

Gln Gly Ile Ser Asn Tyr Leu
1               5

<210> SEQ ID NO 39
<211> LENGTH: 9
<212> TYPE: PRT
<213> ORGANISM: Homo sapiens

<400> SEQUENCE: 39

Leu Ile Tyr Ala Ala Ser Ser Leu Gln
1               5

<210> SEQ ID NO 40
<211> LENGTH: 10
<212> TYPE: PRT
<213> ORGANISM: Homo sapiens

<400> SEQUENCE: 40

Gln Gln Tyr Asn Ser Tyr Pro Tyr Thr Phe
1               5                   10
```

```
<210> SEQ ID NO 41
<211> LENGTH: 164
<212> TYPE: PRT
<213> ORGANISM: Homo sapiens

<400> SEQUENCE: 41

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 42
<211> LENGTH: 255
<212> TYPE: PRT
<213> ORGANISM: Homo sapiens

<400> SEQUENCE: 42

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175
```

```
Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 43
<211> LENGTH: 220
<212> TYPE: PRT
<213> ORGANISM: Homo sapiens

<400> SEQUENCE: 43

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

METHOD OF TREATING MULTIPLE MYELOMA USING NATURAL KILLER CELLS EXPRESSING A CHIMERIC ANTIGEN RECEPTOR FOR CD38

REFERENCE TO SEQUENCE LISTING SUBMITTED ELECTRONICALLY

The content of the electronically submitted sequence listing in ASCII text format filed with the application is incorporated herein by reference in its entirety.

SUMMARY

Natural killer cells (NK Cells) are peripheral blood lymphocytes that play a role in innate immune function. NK cells express a variety of activating and inhibitory receptors that are responsible for discriminating between healthy cells, and virally infected cells or transformed (cancerous) cells. Unlike T cells, NK cells exert their cytotoxic effect on target cells in an antigen independent manner. As a result, NK cells do not require antigen priming and can display robust cytotoxicity in the absence of specific antigen.

Chimeric antigen receptors (CARs) have recently been developed to target cytotoxic T cells to particular cell types and tissues. Most CARs possess an antigen recognition domain derived from an antibody, and a transmembrane and intracellular portion derived from an immune signaling protein that is involved in T cell signal transduction, thus allowing activation of a T cell's cytotoxic function upon binding to a target antigen expressed on a target cell population.

In greater detail CARs are recombinant antigen receptors that introduce a certain antigen specificity to an immune effector cell, in the case of the current disclosure NK cells. The CAR comprises a defined polypeptide sequence expressed from an exogenous polynucleotide that has been introduced into the immune effector cell. Chimeric antigen receptors comprise a leader sequence, a targeting domain, a transmembrane domain, and one or more intracellular signaling domains. In certain embodiments, the targeting domain is derived from an antibody molecule, and comprises one or more complementarity determining regions (CDRs) from the antibody molecule that confer antigen specificity on the CAR. In certain embodiments, the targeting domain of the CAR for use in the engineered NK cells of this disclosure is a single chain variable fragment (scFv). An scFv comprises the variable chain portion of an immunoglobulin light chain, and an immunoglobulin heavy chain molecule separated by a flexible linker polypeptide. The flexible polypeptide linker allows the heavy and light chains to associate with one another and reconstitute an immunoglobulin antigen binding domain.

Described herein are pharmaceutical compositions comprising NK cells, both primary cells and cell lines that have been engineered with at least one chimeric antigen receptor. These compositions are useful in the treatment of cancer, both solid tumors and hematological (blood) cancers. Also described are methods of using and making the same. The pharmaceutical compositions described herein comprise primary NK cells and NK cell lines, such as KHYG-1, that express chimeric antigen receptors. In certain embodiments, the CARs target cancer associated antigens. For example, the cancer associated antigen can comprise CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In certain specific embodiments, the chimeric antigen receptor can be specific for CD38. Optionally, the NK cells comprise at least one other modification that results in increased cytotoxic activity of the NK cell. In certain embodiments, the modification comprises deletion or reduced expression of a checkpoint inhibitor, or increased expression of TRAIL or a TRAIL variant with higher affinity for a TRAIL receptor such as DR4 or DR5. Advantageously, the engineered NK cells of the current disclosure display increased expression of E-selectin ligands, and/or reduced expression of TRAIL receptors such as DR4, DR5, or both. These engineered NK cells can be used to treat individuals diagnosed with cancer by adoptive transfer via an intravenous route. These NK cells can be engineered in a variety of methods known in the art including by viral transduction or electroporation of polynucleotides/vectors that express CARs and/or molecules that activate an NK cell's cytotoxic activity; such as variant TNF-related apoptosis-inducing ligand (TRAIL) protein; or by vectors that delete or reduce expression of inhibitory receptors through an siRNA, shRNA or a CRISPR/Cas9 targeting mechanism. The NK cells can be primary cells or established NK cell lines that retain some of the function and characteristics of primary NK cells. In a specific embodiment, the engineered NK cell line is an KHYG-1 cell, or a KHYG-1 like cell that possess distinct qualities from common cell like NK-92, such as high E-selectin ligand expression, and low expression of TARIL receptors DR4 and DR5. The adoptive transfer can be with autologous (syngeneic) or heterologous (allogeneic) NK cells.

In a certain aspect, disclosed herein is a pharmaceutical composition comprising an engineered natural killer cell, wherein the engineered natural killer cell exhibits a high level of cell-surface expression of E-selectin ligand, wherein the engineered natural killer cell comprises a chimeric antigen receptor (CAR). In a certain embodiment, the engineered natural killer cell comprises a plurality of engineered natural killer cells that are greater than 25% positive for an antigen bound by the HECA-452 antibody. In a certain embodiment, the engineered natural killer cell exhibits a low level of cell-surface expression of a TRAIL receptor, wherein the TRAIL receptor comprises TNFRSF10A (DR4) or TNFRSF10B (DR5). In a certain embodiment, the engineered natural killer cell comprises a primary engineered natural killer cell. In a certain embodiment, the engineered natural killer cell comprises a transformed engineered natural killer cell line. In a certain embodiment, the transformed engineered natural killer cell line is the NK-92 cell line or the KHYG-1 cell line. In a certain embodiment, the transformed engineered natural killer cell line is the KHYG-1 cell line. In a certain embodiment, the CAR specifically binds a cancer associated antigen. In a certain embodiment, the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In certain embodiments, the cancer associated antigen comprises a blood cancer associated antigen. In certain embodiments, the blood cancer associated antigen comprises CD38, CD319/SLAMF-7, TNFRSF17/BCMA, SYND1/CD138, CD229, CD47, CD123/IL3-RA, CD19, CD20, CD22, or CLL-1. In certain embodiments, the blood cancer associated antigen comprises CD38. In certain embodiments, the CAR comprises a targeting domain amino acid sequence that is at least 80% identical to that set forth in any one of SEQ ID NOs: 1-6. In certain embodiments, the CAR comprises a targeting domain amino acid sequence that is at least 90% identical to that set forth in any one of SEQ ID NOs: 1-6. In certain embodiments, the CAR comprises a targeting domain amino acid sequence that is at least 95% identical to that set forth in any one of SEQ ID NOs: 1-6. In certain embodiments, the CAR comprises a targeting domain amino acid sequence that is at least 98% identical to that set forth in any one of SEQ ID NOs: 1-6. In certain embodiments, the CAR comprises a targeting domain amino acid sequence that is identical to that set forth in any one of SEQ ID NOs: 1-6. In certain embodiments, the CAR comprises a targeting domain amino acid sequence that is at least 90% identical to that set forth in SEQ ID NOs: 1 and 2. In certain embodiments, the CAR comprises a targeting domain amino acid sequence that is at least 95% identical to that set forth in SEQ ID NOs: 1 and 2. In certain embodiments, wherein the CAR comprises a targeting domain amino acid sequence that is at least 98% identical to that set forth in SEQ ID NOs: 1 and 2. In certain embodiments, the CAR comprises a targeting domain amino acid sequence that is identical to that set forth in SEQ ID NOs: 1 and 2. In certain embodiments, the CAR comprises a targeting domain amino acid sequence that is at least 90% identical to that set forth in SEQ ID NOs: 3 and 4. In a certain embodiment, the CAR comprises a targeting domain amino acid sequence that is at least 95% identical to that set forth in SEQ ID NOs: 3 and 4. In certain embodiments, the CAR comprises a targeting domain amino acid sequence that is at least 98% identical to that set forth in SEQ ID NOs: 3 and 4. In certain embodiments, the CAR comprises a targeting domain amino acid sequence that is identical to that set forth in SEQ ID NOs: 3 and 4. In certain embodiments, the CAR comprises a targeting domain amino acid sequence that is at least 90% identical to that set forth in SEQ ID NOs: 5 and 6. In certain embodiments, the CAR comprises a targeting domain amino acid sequence that is at least 95% identical to that set forth in SEQ ID NOs: 5 and 6. In certain embodiments, the CAR comprises a targeting domain amino acid sequence that is at least 98% identical to that set forth in SEQ ID NOs: 5 and 6. In certain embodiments, the CAR comprises a targeting domain amino acid sequence that is identical to that set forth in SEQ ID NOs: 5 and 6. In certain embodiments, the CAR comprises a human CD8 alpha polypeptide. In certain embodiments, the CAR comprises a DAP10, DAP12, 2B4 (CD244), or human 4-1BB polypeptide. In certain embodiments, the CAR comprises a human 4-1BB polypeptide. In certain embodiments, the CAR comprises a human CD3 zeta polypeptide. In certain embodiments, the CAR comprises a targeting domain that is derived from an antibody that exhibits a lower affinity for CD38 than Daratumumab. In an additional aspect, the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In an additional aspect, the engineered natural killer cell further comprises a mutant TNF-related apoptosis-inducing ligand (TRAIL) polypeptide, wherein the mutant TRAIL polypeptide induces increased signaling or possesses increased binding affinity to a TRAIL ligand. In certain embodiments, the TRAIL ligand comprises TNFRSF10A (DR4) or TNFRSF10B (DR5). In certain embodiments, the mutant TRAIL polypeptide comprises a D269H/E195R mutation of human TRAIL. In certain embodiments, the mutant TRAIL polypeptide comprises a G131R/N199R/K201H mutation of human TRAIL. In certain embodiments, the CAR or the mutant TRAIL polypeptide is integrated into the genome of the engineered natural killer cell. In certain embodiments, the engineered natural killer cell further comprises a deletion or reduction in activity of a checkpoint inhibitory receptor. In certain embodiments, the checkpoint inhibitory receptor comprises CD85d, CD85j, CD96, CD152, CD159a, CD223, CD279, CD328, SIGLEC9, TIGIT or TIM-3. In certain embodiments, the checkpoint inhibitory receptor comprises CD96, CD152, or CD328. In certain embodiments, the checkpoint inhibitory receptor comprises CD96. In certain embodiments, the checkpoint inhibitory receptor comprises CD152 In certain embodiments, the checkpoint inhibitory receptor comprises CD328. In certain embodiments, the checkpoint inhibitory receptor is deleted in whole or in part from the engineered natural killer cell genome, or is disrupted by insertion or deletion of one or more nucleotides at the chromosomal level. In certain embodiments, the engineered natural killer cell comprises an siRNA that targets a checkpoint inhibitory receptor. In certain embodiments, the pharmaceutical composition further comprises a pharmaceutically acceptable carrier, stabilizer, or excipient. In certain embodiments, the pharmaceutical composition is formulated for intraperitoneal administration. In certain embodiments, the pharmaceutical composition is formulated for intraperitoneal administration. In certain embodiments, the pharmaceutical composition is for use in treating cancer. In certain embodiments, the cancer comprises a leukemia, a lymphoma, or a myeloma. In certain embodiments, the cancer comprises multiple myeloma.

In a certain aspect, disclosed herein is a method of treating a subject with cancer comprising administering to the subject a pharmaceutical composition comprising an engineered natural killer cell, wherein the engineered natural killer cell exhibits a high level of cell-surface expression of E-selectin ligand, wherein the engineered natural killer cell comprises a chimeric antigen receptor (CAR). In a certain embodiment, the engineered natural killer cell comprises a plurality of engineered natural killer cells that are greater than 25% positive for an antigen bound by the HECA-452 antibody. In a certain embodiment, the engineered natural killer cell exhibits a low level of cell-surface expression of a TRAIL receptor, wherein the TRAIL receptor comprises TNFRSF10A (DR4) or TNFRSF10B (DR5). In a certain embodiment, the engineered natural killer cell comprises a primary engineered natural killer cell. In a certain embodiment, the engineered natural killer cell comprises a transformed engineered natural killer cell line. In a certain embodiment, the transformed engineered natural killer cell line is the NK-92 cell line or the KHYG-1 cell line. In a certain embodiment, the transformed engineered natural killer cell line is the KHYG-1 cell line. In a certain embodiment, the CAR specifically binds a cancer associated antigen. In a certain embodiment, the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In certain embodiments, the cancer associated antigen comprises a blood cancer associated antigen. In certain embodiments, the blood cancer associated antigen comprises CD38, CD319/SLAMF-7, TNFRSF17/BCMA, SYND1/CD138, CD229, CD47, CD123/IL3-RA, CD19, CD20, CD22, or CLL. In certain embodiments, the blood cancer associated antigen comprises CD38. In certain embodiments, the CAR comprises a targeting domain amino acid sequence that is at least 80% identical to that set forth in any one of SEQ ID NOs: 1-6. In certain embodiments, the CAR comprises a targeting domain amino acid sequence that is at least 90% identical to that set forth in any one of SEQ ID NOs: 1-6. In certain embodiments, the CAR comprises a targeting domain amino acid sequence that is at least 95% identical to that set forth in any one of SEQ ID NOs: 1-6. In certain embodiments, the CAR comprises a targeting domain amino acid sequence that is at least 98% identical to that set forth in any one of SEQ ID NOs: 1-6. In certain embodiments, the CAR comprises a targeting domain amino acid sequence that is identical to that set forth in any one of SEQ ID NOs: 1-6. In certain embodiments, the CAR comprises a targeting domain amino acid sequence that is at least 90% identical to that set forth in SEQ ID NOs: 1 and 2. In certain embodiments, the CAR comprises a targeting domain amino acid sequence that is at least 95% identical to that set forth in SEQ ID NOs: 1 and 2. In certain embodiments, wherein the CAR comprises a targeting domain amino acid sequence that is at least 98% identical to that set forth in SEQ ID NOs: 1 and 2. In certain embodiments, the CAR comprises a targeting domain amino acid sequence that is identical to that set forth in SEQ ID NOs: 1 and 2. In certain embodiments, the CAR comprises a targeting domain amino acid sequence that is at least 90% identical to that set forth in SEQ ID NOs: 3 and 4. In a certain embodiment, the CAR comprises a targeting domain amino acid sequence that is at least 95% identical to that set forth in SEQ ID NOs: 3 and 4. In certain embodiments, the CAR comprises a targeting domain amino acid sequence that is at least 98% identical to that set forth in SEQ ID NOs: 3 and 4. In certain embodiments, the CAR comprises a targeting domain amino acid sequence that is identical to that set forth in SEQ ID NOs: 3 and 4. In certain embodiments, the CAR comprises a targeting domain amino acid sequence that is at least 90% identical to that set forth in SEQ ID NOs: 5 and 6. In certain embodiments, the CAR comprises a targeting domain amino acid sequence that is at least 95% identical to that set forth in SEQ ID NOs: 5 and 6. In certain embodiments, the CAR comprises a targeting domain amino acid sequence that is at least 98% identical to that set forth in SEQ ID NOs: 5 and 6. In certain embodiments, the CAR comprises a targeting domain amino acid sequence that is identical to that set forth in SEQ ID NOs: 5 and 6. In certain embodiments, the CAR comprises a CD8 alpha polypeptide. In certain embodiments, the CAR comprises a DAP10, DAP12, 2B4 (CD244), or human 4-1BB polypeptide. In certain embodiments, the CAR comprises a human 4-1BB polypeptide. In certain embodiments, the CAR comprises a human CD3 zeta polypeptide. In certain embodiments, the CAR comprises a targeting domain that is derived from an antibody that exhibits a lower affinity for CD38 than Daratumumab. In an additional aspect, the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In an additional aspect, the engineered natural killer cell further comprises a mutant TNF-related apoptosis-inducing ligand (TRAIL) polypeptide, wherein the mutant TRAIL polypeptide induces increased signaling or possesses increased binding affinity to a TRAIL ligand. In certain embodiments, the TRAIL ligand comprises TNFRSF10A (DR4) or TNFRSF10B (DR5). In certain embodiments, the mutant TRAIL polypeptide comprises a D269H/E195R mutation of human TRAIL. In certain embodiments, the mutant TRAIL polypeptide comprises a G131R/N199R/K201H mutation of human TRAIL. In certain embodiments, the CAR or the mutant TRAIL polypeptide is integrated into the genome of the engineered natural killer cell. In certain embodiments, the engineered natural killer cell further comprises a deletion or reduction in activity of a checkpoint inhibitory receptor. In certain embodiments, the checkpoint inhibitory receptor comprises CD85d, CD85j, CD96, CD152, CD159a, CD223, CD279, CD328, SIGLEC9, TIGIT or TIM-3. In certain embodiments, the checkpoint inhibitory receptor comprises CD96, CD152, or CD328. In certain embodiments, the checkpoint inhibitory receptor comprises CD96. In certain embodiments, the checkpoint inhibitory receptor comprises CD152 In certain embodiments, the checkpoint inhibitory receptor comprises CD328. In certain embodiments, the checkpoint inhibitory receptor is deleted in whole or in part from the engineered natural killer cell genome, or is disrupted by insertion or deletion of one or more nucleotides at the chromosomal level. In certain embodiments, the engineered natural killer cell comprises an siRNA that targets a checkpoint inhibitory receptor. In certain embodiments, the checkpoint inhibitory receptor is deleted from the engineered natural killer cell genome. In certain embodiments, the pharmaceutical composition comprises a pharmaceutically acceptable carrier, stabilizer, or excipient. In certain embodiments, the pharmaceutical composition is formulated for intravenous administration. In certain embodiments, the pharmaceutical composition is formulated for intraperitoneal administration. In certain embodiments, the cancer comprises a leukemia, a lymphoma, or a myeloma. In certain embodiments, the cancer comprises multiple myeloma. In certain embodiments, the pharmaceutical composition is administered before during or after administration of a proteasome inhibitor. In certain embodiments, the pharmaceutical composition is administered before, during, or after a low-dose metronomic cyclophosphamide treatment regimen.

In a certain aspect, described herein, is a method of making a pharmaceutical composition comprising an engineered natural killer cell, wherein the engineered natural killer cell exhibits a high level of cell-surface expression of E-selectin ligand, wherein the engineered natural killer cell comprises a chimeric antigen receptor (CAR), wherein the method comprises incubating a natural killer cell with a polynucleotide that encodes the CAR. In certain embodiments, the polynucleotide comprises a viral vector. In certain embodiments, the viral vector is a lentivirus. In certain embodiments, the viral vector is a retrovirus. In certain embodiments, the polynucleotide comprises mRNA. In certain embodiments, the polynucleotide is integrated into the genome of the engineered natural killer cell. In certain embodiments, the engineered natural killer cell is treated with a chemical to increase fucosylation of the engineered natural killer cell. In certain embodiments, the engineered natural killer cell comprises a plurality of engineered natural killer cells that are greater than 25% positive for an antigen bound by the HECA-452 antibody. In certain embodiments, the engineered natural killer cell exhibits a low level of cell-surface expression of a TRAIL receptor, wherein the TRAIL receptor comprises TNFRSF10A (DR4) or TNFRSF10B (DR5). In certain embodiments, the engineered natural killer cell comprises a primary natural killer cell. In certain embodiments, the engineered natural killer cell comprises a transformed natural killer cell line. In certain embodiments, the transformed natural killer cell line is the NK-92 cell line or the KHYG-1 cell line. In certain embodiments, the transformed natural killer cell line is the KHYG-1 cell line. In certain embodiments, the CAR specifically binds a cancer associated antigen. In certain embodiments, the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In certain embodiments, the cancer associated antigen comprises a blood cancer associated antigen. In certain embodiments, the blood cancer associated antigen comprises CD38, CD319/SLAMF-7, TNFRSF17/BCMA, SYND1/CD138, CD229, CD47, CD123/IL3-RA, CD19, CD20, CD22, or CLL-1. In certain embodiments, the blood cancer associated antigen comprises CD38. In certain embodiments, the CAR comprises a targeting domain amino acid sequence that is at least 80% identical to that set forth in any one of SEQ ID NOs: 1-6. In certain embodiments, the CAR comprises a targeting domain amino acid sequence that is at least 90% identical to that set forth in any one of SEQ ID NOs: 1-6. In certain embodiments, the CAR comprises a targeting domain amino acid sequence that is at least 95% identical to that set forth in any one of SEQ ID NOs: 1-6. In certain embodiments, the CAR comprises a targeting domain amino acid sequence that is at least 98% identical to that set forth in any one of SEQ ID NOs: 1-6. In certain embodiments, the CAR comprises a targeting domain amino acid sequence that is identical to that set forth in any one of SEQ ID NOs: 1-6. In certain embodiments, the CAR comprises a targeting domain amino acid sequence that is at least 90% identical to that set forth in SEQ ID NOs: 1 and 2. In certain embodiments, the CAR comprises a targeting domain amino acid sequence that is at least 95% identical to that set forth in SEQ ID NOs: 1 and 2. In certain embodiments, wherein the CAR comprises a targeting domain amino acid sequence that is at least 98% identical to that set forth in SEQ ID NOs: 1 and 2. In certain embodiments, the CAR comprises a targeting domain amino acid sequence that is identical to that set forth in SEQ ID NOs: 1 and 2. In certain embodiments, the CAR comprises a targeting domain amino acid sequence that is at least 90% identical to that set forth in SEQ ID NOs: 3 and 4. In certain embodiments, the CAR comprises a targeting domain amino acid sequence that is at least 95% identical to that set forth in SEQ ID NOs: 3 and 4. In certain embodiments, the CAR comprises a targeting domain amino acid sequence that is at least 98% identical to that set forth in SEQ ID NOs: 3 and 4. In certain embodiments, the CAR comprises a targeting domain amino acid sequence that is identical to that set forth in SEQ ID NOs: 3 and 4. In certain embodiments, the CAR comprises a targeting domain amino acid sequence that is at least 90% identical to that set forth in SEQ ID NOs: 5 and 6. In certain embodiments, the CAR comprises a targeting domain amino acid sequence that is at least 95% identical to that set forth in SEQ ID NOs: 5 and 6. In certain embodiments, the CAR comprises a targeting domain amino acid sequence that is at least 98% identical to that set forth in SEQ ID NOs: 5 and 6. In certain embodiments, the CAR comprises a targeting domain amino acid sequence that is identical to that set forth in SEQ ID NOs: 5 and 6. In certain embodiments, the CAR comprises a human CD8 alpha polypeptide. In certain embodiments, the CAR comprises a DAP10, DAP12, 2B4 (CD244), or human 4-1BB polypeptide. In certain embodiments, the CAR comprises a human 4-1BB polypeptide. In certain embodiments, the CAR comprises a human CD3 zeta polypeptide. In certain embodiments, the CAR comprises a targeting domain that is derived from an antibody that exhibits a lower affinity for CD38 than Daratumumab. In an additional aspect, the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In an additional aspect, the engineered natural killer cell further comprises a mutant TNF-related apoptosis-inducing ligand (TRAIL) polypeptide, wherein the mutant TRAIL polypeptide induces increased signaling or possesses increased binding affinity to a TRAIL ligand. In certain embodiments, the TRAIL ligand comprises TNFRSF10A (DR4) or TNFRSF10B (DR5). In certain embodiments, the mutant TRAIL polypeptide comprises a D269H/E195R mutation of human TRAIL. In certain embodiments, the mutant TRAIL polypeptide comprises a G131R/N199R/K201H mutation of human TRAIL. In certain embodiments, the CAR or the mutant TRAIL polynucleotide is integrated into the genome of the engineered natural killer cell. In certain embodiments, the method further comprises incubating the engineered natural killer cell with a polynucleotide that deletes or reduces activity of a checkpoint inhibitory receptor. In certain embodiments, the checkpoint inhibitory receptor comprises CD85d, CD85j, CD96, CD152, CD159a, CD223, CD279, CD328, SIGLEC9, TIGIT or TIM-3. In certain embodiments, the checkpoint inhibitory receptor comprises CD96, CD152, or CD328. In certain embodiments, the checkpoint inhibitory receptor comprises CD96. In certain embodiments, the checkpoint inhibitory receptor comprises CD152 In certain embodiments, the checkpoint inhibitory receptor comprises CD328. In certain embodiments, the checkpoint inhibitory receptor is deleted in whole or in part from the engineered natural killer cell genome, or is disrupted by insertion or deletion of one or more nucleotides at the chromosomal level. In certain embodiments, the engineered natural killer cell comprises an siRNA that targets a checkpoint inhibitory receptor. In certain embodiments, the method further comprises admixing the engineered natural killer cell with a pharmaceutically acceptable carrier, stabilizer, or excipient.

In a certain aspect, described herein, is a pharmaceutical composition comprising an engineered natural killer cell, wherein the engineered natural killer cell exhibits a high level of expression of the FUT6 or FUT7 protein, wherein the engineered natural killer cell comprises a chimeric antigen receptor (CAR). In certain embodiments, the engineered natural killer cell comprises an exogenous polynucleotide encoding the FUT6 or FUT7 protein. In certain embodiments, the CAR specifically binds a cancer associated antigen. In certain embodiments, the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In certain embodiments, the cancer associated antigen comprises a blood cancer associated antigen. In certain embodiments, the blood cancer associated antigen comprises CD38, CD319/SLAMF-7, TNFRSF17/BCMA, SYND1/CD138, CD229, CD47, CD123/IL3-RA, CD19, CD20, CD22, or CLL-1. In certain embodiments, the blood cancer associated antigen comprises CD38. In certain embodiments, the CAR comprises a targeting domain amino acid sequence that is at least 80% identical to that set forth in any one of SEQ ID NOs: 1-6. In certain embodiments, the CAR comprises a targeting domain amino acid sequence that is at least 90% identical to that set forth in any one of SEQ ID NOs: 1-6. In certain embodiments, the CAR comprises a targeting domain amino acid sequence that is at least 95% identical to that set forth in any one of SEQ ID NOs: 1-6. In certain embodiments, the CAR comprises a targeting domain amino acid sequence that is at least 98% identical to that set forth in any one of SEQ ID NOs: 1-6. In certain embodiments, the CAR comprises a targeting domain amino acid sequence that is identical to that set forth in any one of SEQ ID NOs: 1-6. In certain embodiments, the CAR comprises a targeting domain amino acid sequence that is at least 90% identical to that set forth in SEQ ID NOs: 1 and 2. In certain embodiments, the CAR comprises a targeting domain amino acid sequence that is at least 95% identical to that set forth in SEQ ID NOs: 1 and 2. In certain embodiments, wherein the CAR comprises a targeting domain amino acid sequence that is at least 98% identical to that set forth in SEQ ID NOs: 1 and 2. In certain embodiments, the CAR comprises a targeting domain amino acid sequence that is identical to that set forth in SEQ ID NOs: 1 and 2. In certain embodiments, the CAR comprises a targeting domain amino acid sequence that is at least 90% identical to that set forth in SEQ ID NOs: 3 and 4. In certain embodiments, the CAR comprises a targeting domain amino acid sequence that is at least 95% identical to that set forth in SEQ ID NOs: 3 and 4. In certain embodiments, the CAR comprises a targeting domain amino acid sequence that is at least 98% identical to that set forth in SEQ ID NOs: 3 and 4. In certain embodiments, the CAR comprises a targeting domain amino acid sequence that is identical to that set forth in SEQ ID NOs: 3 and 4. In certain embodiments, the CAR comprises a targeting domain amino acid sequence that is at least 90% identical to that set forth in SEQ ID NOs: 5 and 6. In certain embodiments, the CAR comprises a targeting domain amino acid sequence that is at least 95% identical to that set forth in SEQ ID NOs: 5 and 6. In certain embodiments, the CAR comprises a targeting domain amino acid sequence that is at least 98% identical to that set forth in SEQ ID NOs: 5 and 6. In certain embodiments, the CAR comprises a targeting domain amino acid sequence that is identical to that set forth in SEQ ID NOs: 5 and 6. In certain embodiments, the CAR comprises a human CD8 alpha polypeptide. In certain embodiments, the CAR comprises an intracellular domain derived from DAP10, DAP12, 2B4 (CD244), or the human 4-1BB polypeptide. In certain embodiments, the CAR comprises an intracellular domain derived from the human 4-1BB polypeptide. In certain embodiments, the CAR comprises an intracellular domain derived from human CD3 zeta polypeptide. In certain embodiments, the CAR comprises a targeting domain that is derived from an antibody that exhibits a lower affinity for CD38 than Daratumumab. In an additional aspect, the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

In a certain aspect, disclosed herein, is a method of treating a subject with cancer comprising administering to the subject a pharmaceutical composition comprising an engineered natural killer cell, wherein the engineered natural killer cell exhibits a high level of expression of the FUT6 or FUT7 protein, wherein the engineered natural killer cell comprises a chimeric antigen receptor (CAR). In certain embodiments, the engineered natural killer cell comprises an exogenous polynucleotide encoding the FUT6 or FUT7 protein. In certain embodiments, the CAR specifically binds a cancer associated antigen. In certain embodiments, the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K. In certain embodiments, the cancer associated antigen comprises a blood cancer associated antigen. In certain embodiments, the blood cancer associated antigen comprises CD38, CD319/SLAMF-7, TNFRSF17/BCMA, SYND1/CD138, CD229, CD47, CD123/IL3-RA, CD19, CD20, CD22, or CLL-1. In certain embodiments, the blood cancer associated antigen comprises CD38. In certain embodiments, the CAR comprises a targeting domain amino acid sequence that is at least 80% identical to that set forth in any one of SEQ ID NOs: 1-6. In certain embodiments, the CAR comprises a targeting domain amino acid sequence that is at least 90% identical to that set forth in any one of SEQ ID NOs: 1-6. In certain embodiments, the CAR comprises a targeting domain amino acid sequence that is at least 95% identical to that set forth in any one of SEQ ID NOs: 1-6. In certain embodiments, the CAR comprises a targeting domain amino acid sequence that is at least 98% identical to that set forth in any one of SEQ ID NOs: 1-6. In certain embodiments, the CAR comprises a targeting domain amino acid sequence that is identical to that set forth in any one of SEQ ID NOs: 1-6. In certain embodiments, the CAR comprises a targeting domain amino acid sequence that is at least 90% identical to that set forth in SEQ ID NOs: 1 and 2. In certain embodiments, the CAR comprises a targeting domain amino acid sequence that is at least 95% identical to that set forth in SEQ ID NOs: 1 and 2. In certain embodiments, wherein the CAR comprises a targeting domain amino acid sequence that is at least 98% identical to that set forth in SEQ ID NOs: 1 and 2. In certain embodiments, the CAR comprises a targeting domain amino acid sequence that is identical to that set forth in SEQ ID NOs: 1 and 2. In certain embodiments, the CAR comprises a targeting domain amino acid sequence that is at least 90% identical to that set forth in SEQ ID NOs: 3 and 4. In certain embodiments, the CAR comprises a targeting domain amino acid sequence that is at least 95% identical to that set forth in SEQ ID NOs: 3 and 4. In certain embodiments, the CAR comprises a targeting domain amino acid sequence that is at least 98% identical to that set forth in SEQ ID NOs: 3 and 4. In certain embodiments, the CAR comprises a targeting domain amino acid sequence that is identical to that set forth in SEQ ID NOs: 3 and 4. In certain embodiments, the CAR comprises a targeting domain amino acid sequence that is at least 90% identical to that set forth in SEQ ID NOs: 5 and 6. In certain embodiments, the CAR comprises a targeting domain amino acid sequence that is at least 95% identical to that set forth in SEQ ID NOs: 5 and 6. In certain embodiments, the CAR comprises a targeting domain amino acid sequence that is at least 98% identical to that set forth in SEQ ID NOs: 5 and 6. In certain embodiments, the CAR comprises a targeting domain amino acid sequence that is identical to that set forth in SEQ ID NOs: 5 and 6. In certain embodiments, the CAR comprises a CD8 alpha polypeptide. In certain embodiments, the CAR comprises a DAP10, DAP12, 2B4 (CD244), or human 4-1BB polypeptide. In certain embodiments, the CAR comprises a human 4-1BB polypeptide. In certain embodiments, the CAR comprises a human CD3 zeta polypeptide. In certain embodiments, the CAR comprises a targeting domain that is derived from an antibody that exhibits a lower affinity for CD38 than Daratumumab. In an additional aspect, the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEUSGC, NeuGcGM3, GD2, CLL-1, or HERV-K.

Preferably, the CD38-CAR-expressing NK cells have a decreased affinity for normal (non-malignant) cells expressing CD38, compared with their affinity for CD38-expressing cancer cells. This can result, for example, because the cancer cells express higher levels of CD38 than the normal cells and/or because the CD38-CARs have increased affinity for the specific form of CD38 expressed on the cancer cells and/or decreased affinity for the specific form of CD38 expressed on the normal cells. It is preferred that the increase in affinity of the CD38-CAR-expressing NK cell for the cancer cell is at least 10%, at least 20%, at least 50%, more preferably at least 100%, compared with the affinity of the CD38-CAR-expressing NK cell for the normal cell. It is preferred that the decrease in affinity of the CD38-CAR-expressing NK cell for the normal cell is at least 10%, at least 20%, at least 50%, more preferably at least 100%, compared with the affinity of the CD38-CAR-expressing NK cell for the cancer cell. It is preferred that the increase in affinity of the CD38-CAR-expressing NK cell for the cancer cell is at least 1.5-fold, at least 2-fold, at least 5-fold, at least 10-fold, at least 100-fold, more preferably at least 1000-fold greater than the affinity of the CD38-CAR-expressing NK cell for the normal cell. It is preferred that the decrease in affinity of the CD38-CAR-expressing NK cell for the normal cell is at least 1.5-fold, at least 2-fold, at least 5-fold, at least 10-fold, at least 100-fold, more preferably at least 1000-fold smaller than the affinity of the CD38-CAR-expressing NK cell for the cancer cell. Preferably, CD38-CAR-expressing NK cells have low affinity for normal CD38-expressing cells, wherein 'low affinity' is defined as having an affinity high enough to effectively mount a cytotoxic response against target cancer cells with increased expression (relative to normal cells) of CD38 (e.g. multiple myeloma cells), but low enough to avoid mounting a cytotoxic response against normal CD38-expressing cells.

In a certain aspect, disclosed herein, is a method of making a pharmaceutical composition comprising an engineered natural killer cell, wherein the engineered natural killer cell exhibits a high level of expression of the FUT6 or FUT7 protein, wherein the engineered natural killer cell comprises a chimeric antigen receptor (CAR), wherein the method comprises incubating a natural killer cell with a polynucleotide that encodes the CAR. In certain embodiments, the engineered natural killer cell comprises an exogenous polynucleotide encoding the FUT6 or FUT7 protein. In certain embodiments, the CAR specifically binds a cancer associated antigen. In certain embodiments, the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEUSGC, NeuGcGM3, GD2, CLL-1, or HERV-K. In certain embodiments, the cancer associated antigen comprises a blood cancer associated antigen. In certain embodiments, the blood cancer associated antigen comprises CD38, CD319/SLAMF-7, TNFRSF17/BCMA, SYND1/CD138, CD229, CD47, CD123/IL3-RA, CD19, CD20, CD22, or CLL-1. In certain embodiments, the blood cancer associated antigen comprises CD38. In certain embodiments, the CAR comprises a targeting domain amino acid sequence that is at least 80% identical to that set forth in any one of SEQ ID NOs: 1-6. In certain embodiments, the CAR comprises a targeting domain amino acid sequence that is at least 90% identical to that set forth in any one of SEQ ID NOs: 1-6. In certain embodiments, the CAR comprises a targeting domain amino acid sequence that is at least 95% identical to that set forth in any one of SEQ ID NOs: 1-6. In certain embodiments, the CAR comprises a targeting domain amino acid sequence that is at least 98% identical to that set forth in any one of SEQ ID NOs: 1-6. In certain embodiments, the CAR comprises a targeting domain amino acid sequence that is identical to that set forth in any one of SEQ ID NOs: 1-6. In certain embodiments, the CAR comprises a targeting domain amino acid sequence that is at least 90% identical to that set forth in SEQ ID NOs: 1 and 2. In certain embodiments, the CAR comprises a targeting domain amino acid sequence that is at least 95% identical to that set forth in SEQ ID NOs: 1 and 2. In certain embodiments, wherein the CAR comprises a targeting domain amino acid sequence that is at least 98% identical to that set forth in SEQ ID NOs: 1 and 2. In certain embodiments, the CAR comprises a targeting domain amino acid sequence that is identical to that set forth in SEQ ID NOs: 1 and 2. In certain embodiments, the CAR comprises a targeting domain amino acid sequence that is at least 90% identical to that set forth in SEQ ID NOs: 3 and 4. In certain embodiments, the CAR comprises a targeting domain amino acid sequence that is at least 95% identical to that set forth in SEQ ID NOs: 3 and 4. In certain embodiments, the CAR comprises a targeting domain amino acid sequence that is at least 98% identical to that set forth in SEQ ID NOs: 3 and 4. In certain embodiments, the CAR comprises a targeting domain amino acid sequence that is identical to that set forth in SEQ ID NOs: 3 and 4. In certain embodiments, the CAR comprises a targeting domain amino acid sequence that is at least 90% identical to that set forth in SEQ ID NOs: 5 and 6. In certain embodiments, the CAR comprises a targeting domain amino acid sequence that is at least 95% identical to that set forth in SEQ ID NOs: 5 and 6. In certain embodiments, the CAR comprises a targeting domain amino acid sequence that is at least 98% identical to that set forth in SEQ ID NOs: 5 and 6. In certain embodiments, the CAR comprises a targeting domain amino acid sequence that is identical to that set forth in SEQ ID NOs: 5 and 6. In certain embodiments, the CAR comprises a human CD8 alpha polypeptide. In certain embodiments, the CAR comprises a DAP10, DAP12, 2B4 (CD244), or human 4-1BB polypeptide. In certain embodiments, the CAR comprises a human 4-1BB polypeptide. In certain embodiments, the CAR comprises a human CD3 zeta polypeptide. In certain embodiments, the CAR comprises a targeting domain that is derived from an antibody that exhibits a lower affinity for CD38 than Daratumumab. In an additional aspect, the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEUSGC, NeuGcGM3, GD2, CLL-1, or HERV-K.

DETAILED DESCRIPTION

Certain Definitions

Figure 1A:
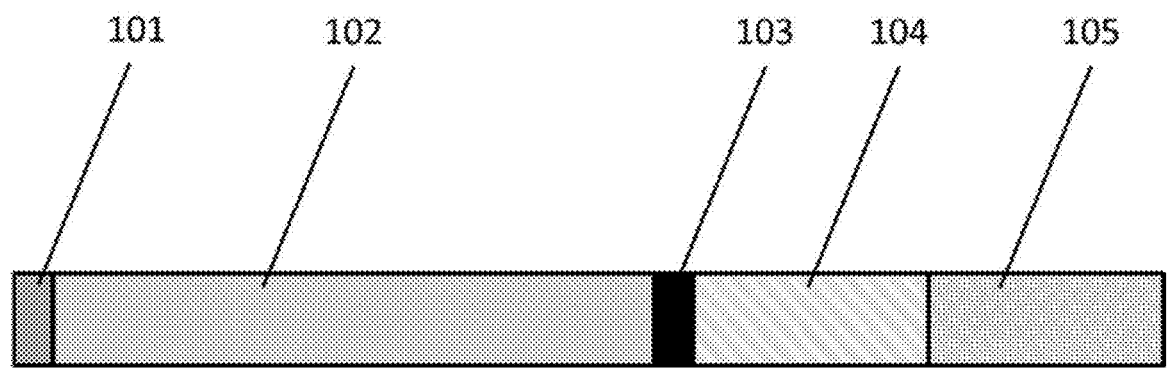
FIG. 1A illustrates a non-limiting schematic of a chimeric antigen receptor of the current disclosure. The figure is not represented to scale.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "about" indicates the value of the stated amountvaries by ±10% of the value. In some embodiments, the value of the stated amount varies by ±5% of the value. In some embodiments, the value of the stated amount varies by ±1% of the value.

As used herein the terms "individual," "subject," and "patient" are used interchangeably and include humans diagnosed with or suspected of being afflicted with cancer or other neoplasm.

Herein, unless stated otherwise, references to an NK cell or NK cells encompass both NK cell lines and primary NK cells.

As used herein the term "NK cell line" refers to any transformed or immortalized cell line that retain one or more natural killer cell properties. For example, in certain embodiments, the one or more natural killer cell properties retained are CD 56 expression, killer-cell immunoglobulin-like receptor (KIR) expression, or antigen independent cytotoxicity against a target cell line such as K562 cells. Common NK cell lines are, for example, the NK-92 or KHYG-1 cell line.

Natural Killer Cells

Engineered natural killer cells comprise one or more manipulations that distinguish them from a non-engineered natural killer cell. In certain embodiments, the engineered natural killer cell is engineered in that it comprises a polynucleotide that encodes any one or more of a chimeric antigen receptor, a TRAIL variant, a FUT6 or FUT7 protein, or a comprises deletion or reduced expression of a checkpoint inhibitor. The engineered natural killer cells (NK cells) of the present disclosure can be made from any NK cell population including primary cells or established cell lines. In certain embodiments, the NK cell is a human NK cell. Primary natural killer cells in humans express the cell surface marker CD56, and in certain embodiments, the engineered natural killer cells can be produced from CD56 positive cells as determined, by way of non-limiting example, by flow cytometry. In certain embodiments, the natural killer cell can be from an autologous source (same genetic background of source cell and recipient), or from a heterologous source (different genetic background of source cell and recipient). In certain embodiments, the NK cell is isolated from the peripheral blood of a donor or the individual to be treated using a method such as cell sorting or magnetic beads. NK cells isolated from a donor can be expanded ex vivo by culturing in interleukin-2 and interleukin-15 for greater than 7 days. In some embodiments, NK cells isolated from a donor can be expanded ex vivo by culturing in interleukin-2 and interleukin-15 for between about 7 days and about 14 days. NK cells can also be differentiated from stem or progenitor cells in in vitro culture using methods known in the art. In certain embodiments, the NK cell is differentiated from a bone-marrow derived stem cell. In certain embodiments, the NK cell is differentiated from an adult pluripotent cell. In certain embodiments, the NK cell is differentiated from an embryonic stem cell.

Engineered NK cells can also be made from a transformed NK cell line. In certain embodiments, the transformed NK cell line is a human cell line. Common NK cell lines that can be used are the NK-92 cell line (available from the ATCC; CRL-2497), or the KHYG-1 cell line. In certain embodiments, the engineered NK cell line is made from the KHYG-1 cell line. See Yagita et al., "A novel natural killer cell line (KHYG-1) from a patient with aggressive natural killer cell leukemia carrying a p53 point mutation." *Leukemia* 14(5):922-30. Despite commonalities between common NK cell lines, such as the expression of CD56, different cell lines possess different phenotypic and genotypic traits that may allow for greater suitability of a certain NK cell line compared to other NK cell lines with respect to developing a cell based therapy (e.g., CAR NK or NK cells expressing variant TRAIL proteins). In certain embodiments, the engineered NK cell line does not comprise an NK-92 cell line or derivative.

In a certain embodiment, described herein, the engineered NK cells are useful for treating a hematological malignancy. In order to facilitate such treatment, in certain embodiments, the cells exhibit increased homing to the bone marrow. In certain embodiments, the engineered NK cells exhibit a high level of E-selectin ligand expression. E-selectin is also known as: CD62 antigen-like family member E (CD62E); endothelial-leukocyte adhesion molecule 1 (ELAM-1); or leukocyte-endothelial cell adhesion molecule 2 (LECAM2). E-selectin binds to E-selectin ligands on the cells surface, which are glycoproteins and/or glycolipids which express the tetrasaccharide Sialyl Lewis X (SLe$^x$). SLe$^x$ is synthesized by the combined action of α-fucosyltransferases, α2-3-sialyltransferases, β-galactosyltransferases, and N-acetyl-β-glucosaminyltransferases. The HECA-452 antibody recognizes E-selectin ligands. In certain embodiments, the engineered NK cells comprise a population of engineered NK cells that exhibit at least at 25%, 50%, 60%, 70%, 75%, 80%, 90%, 95%, or more cells that stain positive with the HECA-452 antibody. In certain embodiments, the engineered NK cells comprise a population of NK cells that exhibit at least 50% or more cells that stain positive with the HECA-452 antibody. In certain embodiments, the engineered NK cells comprise a population of NK cells that exhibit at least 75% or more cells that stain positive with the HECA-452 antibody. In certain embodiments, the engineered NK cells comprise a population of NK cells that exhibit at least 80% or more cells that stain positive with the HECA-452 antibody. In certain embodiments, the engineered NK cells comprise a population of NK cells that exhibit at least 90% or more cells that stain positive with the HECA-452 antibody. Positively can be assessed, for example, by staining cells in vitro with a fluorescently conjugated HECA-452 antibody, and analyzing positively by flow cytometry comparing HECA-452 stained cells to isotype control stained cells. In certain embodiments, the population of engineered NK cells that exhibit HECA-452 positively have been chemically treated to increase fucosylation of cell surface proteins. In certain embodiments, the chemical treatment comprises the GDP-fucose substrate and the alpha 1,3 fucosyltransferase-VI enzyme.

In certain embodiments, the engineered NK cell is glycoengineered. In certain embodiments, the engineered NK cell exhibits a high level of E-selectin ligand. In certain embodiments, a high level of E-selectin ligand is exhibited by between a 6-fold and about a 100-fold increase in HECA-452 antibody binding compared to an isotype control antibody binding. In certain embodiments, a high level of E-selectin ligand is exhibited by at least a 6-fold increase in HECA-452 antibody binding compared to an isotype control antibody binding. In certain embodiments, a high level of E-selectin ligand is exhibited by at least a 7-fold increase in HECA-452 antibody binding compared to an isotype control antibody binding. In certain embodiments, a high level of E-selectin ligand is exhibited by at least a 8-fold increase in HECA-452 antibody binding compared to an isotype control antibody binding. In certain embodiments, a high level of E-selectin ligand is exhibited by at least a 9-fold increase in HECA-452 antibody binding compared to an isotype control antibody binding. In certain embodiments, a high level of E-selectin ligand is exhibited by at least a 10-fold increase in HECA-452 antibody binding compared to an isotype control antibody binding. In certain embodiments, a high level of E-selectin ligand is exhibited by at least a 20-fold increase in HECA-452 antibody binding compared to an isotype control antibody binding. In certain embodiments, a high level of E-selectin ligand is exhibited by at least a 50-fold increase in HECA-452 antibody binding compared to an isotype control antibody binding. In certain embodiments, a high level of E-selectin ligand is exhibited by at least a 100-fold increase in HECA-452 antibody binding compared to an isotype control antibody binding. This increase in binding can be analyzed, for example, by comparing mean fluorescence intensity of HECA-452 antibody binding to that of an isotype control antibody using flow cytometry. In certain embodiments, the NK cell that exhibits a high level of HECA-452 antibody binding is a KHYG-1 cell line. In certain embodiments, the population of engineered NK cells that exhibit high levels of HECA-452 binding have been chemically treated to increase fucosylation or sialylation of cell surface proteins. In certain embodiments, the chemical treatment comprises the GDP-fucose substrate and the alpha 1,3 fucosyltransferase-VI enzyme. In certain embodiments, the NK cell has been engineered to exhibit a high level of HECA-452 antibody binding by expressing FUT6, FUT7, or both. In certain embodiments, FUT6, or FUT7 expression is achieved by introducing mRNA or a DNA plasmid or viral vector into an NK cell that exhibits a low level of HECA-452 antibody binding, for example an NK-92 cell. In certain embodiments, an immortalized NK cell line, such as NK-92 cells, can be stably transfected with a nucleic acid that encodes FUT6, FUT7, or both. In certain embodiments, a high level of expression of FUT6 or FUT7 is at least a 2, 5, or 10-fold increase in FUT6 or FUT7 expression or activity as monitored by mRNA, western blot, or enzymatic assay. In certain embodiments, a high level of expression of FUT6 or FUT7 is between about a 2-fold and about a 10-fold increase in FUT6 or FUT7 expression or activity as monitored by mRNA, western blot, or enzymatic assay. In certain embodiments, the engineered NK cell expresses CD65. In certain embodiments, the engineered NK cell expresses CD65s.

In certain embodiments, the engineered NK cells comprise a low level of cell-surface expression of a TRAIL receptor. In certain embodiments, the TRAIL receptor is DR4 or DR5. In certain embodiments, the low level of cell-surface expression of a TRAIL receptor comprises a lack of detectable TRAIL receptor activity. In certain embodiments, the low level of cell-surface expression of TRAIL receptor comprises a level marked by anti-TRAIL antibody reactivity that is comparable to an isotype control. In certain embodiments, the low level of cell-surface expression of TRAIL receptor comprises a level marked by anti-TRAIL antibody reactivity that is less than 5-fold compared to an isotype control. In certain embodiments, the low level of cell-surface TRAIL receptor comprises a level marked by anti-TRAIL antibody reactivity that is less than 2-fold compared to an isotype control. Cell surface TRAIL receptor expression can be quantified, for example, using flow cytometry as detailed in the examples.

Chimeric Antigen Receptors

Figure 1B:
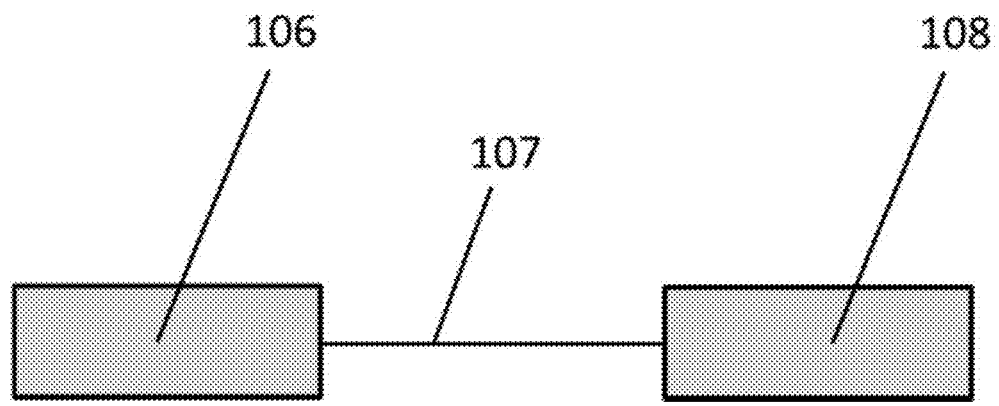
FIG. 1B illustrates a non-limiting schematic of a targeting domain of a chimeric antigen receptor of the current disclosure. The figure is not represented to scale.

A chimeric antigen receptor (CAR) is a recombinant antigen receptor that is intended to introduce a certain antigen specificity to an immune effector cell. The CAR comprises a defined polypeptide sequence expressed from an exogenous polynucleotide that has been introduced into the immune effector cell, either transiently or integrated into the genome. A schematic for a generic CAR is illustrated in FIG. 1A. Chimeric antigen receptors comprise a leader sequence 101, a targeting domain 102, a transmembrane domain 103, and one or more intracellular signaling domains (104 and 105). In certain embodiments, the targeting domain is derived from an antibody molecule, and comprises one or more complementarity determining regions (CDRs) from the antibody molecule that confer antigen specificity on the CAR. In certain embodiments, the targeting domain of the CAR for use in the engineered NK cells of this disclosure is a single chain variable fragment (scFv) as shown in FIG. 1B. An scFv comprises the variable chain portion of an immunoglobulin light chain 106, and an immunoglobulin heavy chain molecule 108 separated by a flexible linker polypeptide 107. The order of the heavy and light chains is not limiting and can be reversed. The flexible polypeptide linker allows the heavy and light chains to associate with one another and reconstitute an immunoglobulin antigen binding domain. In certain embodiments, the light chain variable region comprises three CDRs and the heavy chain variable region comprises three CDRs. In certain embodiments, the CDRs for use in the targeting domain are derived from an antibody molecule of any species (e.g., human, mouse, rat, rabbit, goat, sheep) and the framework regions between the CDRs are humanized or comprise a sequence that is at least 85%, 90%, 95 or 99% identical to a human framework region.

When the targeting domain of the CAR comprises an scFv, the immunoglobulin light chain and the immunoglobulin heavy chain are joined by polypeptide linkers of various lengths. In certain embodiments, the polypeptide linker comprises a length greater than or equal to 10 amino acids. In certain embodiments, the polypeptide linker comprises a length greater than 10, 15, 20, or 25 amino acids. In certain embodiments, the polypeptide linker comprises a length less than or equal to 30 amino acids. In certain embodiments, the polypeptide linker comprises a length less than 15, 20, 25, or 30 amino acids. In certain embodiments, the polypeptide linker comprises between 10 and 30 amino acids in length. In certain embodiments, the polypeptide linker comprises between 10 and 25 amino acids in length. In certain embodiments, the polypeptide linker comprises between 10 and 20 amino acids in length. In certain embodiments, the polypeptide linker comprises between 10 and 15 amino acids in length. In certain embodiments, the polypeptide linker comprises between 15 and 30 amino acids in length. In certain embodiments, the polypeptide linker comprises between 20 and 30 amino acids in length. In certain embodiments, the polypeptide linker comprises between 25 and 30 amino acids in length. In certain embodiments, the polypeptide linker comprises hydrophilic amino acids. In certain embodiments, the polypeptide linker consists of hydrophilic amino acids. In certain embodiments, the polypeptide linker comprises the amino acid sequence GSTSGSGKPGSGEGSTKG. In certain embodiments, the polypeptide linker comprises a $G_4S$ sequence (GGGGS). The $G_4S$ linker allows for flexibility and protease resistance of the linker. In certain embodiments, the $G_4S$ linker is consecutively repeated in the polypeptide linker 1, 2, 3, 4, 5, 6, 7, or 8 times.

The CARs of this disclosure further comprise an $NH_2$-terminal leader sequence 101. The leader sequence (also know as the signal peptide) allows the expressed CAR construct to enter the endoplasmic reticulum (ER) and target the cell surface. The leader sequence is cleaved in the ER and the mature cell surface CAR does not possess a leader sequence. In general, the leader sequence length will be in the range of 5 to 30 amino acids, and comprise a stretch of hydrophobic amino acids. In certain embodiments, the leader sequence comprises greater than 5, 10, 15, 20, or 25 amino acids in length. In certain embodiments, the leader sequence comprises less than 10, 15, 20, 25, or 30 amino acids in length. In certain embodiments, the leader sequence comprises a sequence derived from any secretory protein. In certain embodiments, the leader sequence comprises a sequence derived from the CD8 alpha leader sequence.

The CARs of this disclosure further comprise a transmembrane domain. See FIG. 1A feature 103. The transmembrane domain comprises hydrophobic amino acid residues and allows the CAR to be anchored into the cell membrane of the engineered NK cell. In certain embodiments, the transmembrane domain comprises an amino acid sequence derived from a transmembrane protein. In certain embodiments, the transmembrane domain comprises an amino acid sequence derived from the transmembrane domain of the alpha, beta, or zeta chain of the T-cell receptor, CD27, CD28, CD3 epsilon, CD45, CD4, CD5, CD8, CD9, CD16, CD22, CD33, CD37, CD64, CD80, CD86, CD134, CD137, and CD154. In certain embodiments, the CAR comprises a transmembrane with an amino acid sequence derived from the transmembrane domain of CD8. In certain embodiments, the CAR comprises a transmembrane domain with an amino acid sequence derived from the transmembrane domain of human CD8 alpha.

The CARs of this disclosure further comprise one or more intracellular signaling domains. See FIG. 1A feature 104 and 105. The intracellular signaling domain increases the potency of the CAR and comprises a an intracellular signaling domain derived from a protein involved in immune cell signal transduction. In certain embodiments, the one or more intracellular signaling domains comprise an intracellular signaling domain derived from CD3 zeta CD28, OX-40, 4-1BB, DAP10, DAP12, 2B4 (CD244), or any combination thereof. In certain embodiments, the one or more intracellular signaling domains comprise an intracellular signaling domain derived from any two of CD3 zeta CD28, OX-40, 4-1BB, DAP10, DAP12, 2B4 (CD244), or any combination thereof. In certain embodiments, the CAR comprises at least two intracellular signaling domains derived from CD3 zeta and 4-1BB.

The CARs of this disclosure can also comprise a hinge region located between the targeting domain and the transmembrane domain. The hinge region comprises hydrophilic amino acids and allows flexibility of the targeting domain with respect to the cell surface. In certain embodiments, the hinge region comprises greater than 5, 10, 15, 20, 25, or 30 amino acids. In certain embodiments, the hinge region comprises less than 10, 15, 20, 25, 30, or 35 amino acids.

It is preferred that the CD38 CAR of the present invention has a binding domain that comprises a heavy chain variable region comprising SEQ ID NO: 1. Optionally, the heavy chain variable region comprises SEQ ID NO: 7. It is preferred that the CD38 CAR binding domain comprises a light chain variable region comprising SEQ ID NO: 23 or SEQ ID NO: 28.

The preferred CD38 CAR of the examples has a binding domain that comprises a heavy chain variable region comprising SEQ ID NO: 1 and a light chain variable region comprising SEQ ID NO: 23.

It is preferred that the CD38 CAR binding domain comprises one or more or all of heavy chain CDRs selected from SEQ ID NO: 29, SEQ ID NO: 30 and SEQ ID NO: 31. Optionally, the CAR comprises one or more or all of heavy chain CDRs selected from SEQ ID NO: 32, SEQ ID NO: 33 and SEQ ID NO: 34.

It is preferred that the CD38 CAR binding domain comprises one or more or all of light chain CDRs selected from SEQ ID NO: 35, SEQ ID NO: 36 and SEQ ID NO: 37, or SEQ ID NO: 38, SEQ ID NO: 39 and SEQ ID NO: 40.

Preferably, fragments and variants of the above-mentioned heavy and light chains provide CAR binding domains with substantially the same CD38 binding activity, wherein fragments include peptides that have been truncated and/or have had amino acids deleted and/or modified. It is preferred that any fragment/variant, according to the invention, retains at least 50%, at least 60%, at least 70%, at least 80%, most preferably at least 90% of the binding activity of the preferred CAR of the examples. It is further preferred that any fragment/variant, according to the invention, has a binding activity that does not exceed the binding activity of the preferred CAR by more than 10%, more than 20%, more than 50%, preferably not more than 100%.

It is preferred that the CD38 CAR binding domain comprises a heavy chain variable region having a sequence homology of at least 50%, at least 60%, at least 70%, at least 80%, more preferably at least 90% with SEQ ID NO: 1. Optionally, the CD38 CAR comprises a heavy chain variable region having a sequence homology of at least 50%, at least 60%, at least 70%, at least 80%, more preferably at least 90% with SEQ ID NO: 7.

It is preferred that the CD38 CAR binding domain comprises a light chain variable region having a sequence homology of at least 50%, at least 60%, at least 70%, at least 80%, more preferably at least 90% with SEQ ID NO: 23 or SEQ ID NO: 28.

It is preferred that the CD38 CAR binding domain comprises one or more or all of heavy chain CDRs having a sequence homology of at least 70%, at least 80%, more preferably at least 90% with SEQ ID NO: 29, SEQ ID NO: 30 and SEQ ID NO: 31. Optionally, the CD38 CAR comprises one or more or all of heavy chain CDRs having a sequence homology of at least 70%, at least 80%, more preferably at least 90% with SEQ ID NO: 32, SEQ ID NO: 33 and SEQ ID NO: 34.

It is preferred that the CD38 CAR binding domain comprises one or more or all of light chain CDRs having a sequence homology of at least 70%, at least 80%, more preferably at least 90% with SEQ ID NO: 35, SEQ ID NO: 36 and SEQ ID NO: 37, or SEQ ID NO: 38, SEQ ID NO: 39 and SEQ ID NO: 40.

It is preferred that the CD38 CAR comprises one or more co-stimulatory domains selected from SEQ ID NO: 41, SEQ ID NO: 42 and SEQ ID NO: 43. It is preferred that the CAR comprises a co-stimulatory domain having a sequence homology of at least 50%, at least 60%, at least 70%, at least 80%, more preferably at least 90% with SEQ ID NO: 41, SEQ ID NO: 42 or SEQ ID NO: 43.

It is preferred that the CD38 CAR binding domain comprises a heavy chain variable region comprising a sequence that is a fragment of SEQ ID NO: 1 being at least 60 amino acids, at least 70 amino acids, at least 80 amino acids, at least 90 amino acids, at least 100 amino acids, at least 110 amino acids, more preferably at least 120 amino acids in length. In some embodiments, the CD38 CAR binding domain comprises a heavy chain variable region comprising a sequence that is a fragment of SEQ ID NO: 1 being between about 60 and about 120 amino acids in length. Optionally, the CD38 CAR comprises a heavy chain variable region comprising a sequence that is a fragment of SEQ ID NO: 7 being at least 60 amino acids, at least 70 amino acids, at least 80 amino acids, at least 90 amino acids, at least 100 amino acids, at least 110 amino acids, more preferably at least 120 amino acids in length. In some embodiments, the CD38 CAR binding domain comprises a heavy chain variable region comprising a sequence that is a fragment of SEQ ID NO: 7 being between about 60 and about 120 amino acids in length.

It is preferred that the CD38 CAR binding domain comprises a light chain variable region comprising a sequence that is a fragment of SEQ ID NO: 23 or SEQ ID NO: 28 being at least 50 amino acids, at least 60 amino acids, at least 70 amino acids, at least 80 amino acids, at least 90 amino acids, more preferably at least 100 amino acids in length.

CAR Targeting Domains

In certain embodiments, disclosed herein, a "cancer associated antigen" refers to a molecular marker of cancer that is expressed by a cancerous cell to a greater extent than is expressed by a normal cell. Cancer associated antigens are generally proteins or polypeptides derived therefrom, but can be glycans, lipids, or other small organic molecules. Additionally, a cancer antigen can arise through increases or decreases in post-translational processing exhibited by a cancer cell compared to a normal cell, for example, protein glycosylation, protein lipidation, protein phosphorylation, or protein acetylation. Non-limiting examples of a cancer associated antigen comprise CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEUSGC, NeuGcGM3, GD2, CLL-1, HERV-K.

In certain embodiments, disclosed herein, a "blood cancer associated antigen" refers to a molecular marker of cancer that is expressed by a leukemia, lymphoma, myeloma to a greater extent than is expressed on a hematological cell. Blood cancer associated antigens are generally proteins or polypeptides derived therefrom, but can be glycans, lipids, or other small organic molecules. Additionally, a blood cancer antigen can arise through increases or decreases in post-translational processing exhibited by a leukemia, lymphoma, or myeloma cell compared to a normal cell, for example, protein glycosylation, protein lipidation, protein phosphorylation, or protein acetylation. Non limiting examples of a blood cancer associated antigen comprise CD38, CD319/SLAMF-7, TNFRSF17/BCMA, SYND1/CD138, CD229, CD47, CD123/IL3-RA, CD19, CD20, CD22, GD2, CLL-1, HERV-K. Non-limiting examples of blood cancers include acute lymphoblastic leukemia, chronic lymphocytic leukemia, diffuse large B cell lymphoma, follicular lymphoma, mantle cell lymphoma, acute myelogenous leukemia, chronic myelogenous leukemia, hairy cell leukemia, T-cell prolymphocytic leukemia, multiple myeloma, smoldering multiple myeloma, light chain myeloma, or large granular lymphocytic leukemia.

In certain embodiments, the engineered NK cell comprises a CAR with a targeting domain that specifically binds a cell surface protein. In certain embodiments, the engineered NK cell comprises two or more CARS with targeting domains that specifically bind two or more distinct cell surface proteins. In certain embodiments, the CAR targeting domain specifically binds a cancer associated antigen on the cell surface of a cancerous cell. In certain embodiments, the CAR specifically binds CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, HERV-K.

CD38, also known as cyclic ADP ribose hydrolase, is a cell surface glycoprotein found primarily on immune cells. CD38 is involved in the regulation of intracellular calcium, and is overexpressed in many different cancers including leukemia, myeloma, and many solid tumors. In certain embodiments, the engineered NK cells of the current disclosure express a CAR with a targeting domain 102 that is specific for CD38. In certain embodiments, the CD38 CAR comprises an amino acid sequence at least 80% identical to that set forth in any one of SEQ ID NOs: 1-6. In certain embodiments, the CD38 CAR comprises an amino acid sequence at least 90% identical to that set forth in any one of SEQ ID NOs: 1-6. In certain embodiments, the CD38 CAR comprises an amino acid sequence at least 95% identical to that set forth in any one of SEQ ID NOs: 1-6. In certain embodiments, the CD38 CAR comprises an amino acid sequence at least 98% identical to that set forth in any one of SEQ ID NOs: 1-6. In certain embodiments, the CD38 CAR comprises an amino acid sequence at least 99% identical to that set forth in any one of SEQ ID NOs: 1-6. In certain embodiments, the CD38 CAR comprises a sequence identical to that set forth in any one of SEQ ID NOs: 1-6.

In certain embodiments, the engineered NK cell expresses a CAR with a targeting domain comprising an amino acid sequence set forth in SEQ ID NO: 1, and an amino acid sequence set forth in SEQ ID NO: 2. In certain embodiments, the CAR comprises an amino acid sequence 80% identical to that set forth in SEQ ID NO: 1, and an amino acid sequence 80% identical to that set forth in SEQ ID NO: 2. In certain embodiments, the CAR comprises an amino acid sequence 90% identical to that set forth in SEQ ID NO: 1, and an amino acid sequence 90% identical to that set forth in SEQ ID NO: 2. In certain embodiments, the CAR comprises an amino acid sequence 95% identical to that set forth in SEQ ID NO: 1, and an amino acid sequence 95% identical to that set forth in SEQ ID NO: 2. In certain embodiments, the CAR comprises an amino acid sequence 98% identical to that set forth in SEQ ID NO: 1, and an amino acid sequence 98% identical to that set forth in SEQ ID NO: 2. In certain embodiments, the CAR comprises an amino acid sequence 99% identical to that set forth in SEQ ID NO: 1, and an amino acid sequence 99% identical to that set forth in SEQ ID NO: 2. In certain embodiments, SEQ ID NO: 1 and SEQ ID NO: 2 are joined by a flexible polypeptide linker. In certain embodiments, the flexible polypeptide linker joins the COOH terminus of the polypeptide set forth in SEQ ID NO: 1 to the NH$_2$ terminus of the polypeptide set forth in SEQ ID NO: 2. In certain embodiments, the flexible polypeptide linker joins the COOH terminus of the polypeptide set forth in SEQ ID NO: 2 to the NH$_2$ terminus of the polypeptide set forth in SEQ ID NO: 1.

In certain embodiments, the engineered NK cell expresses a CAR with a targeting domain comprising an amino acid sequence set forth in SEQ ID NO: 3, and an amino acid sequence set forth in SEQ ID NO: 4. In certain embodiments, the CAR comprises an amino acid sequence 80% identical to that set forth in SEQ ID NO: 3, and an amino acid sequence 80% identical to that set forth in SEQ ID NO: 4. In certain embodiments, the CAR comprises an amino acid sequence 90% identical to that set forth in SEQ ID NO: 3, and an amino acid sequence 90% identical to that set forth in SEQ ID NO: 4. In certain embodiments, the CAR comprises an amino acid sequence 95% identical to that set forth in SEQ ID NO: 3, and an amino acid sequence 95% identical to that set forth in SEQ ID NO: 4. In certain embodiments, the CAR comprises an amino acid sequence 98% identical to that set forth in SEQ ID NO: 3, and an amino acid sequence 98% identical to that set forth in SEQ ID NO: 4. In certain embodiments, the CAR comprises an amino acid sequence 99% identical to that set forth in SEQ ID NO: 3, and an amino acid sequence 99% identical to that set forth in SEQ ID NO: 4. In certain embodiments, SEQ ID NO: 3 and SEQ ID NO: 4 are joined by a flexible polypeptide linker. In certain embodiments, the flexible polypeptide linker joins the COOH terminus of the polypeptide set forth in SEQ ID NO: 3 to the NH$_2$ terminus of the polypeptide set forth in SEQ ID NO: 4. In certain embodiments, the flexible polypeptide linker joins the COOH terminus of the polypeptide set forth in SEQ ID NO: 4 to the NH$_2$ terminus of the polypeptide set forth in SEQ ID NO: 3.

In certain embodiments, the engineered NK cell expresses a CAR with a targeting domain comprising an amino acid sequence set forth in SEQ ID NO: 5, and an amino acid sequence set forth in SEQ ID NO: 6. In certain embodiments, the CAR comprises an amino acid sequence 80% identical to that set forth in SEQ ID NO: 5, and an amino acid sequence 80% identical to that set forth in SEQ ID NO: 6. In certain embodiments, the CAR comprises an amino acid sequence 90% identical to that set forth in SEQ ID NO: 5, and an amino acid sequence 90% identical to that set forth in SEQ ID NO: 6. In certain embodiments, the CAR comprises an amino acid sequence 95% identical to that set forth in SEQ ID NO: 5, and an amino acid sequence 95% identical to that set forth in SEQ ID NO: 6. In certain embodiments, the CAR comprises an amino acid sequence 98% identical to that set forth in SEQ ID NO: 5, and an amino acid sequence 98% identical to that set forth in SEQ ID NO: 6. In certain embodiments, the CAR comprises an amino acid sequence 99% identical to that set forth in SEQ ID NO: 5, and an amino acid sequence 99% identical to that set forth in SEQ ID NO: 6. In certain embodiments, SEQ ID NO: 5 and SEQ ID NO: 6 are joined by a flexible polypeptide linker. In certain embodiments, the flexible polypeptide linker joins the COOH terminus of the polypeptide set forth in SEQ ID NO: 5, to the NH$_2$ terminus of the polypeptide set forth in SEQ ID NO: 6. In certain embodiments, the flexible polypeptide linker joins the COOH terminus of the polypeptide set forth in SEQ ID NO: 6 to the NH$_2$ terminus of the polypeptide set forth in SEQ ID NO: 5.

The engineered NK cell of the current disclosure may comprise a CD38 specific CAR exhibiting an affinity that has been tuned for an optimal cancer response, while also minimizing reactivity to CD38 that is expressed on non-cancerous or non-tumor cells. Daratumumab is a monoclonal antibody that exhibits high affinity for the CD38 receptor. In certain embodiments, the CAR comprises a targeting domain that is derived from an antibody that exhibits a lower affinity for CD38 than Daratumumab. In certain embodiments, the CAR comprises a targeting domain that is derived from an antibody that exhibits a 25% lower affinity for CD38 than Daratumumab. In certain embodiments, the CAR comprises a targeting domain that is derived from an antibody that exhibits a 50% lower affinity for CD38 than Daratumumab. In certain embodiments, the CAR comprises a targeting domain that is derived from an antibody that exhibits a 2-fold lower affinity for CD38 than Daratumumab. Antibody affinity can be measured for example by the use of surface plasmon resonance (e.g., Biacore).

Bispecific CARS

The engineered NK cells may be bispecific, that is, express bispecific CARs or multiple different CARs, wherein their affinity is for two distinct ligands/antigens. Bispecific CAR-NKs can be used either for increasing the number of potential binding sites on cancer cells or, alternatively, for localizing cancer cells to other immune effector cells which express ligands specific to the NK-CAR. For use in cancer therapy, a bispecific CAR may bind to a target tumor cell and to an effector cell, e.g. a T cell, NK cell or macrophage. Thus, for example, in the case of multiple myeloma, a bispecific CAR may bind a T cell antigen (e.g. CD3, etc.) and a tumor cell marker (e.g. CD38, etc.). A bispecific CAR may alternatively bind to two separate tumor cell markers, increasing the overall binding affinity of the NK cell for the target tumor cell. This may reduce the risk of cancer cells developing resistance by downregulating one of the target antigens. An example in this case, in multiple myeloma, would be a CAR binding to both CD38 and CS-1/SLAMF7. Another tumor cell marker suitably targeted by the CAR is a "don't eat me" type marker on tumors, exemplified by CD47.

The engineered NK cells of the current disclosure may comprise a bispecific CAR or multiple CARs expressed by the same NK cell. This allows the NK cells to target two different antigens simultaneously. In certain embodiments, the bispecific CAR has specificity for any two of the following antigens: CD38, CD319/SLAMF-7, TNFRSF17/BCMA, CD123/IL3-RA, SYND1/CD138, CD229, CD47, Her2/Neu, epidermal growth factor receptor (EGFR), CD19, CD20, CD22, Mesothelin, EpCAM, MUC1, MUC16, Tn antigen, NEU5GC, NeuGcGM3, GD2, CLL-1, CD123, HERV-K. In certain embodiments, the bispecific nature of the CAR NK cell may allow binding to a tumor antigen and another immune cell, such as a T cell or dendritic cell. In certain embodiments, the bispecific nature of the CAR NK cell may allow binding to a checkpoint inhibitor, such as PDL-1, or CD47. In certain embodiments, the first CAR has CD38 specificity, and the second CAR has specificity for any one of SLAMF-7, BCMA, CD138, CD229, PDL-1, or CD47. In certain embodiments, the first CAR has specificity for CD38, and the second CAR has specificity for SLAMF-7, BCMA, CD138, CD229. In certain embodiments, the first CAR has specificity for CD38, and the second CAR has specificity for SLAMF-7. In certain embodiments, the first CAR has specificity for CD38, and the second CAR has specificity for BCMA. In certain embodiments, the first CAR has specificity for CD38, and the second CAR has specificity for CD138. In certain embodiments, the first CAR has specificity for CD38, and the second CAR has specificity for CD229.

TNF-Related Apoptosis-Inducing Ligand

TNF-related apoptosis-inducing ligand (TRAIL), also known as tumor necrosis factor ligand superfamily member 10, is a protein ligand that induces cell death though the initiation of apoptosis. Apoptosis is initiated through the binding of TRAIL to TRAIL receptors that are expressed on the cell surface of many different types of cells, including cancer cells. The engineered NK cells of the present disclosure may express a variant TRAIL polypeptide that has been modified from the wild-type TRAIL protein sequence by at least one amino acid residue in order to increase its binding affinity for the death inducing receptors DR4, DR5 or both, while reducing binding affinity for decoy receptors, such as DcR1 or DcR2. In certain embodiments, the engineered NK cells expresses a CAR and a variant TRAIL polypeptide. In certain embodiments, the TRAIL variant displays increased binding affinity to one or more TRAIL receptors. In certain embodiments, the TRAIL variant displays increased binding affinity to the TRAIL receptor DR4. In certain embodiments, the TRAIL variant displays increased binding affinity to the TRAIL receptor DR5. In certain embodiments, the TRAIL variant displays increased binding affinity to the TRAIL receptor DR4 and DR5. Wildtype TRAIL is typically known to have a KD of >2 nM for DR4, >5 nM for DR5 and >20 nM for the decoy receptor DcR1 (WO 2009/077857; measured by surface plasmon resonance), or around 50 to 100 nM for DR4, 1 to 10 nM for DR5 and 175 to 225 nM for DcR1 (Truneh, A. et al. 2000; measured by isothermal titration calorimetry and ELISA). Therefore, an increased affinity for DR4 is suitably defined as a KD of <2 nM or <50 nM, respectively, whereas an increased affinity for DR5 is suitably defined as a KD of <5 nM or <1 nM, respectively. A reduced affinity for decoy receptor DcR1 is suitably defined as a KD of >50 nM or >225 nM, respectively. In any case, an increase or decrease in affinity exhibited by the TRAIL variant/mutant is relative to a baseline affinity exhibited by wildtype TRAIL. In certain embodiments, the affinity of the TRAIL variant for the TRAIL receptor is increased at least about 10%, 15%, 20%, 25%, or 50% compared with that exhibited by wildtype TRAIL. In certain embodiments, the affinity of the TRAIL variant for the TRAIL receptor is increased between about 10% and about 50% compared with that exhibited by wildtype TRAIL. In a certain embodiment, the TRAIL variant increases apoptosis compared to wildtype as measured by caspase 8 activation in a target cell. In certain embodiments, the TRAIL variant increases caspase 8 activation compared to wildtype in a target cell by at least 2-fold. In certain embodiments, the TRAIL variant increases caspase 8 activation compared to wildtype in a target cell by between about 2-fold and about 10-fold. In certain embodiments, the TRAIL receptor variant comprises an amino acid mutation of human TRAIL comprising D269H, S159R, E195R, G131R, N199R, K201H, or any combination thereof. In certain embodiments, the TRAIL receptor variant comprises two amino acid mutations of human TRAIL, D269H and E195R. In certain embodiments, the TRAIL receptor variant comprises a D269H mutation. In certain embodiments, the TRAIL receptor variant comprises a E195R mutation. In certain embodiments, the TRAIL receptor variant comprises three amino acid mutations of human TRAIL, G131R, N199R, and K201H. In certain embodiments, the mutant TRAIL receptor is expressed on a primary T cell or T cell line. In certain embodiments, the TRAIL receptor is encoded by a polynucleotide that has been transfected into the T cell line.

Checkpoint Inhibitory Receptors

Checkpoint inhibitory receptors are expressed on the surface of immune effector cells, such as T cells and NK cells, and negatively regulate cytotoxicity of these cells. Examples of checkpoint inhibitory receptors include PD-1, CTLA-4 and CD96, all of which are expressed on NK cells. In certain embodiments, engineered NK cells comprise reduced or absent checkpoint inhibitory receptor function. In certain embodiments, the checkpoint inhibitory receptors with reduced or absent function comprise one or more or all of CD96 (TACTILE), CD152 (CTLA4), CD223 (LAG-3), CD279 (PD-1), CD328 (SIGLEC7), SIGLEC9, TIGIT, and/or TIM-3. In certain embodiments, the checkpoint inhibitory receptor comprises one or more of CD96 (TACTILE), CD152 (CTLA4), or CD328 (SIGLEC7). In certain embodiments, the NK cell cells comprise reduced or absent checkpoint inhibitory receptor function for two or more checkpoint inhibitory receptors. In certain embodiments, the two or more checkpoint inhibitory receptors comprise CD96 (TACTILE), CD152 (CTLA4), or CD328 (SIGLEC7). In certain embodiments, the NK cells exhibit reduced or absent checkpoint inhibitory receptor function for three checkpoint inhibitory receptors. In certain embodiments, the three checkpoint inhibitory receptors comprise CD96 (TACTILE), CD152 (CTLA4), or CD328 (SIGLEC7). In certain embodiments, the engineered NK cell comprises a CD38 CAR, and deletion or reduction of a checkpoint inhibitor receptor. In certain embodiments, the engineered NK cell comprises a CD38 CAR, a variant TRAIL protein, and deletion or reduction of a checkpoint inhibitor receptor.

In certain embodiments, the engineered NK cells have been modified to reduce checkpoint inhibitory receptors by genetic deletion via a CRISPR/Cas9 or TALEN mechanism. In certain embodiments, the engineered NK cell comprises genetic deletion of CD96 (TACTILE). In certain embodiments, the engineered NK cell comprises genetic deletion of CD328 (SIGLEC7). In certain embodiments, the engineered NK cell comprises genetic deletion of CD152 (CTLA4). In certain embodiments, the engineered NK cell comprises genetic deletion of CD279 (PD-1). In certain embodiments, the engineered NK cell comprises genetic deletion of any two or more of CD96 (TACTILE), CD328 (SIGLEC7), CD152 (CTLA4), or CD279 (PD-1). In certain embodiments, the engineered NK cell comprises genetic deletion of any three or more of CD96 (TACTILE), CD328 (SIGLEC7), CD152 (CTLA4), or CD279 (PD-1). In certain embodiments, engineered NK cells have been modified to reduce checkpoint inhibitory receptor expression by siRNA, shRNA or antisense RNA. In certain embodiments, the engineered NK cell comprises reduced expression of CD96 (TACTILE). In certain embodiments, the engineered NK cell comprises reduced expression of CD328 (SIGLEC7). In certain embodiments, the engineered NK cell comprises reduced expression of CD152 (CTLA4). In certain embodiments, the engineered NK cell comprises reduced expression of CD279 (PD-1). In certain embodiments, the engineered NK cell comprises reduced expression of any two or more of CD96 (TACTILE), CD328 (SIGLEC7), CD152 (CTLA4), or CD279 (PD-1). In certain embodiments, the engineered NK cell comprises reduced expression of any three or more of CD96 (TACTILE), CD328 (SIGLEC7), CD152 (CTLA4), or CD279 (PD-1).

In certain embodiments, the engineered NK cells that express a high level of E-selectin ligand evidenced by binding of the HECA-452 antibody, as detailed above, comprise a CD38 CAR, a TRAIL variant polypeptide, or deletion or reduction of a checkpoint inhibitor receptor. In certain embodiments, the engineered NK cells that express a high level of E-selectin ligand comprise a CD38 CAR and a TRAIL variant polypeptide. In certain embodiments, the engineered NK cells that express a high level of E-selectin ligand comprise a CD38 CAR and deletion or reduction of a checkpoint inhibitor receptor. In certain embodiments, the engineered NK cells that express a high level of E-selectin ligand comprise a CD38 CAR, a TRAIL variant polypeptide, and deletion or reduction of one or more checkpoint inhibitors checkpoint inhibitor. In certain embodiments, the CD38 CAR comprises a targeting domain sequence at least 80% identical to that set forth in any one of SEQ ID NOs: 1-6. In certain embodiments, the CD38 CAR comprises a targeting domain sequence at least 90% identical to that set forth in any one of SEQ ID NOs: 1-6. In certain embodiments, the CD38 CAR comprises a sequence at least 95% identical to that set forth in any one of SEQ ID NOs: 1-6. In certain embodiments, the CD38 CAR comprises a sequence at least 98% identical to that set forth in any one of SEQ ID NOs: 1-6. In certain embodiments, the CD38 CAR comprises a sequence at least 99% identical to that set forth in any one of SEQ ID NOs: 1-6. In certain embodiments, the CD38 CAR comprises a sequence identical to that set forth in any one of SEQ ID NOs: 1-6. In certain embodiments, the TRAIL receptor variant comprises two amino acid mutations of human TRAIL, D269H and E195R. In certain embodiments, the TRAIL receptor variant comprises three amino acid mutations of human TRAIL, G131R, N199R, and K201H. In certain embodiments, the TRAIL receptor variant comprises a D269H mutation. In certain embodiments, the TRAIL receptor variant comprises a E195R mutation. In certain embodiments, the checkpoint inhibitory receptors are one or more or all of CD96 (TACTILE), CD152 (CTLA4), CD223 (LAG-3), CD279 (PD-1), CD328 (SIGLEC7), SIGLEC9, TIGIT, and/or TIM-3.

In certain embodiments, the engineered NK cells that express a high level of E-selectin ligand evidenced by binding of the HECA-452 antibody is a KHYG-1 cell. In certain embodiments, the KHYG-1 cell comprise a CD38 CAR, a TRAIL variant polypeptide, or deletion or reduction in function of a checkpoint inhibitor receptor. In certain embodiments, the KHYG-1 cell comprises a CD38 CAR and a TRAIL variant polypeptide. In certain embodiments, the KHYG-1 cell comprises a CD38 CAR, and a deletion or reduction in function of a checkpoint inhibitor receptor. In certain embodiments, the KHYG-1 cell comprises a CD38 CAR, a TRAIL variant polypeptide, and deletion or reduction in function of a checkpoint inhibitor receptor. In certain embodiments, the CD38 CAR comprises a targeting domain sequence at least 80% identical to that set forth in any one of SEQ ID NOs: 1-6. In certain embodiments, the CD38 CAR comprises a targeting domain sequence at least 90% identical to that set forth in any one of SEQ ID NOs: 1-6. In certain embodiments, the CD38 CAR comprises a sequence at least 95% identical to that set forth in any one of SEQ ID NOs: 1-6. In certain embodiments, the CD38 CAR comprises a sequence at least 98% identical to that set forth in any one of SEQ ID NOs: 1-6. In certain embodiments, the CD38 CAR comprises a sequence at least 99% identical to that set forth in any one of SEQ ID NOs: 1-6. In certain embodiments, the CD38 CAR comprises a sequence identical to that set forth in any one of SEQ ID NOs: 1-6. In certain embodiments, the TRAIL receptor variant comprises two amino acid mutations of human TRAIL, D269H and E195R. In certain embodiments, the TRAIL receptor variant comprises three amino acid mutations of human TRAIL, G131R, N199R, and K201H. In certain embodiments, the TRAIL receptor variant comprises a D269H mutation. In certain embodiments, the TRAIL receptor variant comprises a E195R mutation. In certain embodiments, the checkpoint inhibitory receptors are one or more or all of CD96 (TACTILE), CD152 (CTLA4), CD223 (LAG-3), CD279 (PD-1), CD328 (SIGLEC7), SIGLEC9, TIGIT, and/or TIM-3.

Methods of Making Engineered Natural Killer Cells

Engineered natural killer cells may be made using several different techniques known in the art. In certain embodiments, the CD38 CAR or the TRAIL variant protein are encoded by a polynucleotide that has been inserted in a viral vector. In certain embodiments, the viral vector comprises an adenovirus, an adeno-associated virus, a lentivirus, or a retrovirus. In certain embodiments, the viral vector comprises a lentivirus or a retrovirus. In certain embodiments, the viral vector comprises a lentivirus. In certain embodiments, the viral vector comprises a retrovirus. The viral vector can be used to transduce primary NK cells or an NK cell line. In certain embodiments, the viral vector can be used to transduce primary NK cells. In certain embodiments, the viral vector can be used to transduce an NK cell line. In certain embodiments, the viral vector can be used to transduce NK-92 cells. In certain embodiments, the viral vector can be used to transduce KHYG-1 cells. In certain embodiments, the cells may be transiently transfected using any of the above described methods such as electroporation, a viral vector or, a lipid based transfection reagent compatible with in vivo use.

In certain embodiments, the CD38 CAR or the TRAIL variant protein are encoded by a polynucleotide. In certain embodiments, the polynucleotide is a DNA plasmid or linearized DNA polynucleotide. In certain embodiments, the polynucleotide is an mRNA molecule. Any of these polynucleotides can be introduced into a primary NK cell population or an NK cell line by electroporation. For example, the MaxCyte Flow Electroporation platform can be used to generate the engineered NK cells.

Engineered natural killer cells comprising a deletion or reduced expression of a checkpoint inhibitor receptor may be made using several different techniques known in the art. Receptors can be deleted or reduced using a CRISPR/Cas9 targeting mechanism (using a gRNA targeting nucleotide). gRNA can be transfected into primary NK cells or cell lines. In certain embodiments, gRNA is transfected into primary NK cells, or a population of primary cells, resulting in reduced expression of the checkpoint inhibitory receptor in the population. In certain embodiments, gRNA is transfected into an NK cell line. In certain embodiments, gRNA is transfect into a KHYG-1 cell line, and clones comprising homozygous deletion of a checkpoint inhibitory receptor are selected.

Methods of Administering Natural Killer Cells

This disclosure envisions pharmaceutical compositions comprising formulations of engineered NK cells suitable for intravenous administration to a subject. The pharmaceutical compositions of the present disclosure comprise an NK cell or plurality of NK cells expressing a CAR; optionally the NK cell may include a TRAIL variant or deletion of a checkpoint inhibitor. In certain embodiments, the CAR expressing NK cell is formulated with an acceptable carrier, diluent, or excipient for administration. Such compositions may comprise buffers such as, for example, neutral buffered saline, normal saline, or phosphate buffered saline. In certain embodiments, the pharmaceutical composition may comprise a carbohydrate such as glucose, dextrose, lactose, galactose, mannose, sucrose or mannitol. In certain embodiments, the pharmaceutical compositions comprise a protein, polypeptides, or amino acids such as glycine; In certain embodiments, the pharmaceutical compositions comprise additional stabilizers and preservatives such as antioxidants; chelating agents such as EDTA or EGTA, or glutathione. In certain embodiments, the NK cells are expanded from a frozen stock preserved in glycerol at low temperature, such as below −70° C. In certain embodiments, the NK cells are expanded using cytokines such as Interelukin-2 and interleukin-15, and cultured for a week or more. In certain embodiments, the NK cells are expanded using cytokines such as Interelukin-2 and interleukin-15, and cultured for between about a week and about 3 weeks.

In certain embodiments, the NK cells and cell lines that are administered are gamma irradiated before administration to the individual receiving the cells. In certain embodiments, the cells are irradiated to prevent the cells from growing and dividing in vivo. In certain embodiments, the cells are irradiated at dose of at least 5 Gy, 10 Gy, 20 Gy, 30 Gy, 40 Gy, 50 Gy or more. In certain embodiments, the cells are irradiated at dose of no more than 20 Gy, 30 Gy, 40 Gy, 50 Gy, 60 Gy. In certain embodiments, the cells are treated such that their in vivo half-life is less than about 7, 6, 5, 4, 3, 2, or 1 days. In certain embodiments, the cells and cell lines comprise a suicide gene that expresses a protein that prevents cell division or is toxic to the cells, allowing for a shortened half-life, or for the cells to be killed upon administration of a compound. Examples of common suicide genes include herpes thymidine kinase and inducible Caspase 9. Cells comprising a herpes thymidine kinase can be killed using anti-herpes antivirals such as acyclovir or ganciclovir.

The engineered NK cells that are the subject of this disclosure can be administered in an amount sufficient to prevent the advancement or induce remission of a particular cancer or neoplasm. In certain embodiments, the engineered NK cells are administered in an amount greater than about $1 \times 10^6$ cells/m$^2$, about $1 \times 10^7$ cells/m$^2$, about $1 \times 10^8$ cells/m$^2$, about $1 \times 10^9$ cells/m$^2$, and about $1 \times 10^{10}$ cells/m$^2$. In certain embodiments, the engineered NK cells are administered in an amount between about $1 \times 10^6$ and about $1 \times 10^{10}$ cells/m$^2$. In certain embodiments, the engineered NK cells are administered in an amount between about $1 \times 10^7$ and about $1 \times 10^{10}$ cells/m$^2$. In certain embodiments, the engineered NK cells are administered in an amount between about $1 \times 10^8$ and about $1 \times 10^{10}$ cells/m$^2$. In certain embodiments, the engineered NK cells are administered in an amount between about $1 \times 10^9$ and about $1 \times 10^{10}$ cells/m$^2$. In certain embodiments, the engineered NK cells are administered in an amount between about $1 \times 10^7$ and about $1 \times 10^9$ cells/m$^2$. In certain embodiments, the engineered NK cells are administered in an amount between about $1 \times 10^7$ and about $1 \times 10^8$ cells/m$^2$. In certain embodiments, the engineered NK cells are administered in an amount between about $1 \times 10^8$ and about $1 \times 10^9$ cells/m$^2$. The engineered NK cells can be administered daily, weekly, or monthly. In certain embodiments, cells are administered weekly for two, three, four, five, six, seven, eight, nine, ten, eleven, twelve weeks or more. In certain embodiments, after weekly administration engineered NK cells may be administered monthly for maintenance. The cells can be administered in a manner suitable to the cancer being treated. For example, for a hematological cancer, cells can be administered intravenously. For example, for a solid tissue cancer, cells can be administered intratumoral or intraperitoneally.

Treatment Adjuvants

Administration of a treatment adjuvant before, with, or after administration of an engineered NK cell can increase the efficacy of the treatment. In certain embodiments, the adjuvant comprises interleukin-2 (IL-2), interleukin 8 (IL-8), interleukin-12 (IL-12), interleukin-15 (IL-15), or proteasome inhibitor. In certain embodiments, the proteasome inhibitor is bortezomib, carfilzomib, ixazomib, or a combination thereof. In certain embodiments, any of IL-2, IL-8, IL-12, IL-15, or a proteasome inhibitor can be administered to a patient before administration of an engineered NK cell. In certain embodiments, any of IL-2, IL-8, IL-12, IL-15, or a proteasome inhibitor can be administered to a patient during administration of an engineered NK cell. In certain embodiments, any of IL-2, IL-8, IL-12, IL-15, or a proteasome inhibitor can be administered to a patient after administration of an engineered NK cell. In certain embodiments, the activity of IL-2, IL-8, IL-12, IL-15 can be supplied by a non-interleukin agonist for the IL-2, IL8, IL-12, and IL-15 receptors. For example, an interleukin-12 agonist can be ALT-803 or ALT-801; an interleukin-15 agonist can be NIZ985.

In certain embodiments, the engineered NK cell can be incubated with interleukin-12, interleukin-15, or proteasome inhibitor before administration of the engineered NK cell. In certain embodiments, the CD38 CAR NK cell can be incubated with interleukin-12, interleukin-15, or bortezomib before administration. In certain embodiments, the TRAIL variant NK cell can be incubated with IL-2, IL-8, IL-12, IL-15, or a proteasome inhibitor before administration. In certain embodiments, incubation is for at least 4, 6, 8, 12, or 24 hours. In certain embodiments, incubation is for between about 4 hours and about 48 hours.

The treatment methods of the current disclosure envision the administration of low dose cyclophosphamide as an adjuvant to improve treatment with engineered NK cells. Cyclophosphamide can be administered either orally or intravenously. In certain embodiments, the cyclophosphamide is administered in a metronomic fashion, for example, sustained low doses of cyclophosphamide. In certain embodiments, cyclophosphamide is administered orally at a dose of between about 100 mg to about 25 mg a day or every other day for one, two, three, four, or more weeks. In certain embodiments, cyclophosphamide is administered orally at a dose of about 50 mg a day for one, two, three, four, or more weeks. In certain embodiments, cyclophosphamide is administered intravenously at a dose of between about 1000 mg to about 250 mg a week for one, two, three, four, or more weeks. In certain embodiments, cyclophosphamide is administered intravenously at a dose of about 750 mg, 500 mg, 250 mg or less a week for one, two, three, four, or more weeks. In certain embodiments, the cyclophosphamide is administered before administration of engineered NK cells and discontinued once engineered NK cells are administered. In certain embodiments, the cyclophosphamide is administered to overlap with the administration of engineered NK cells by one, two, three, four, five, or six months. In certain embodiments, the cyclophosphamide is administered simultaneously with administration of engineered NK cells.

The treatment methods of the current disclosure envision the administration of a metalloprotease inhibitor as an adjuvant to improve treatment with engineered NK cells. In certain embodiments, the metalloprotease inhibitor is a tetracycline antibiotic such as, doxycycline, minocycline, tigecycline, demeclocycline, methacycline, chlortetracycline, oxytetracycline, lymecycline, meclocycline, or rolitetracycline. In certain embodiments, the tetracycline antibiotic is doxycycline. In certain embodiments, individuals to be treated with the engineered NK cells of this disclosure are pretreated or concurrently treated with doxycycline at a concentration of between about 50 mg and about 300 mg per day, or at a concentration of between about 100 mg and 200 mg per day. Doxycycline can be administered orally or intravenously. In certain embodiments, individuals can be treated with doxycycline simultaneously with engineered NK cells.

The treatment methods of the current disclosure envision further adjuvants that sensitize cells to killing by engineered NK cells and can be administered to a patient with or separately from the engineered NK cells. For example, a cancer cell may be resistant to TRAIL induced apoptosis. In certain embodiments, the adjuvant is a small molecule that restores sensitivity to TRAIL induced apoptosis. In certain embodiments, the compound is a SMAC mimetic, for example TL32711, LCL161, GDC-0917, HGS1029; an NF-κB inhibitor, for example (−)-DHMEQ, PBS-1086, IT-603, or IT-901; a neddylation inhibitor, for example MLN4924; a histone deacetylase (HDAC) inhibitor, for example panobinostat, vorinostat, romidepsin, chidamide, belinostat, valproic acid, mocetinostat, abexinostat, etinostat, SB939, givinostat, quisinostat, resminostat. Also envisioned is a treatment adjuvant that is an inhibitor of an apoptosis inhibiting protein for example: a BCL-2 inhibitor, for example, venetoclax (ABT-199), or obatoclax (GX15-070); a survivin inhibitor, for example YM15 or shepherdin. In certain embodiments, the adjuvant is administered before administration of the engineered NK cell. In certain embodiments, the adjuvant is administered simultaneously with administration of the engineered NK cell.

Therapeutic Indications

The engineered natural killer cells expressing CD38 CAR of the present disclosure are useful for the therapeutic treatment of cancer. In certain embodiments, the cancer comprises a hematological (blood) cancer. In certain embodiments, the hematological cancer comprises multiple myeloma, smoldering multiple myeloma, or light chain myeloma. In certain embodiments, the hematological cancer is a leukemia. In certain embodiments, the leukemia comprises acute lymphoblastic leukemia, chronic lymphocytic leukemia, acute myelogenous leukemia, chronic myelogenous leukemia, hairy cell leukemia, T-cell prolymphocytic leukemia, or large granular lymphocytic leukemia.

In certain embodiments, the cancer to be treated is a solid tissue tumor. In certain embodiments, the solid tissue tumor is a liver tumor, including hepatocellular carcinoma; a lung tumor; non-small cell lung cancer; a pancreatic tumor, including pancreatic adenocarcinoma or acinar cell carcinoma of the pancreas; a colon cancer; stomach cancer; kidney cancer, including renal cell carcinoma (RCC) and transitional cell carcinoma (TCC, also known as urothelial cell carcinoma); ovarian cancer; prostate cancer; breast cancer; or cervical cancer.

CARs in General

In certain embodiments, described herein, are engineered NK cells. In certain embodiments, the engineered NK cell exhibits a high level of E-selectin ligand. In certain embodiments, the engineered NK cell that exhibits a high level of E-selectin ligand binding exhibits a level of HECA-452 binding greater than that of an NK-92 cell. In certain embodiments, the engineered NK cell comprises a chimeric antigen receptor. In certain embodiments, the engineered NK cell that comprises a chimeric antigen receptor, further comprises a variant human TRAIL molecule. In certain embodiments, the engineered NK cell that comprises a chimeric antigen receptor, further comprises a variant human TRAIL molecule, wherein the variant human TRAIL molecule comprises three amino acid mutations; G131R, N199R, and K201H. In certain embodiments, the engineered NK cell that comprises a chimeric antigen receptor, further comprises a variant human TRAIL molecule, wherein the variant human TRAIL molecule comprises two amino acid mutations; D269H and E195R. In certain embodiments, the engineered NK cell that comprises a chimeric antigen receptor and a variant human TRAIL molecule, further comprises deletion or reduction in expression of a checkpoint inhibitor molecule. In certain embodiments, the engineered NK cell that comprises a chimeric antigen receptor and a variant human TRAIL molecule, further comprises deletion or reduction in expression of CD96 (TACTILE). In certain embodiments, the engineered NK cell that comprises a chimeric antigen receptor and a variant human TRAIL molecule, further comprises deletion or reduction in expression of CD328 (SIGLEC7). In certain embodiments, the engineered NK cell that comprises a chimeric antigen receptor and a variant human TRAIL molecule, further comprises deletion or reduction in expression of CTLA-4. In certain embodiments, the engineered NK cell that comprises a chimeric antigen receptor and a variant human TRAIL molecule, further comprises deletion or reduction in expression of CD279 (PD-1). In certain embodiments, the engineered NK cell that comprises a chimeric antigen receptor and a variant human TRAIL molecule, further comprises deletion or reduction in expression of at least two checkpoint inhibitors selected from CD96 (TACTILE), CD328 (SIGLEC7), CTLA-4, and CD279 (PD-1).

Cancer Associated Antigens

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to a cancer associated antigen. In certain embodiments, the engineered NK cell comprising a chimeric antigen receptor that specifically binds to a cancer associated antigen, further comprises a variant human TRAIL molecule. In certain embodiments, the engineered NK cell comprising a chimeric antigen receptor that specifically binds to a cancer associated antigen, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to a cancer associated antigen, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to a cancer associated antigen and a variant human TRAIL molecule, further comprises deletion or reduction in expression of a checkpoint inhibitor molecule. In certain embodiments, the engineered NK cell comprising a chimeric antigen receptor that specifically binds to a cancer associated antigen and a variant human TRAIL molecule, further comprises deletion or reduction in expression of CD96 (TACTILE). In certain embodiments, the engineered NK cell comprising a chimeric antigen receptor that specifically binds to a cancer associated antigen and a variant human TRAIL molecule, further comprises deletion or reduction in expression of CD328 (SIGLEC7). In certain embodiments, the engineered NK cell comprising a chimeric antigen receptor that specifically binds to a cancer associated antigen, and a variant human TRAIL molecule, further comprises deletion or reduction in expression of CTLA-4. In certain embodiments, the engineered NK cell comprising a chimeric antigen receptor that specifically binds to a cancer associated antigen and a variant human TRAIL molecule, further comprises deletion or reduction in expression of CD279 (PD-1). In certain embodiments, the engineered NK cell comprising a chimeric antigen receptor that specifically binds to a cancer associated antigen and a variant human TRAIL molecule, further comprises deletion or reduction in expression of at least two checkpoint inhibitors selected from CD96 (TACTILE), CD328 (SIGLEC7), CTLA-4, and CD279 (PD-1).

Blood Cancer Associated Antigens

In certain embodiments, described herein, are engineered NK cells. In certain embodiments, the engineered NK cell exhibits a high level of E-selectin ligand. In certain embodiments, the engineered NK cell that exhibits a high level of E-selectin ligand binding exhibits a level of HECA-452 binding greater than that of an NK-92 cell. In certain embodiments, the engineered NK cell comprises a chimeric antigen receptor that specifically binds to a blood cancer associated antigen. In certain embodiments, the engineered NK cell comprising a chimeric antigen receptor that specifically binds to a blood cancer associated antigen, further comprises a variant human TRAIL molecule. In certain embodiments, the engineered NK cell comprising a chimeric antigen receptor that specifically binds to a blood cancer associated antigen, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to a blood cancer associated antigen, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to a blood cancer associated antigen and a variant human TRAIL molecule, further comprises deletion or reduction in expression of a checkpoint inhibitor molecule. In certain embodiments, the engineered NK cell comprising a chimeric antigen receptor that specifically binds to a blood cancer associated antigen and a variant human TRAIL molecule, further comprises deletion or reduction in expression of CD96 (TACTILE). In certain embodiments, the engineered NK cell comprising a chimeric antigen receptor that specifically binds to a blood cancer associated antigen and a variant human TRAIL molecule, further comprises deletion or reduction in expression of CD328 (SIGLEC7). In certain embodiments, the engineered NK cell comprising a chimeric antigen receptor that specifically binds to a blood cancer associated antigen, and a variant human TRAIL molecule, further comprises deletion or reduction in expression of CTLA-4. In certain embodiments, the engineered NK cell comprising a chimeric antigen receptor that specifically binds to a blood cancer associated antigen and a variant human TRAIL molecule, further comprises deletion or reduction in expression of CD279 (PD-1). In certain embodiments, the engineered NK cell comprising a chimeric antigen receptor that specifically binds to a blood cancer associated antigen and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD319

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD319/SLAMF-7. In certain embodiments, the engineered NK cell comprising a chimeric antigen receptor that specifically binds to CD319/SLAMF-7, further comprises a variant human TRAIL molecule. In certain embodiments, the engineered NK cell comprising a chimeric antigen receptor that specifically binds to CD319/SLAMF-7, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD319/SLAMF-7, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD319/SLAMF-7 and a variant human TRAIL molecule, further comprises deletion or reduction in expression of a checkpoint inhibitor molecule. In certain embodiments, the engineered NK cell comprising a chimeric antigen receptor that specifically binds to CD319/SLAMF-7 and a variant human TRAIL molecule, further comprises deletion or reduction in expression of CD96 (TACTILE). In certain embodiments, the engineered NK cell comprising a chimeric antigen receptor that specifically binds to CD319/SLAMF-7 and a variant human TRAIL molecule, further comprises deletion or reduction in expression of CD328 (SIGLEC7). In certain embodiments, the engineered NK cell comprising a chimeric antigen receptor that specifically binds to CD319/SLAMF-7 and a variant human TRAIL molecule, further comprises deletion or reduction in expression of CTLA-4. In certain embodiments, the engineered NK cell comprising a chimeric antigen receptor that specifically binds to CD319/SLAMF-7 and a variant human TRAIL molecule, further comprises deletion or reduction in expression of CD279 (PD-1). In certain embodiments, the engineered NK cell comprising a chimeric antigen receptor that specifically binds to CD319/SLAMF-7 and a variant human TRAIL molecule, further comprises deletion or reduction in expression of at least two checkpoint inhibitors selected from CD96 (TACTILE), CD328 (SIGLEC7), CTLA-4, and CD279 (PD-1).

TNFRSF17

In certain embodiments, described herein, are engineered NK cells. In certain embodiments, the engineered NK cell exhibits a high level of E-selectin ligand. In certain embodiments, the engineered NK cell that exhibits a high level of HECA E-selectin ligand exhibits a level of HECA-452 binding greater than that of an NK-92 cell. In certain embodiments, the engineered NK cell comprises a chimeric antigen receptor that specifically binds to TNFRSF17/BCMA. In certain embodiments, the engineered NK cell comprising a chimeric antigen receptor that specifically binds to TNFRSF17/BCMA, further comprises a variant human TRAIL molecule. In certain embodiments, the engineered NK cell comprising a chimeric antigen receptor that specifically binds to TNFRSF17/BCMA, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to TNFRSF17/BCMA, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to TNFRSF17/BCMA and a variant human TRAIL molecule, further comprises deletion or reduction in expression of a checkpoint inhibitor molecule. In certain embodiments, the engineered NK cell comprising a chimeric antigen receptor that specifically binds to TNFRSF17/BCMA and a variant human TRAIL molecule, further comprises deletion or reduction in expression of CD96 (TACTILE). In certain embodiments, the engineered NK cell comprising a chimeric antigen receptor that specifically binds to TNFRSF17/BCMA and a variant human TRAIL molecule, further comprises deletion or reduction in expression of CD328 (SIGLEC7). In certain embodiments, the engineered NK cell comprising a chimeric antigen receptor that specifically binds to TNFRSF17/BCMA and a variant human TRAIL molecule, further comprises deletion or reduction in expression of CTLA-4. In certain embodiments, the engineered NK cell comprising a chimeric antigen receptor that specifically binds to TNFRSF17/BCMA and a variant human TRAIL molecule, further comprises deletion or reduction in expression of CD279 (PD-1). In certain embodiments, the engineered NK cell comprising a chimeric antigen receptor that specifically binds to TNFRSF17/BCMA and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD123

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD123/IL3-RA. In certain embodiments, the engineered NK cell comprising a chimeric antigen receptor that specifically binds to CD123/IL3-RA, further comprises a variant human TRAIL molecule. In certain embodiments, the engineered NK cell comprising a chimeric antigen receptor that specifically binds to CD123/IL3-RA, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD123/IL3-RA, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD123/IL3-RA and a variant human TRAIL molecule, further comprises deletion or reduction in expression of a checkpoint inhibitor molecule. In certain embodiments, the engineered NK cell comprising a chimeric antigen receptor that specifically binds to CD123/IL3-RA and a variant human TRAIL molecule, further comprises deletion or reduction in expression of CD96 (TACTILE). In certain embodiments, the engineered NK cell comprising a chimeric antigen receptor that specifically binds to CD123/IL3-RA and a variant human TRAIL molecule, further comprises deletion or reduction in expression of CD328 (SIGLEC7). In certain embodiments, the engineered NK cell comprising a chimeric antigen receptor that specifically binds to CD123/IL3-RA and a variant human TRAIL molecule, further comprises deletion or reduction in expression of CTLA-4. In certain embodiments, the engineered NK cell comprising a chimeric antigen receptor that specifically binds to CD123/IL3-RA and a variant human TRAIL molecule, further comprises deletion or reduction in expression of CD279 (PD-1). In certain embodiments, the engineered NK cell comprising a chimeric antigen receptor that specifically binds to CD123/IL3-RA and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD138

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to SYND1/CD138. In certain embodiments, the engineered NK cell comprising a chimeric antigen receptor that specifically binds to SYND1/CD138, further comprises a variant human TRAIL molecule. In certain embodiments, the engineered NK cell comprising a chimeric antigen receptor that specifically binds to SYND1/CD138, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to SYND1/CD138, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to SYND1/CD138 and a variant human TRAIL molecule, further comprises deletion or reduction in expression of a checkpoint inhibitor molecule. In certain embodiments, the engineered NK cell comprising a chimeric antigen receptor that specifically binds to SYND1/CD138 and a variant human TRAIL molecule, further comprises deletion or reduction in expression of CD96 (TACTILE). In certain embodiments, the engineered NK cell comprising a chimeric antigen receptor that specifically binds to SYND1/CD138 and a variant human TRAIL molecule, further comprises deletion or reduction in expression of CD328 (SIGLEC7). In certain embodiments, the engineered NK cell comprising a chimeric antigen receptor that specifically binds to SYND1/CD138 and a variant human TRAIL molecule, further comprises deletion or reduction in expression of CTLA-4. In certain embodiments, the engineered NK cell comprising a chimeric antigen receptor that specifically binds to SYND1/CD138 and a variant human TRAIL molecule, further comprises deletion or reduction in expression of CD279 (PD-1). In certain embodiments, the engineered NK cell comprising a chimeric antigen receptor that specifically binds to SYND1/CD138 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD229

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD229. In certain embodiments, the engineered NK cell comprising a chimeric antigen receptor that specifically binds to CD229, further comprises a variant human TRAIL molecule. In certain embodiments, the engineered NK cell comprising a chimeric antigen receptor that specifically binds to CD229, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD229, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD229 and a variant human TRAIL molecule, further comprises deletion or reduction in expression of a checkpoint inhibitor molecule. In certain embodiments, the engineered NK cell comprising a chimeric antigen receptor that specifically binds to CD229 and a variant human TRAIL molecule, further comprises deletion or reduction in expression of CD96 (TACTILE). In certain embodiments, the engineered NK cell comprising a chimeric antigen receptor that specifically binds to CD229 and a variant human TRAIL molecule, further comprises deletion or reduction in expression of CD328 (SIGLEC7). In certain embodiments, the engineered NK cell comprising a chimeric antigen receptor that specifically binds to CD229 and a variant human TRAIL molecule, further comprises deletion or reduction in expression of CTLA-4. In certain embodiments, the engineered NK cell comprising a chimeric antigen receptor that specifically binds to CD229 and a variant human TRAIL molecule, further comprises deletion or reduction in expression of CD279 (PD-1). In certain embodiments, the engineered NK cell comprising a chimeric antigen receptor that specifically binds to CD229 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD47

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD47. In certain embodiments, the engineered NK cell comprising a chimeric antigen receptor that specifically binds to CD47, further comprises a variant human TRAIL molecule. In certain embodiments, the engineered NK cell comprising a chimeric antigen receptor that specifically binds to CD47, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD47, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD47 and a variant human TRAIL molecule, further comprises deletion or reduction in expression of a checkpoint inhibitor molecule. In certain embodiments, the engineered NK cell comprising a chimeric antigen receptor that specifically binds to CD47 and a variant human TRAIL molecule, further comprises deletion or reduction in expression of CD96 (TACTILE). In certain embodiments, the engineered NK cell comprising a chimeric antigen receptor that specifically binds to CD47 and a variant human TRAIL molecule, further comprises deletion or reduction in expression of CD328 (SIGLEC7). In certain embodiments, the engineered NK cell comprising a chimeric antigen receptor that specifically binds to CD47 and a variant human TRAIL molecule, further comprises deletion or reduction in expression of CTLA-4. In certain embodiments, the engineered NK cell comprising a chimeric antigen receptor that specifically binds to CD47 and a variant human TRAIL molecule, further comprises deletion or reduction in expression of CD279 (PD-1). In certain embodiments, the engineered NK cell comprising a chimeric antigen receptor that specifically binds to CD47 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD20

In certain embodiments, described herein, are engineered NK cells. In certain embodiments, the engineered NK cell exhibits a high level of E-selectin ligand binding. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD20. In certain embodiments, the engineered NK cell comprising a chimeric antigen receptor that specifically binds to CD20, further comprises a variant human TRAIL molecule. In certain embodiments, the engineered NK cell comprising a chimeric antigen receptor that specifically binds to CD20, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD20, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD20 and a variant human TRAIL molecule, further comprises deletion or reduction in expression of a checkpoint inhibitor molecule. In certain embodiments, the engineered NK cell comprising a chimeric antigen receptor that specifically binds to CD20 and a variant human TRAIL molecule, further comprises deletion or reduction in expression of CD96 (TACTILE). In certain embodiments, the engineered NK cell comprising a chimeric antigen receptor that specifically binds to CD20 and a variant human TRAIL molecule, further comprises deletion or reduction in expression of CD328 (SIGLEC7). In certain embodiments, the engineered NK cell comprising a chimeric antigen receptor that specifically binds to CD20 and a variant human TRAIL molecule, further comprises deletion or reduction in expression of CTLA-4. In certain embodiments, the engineered NK cell comprising a chimeric antigen receptor that specifically binds to CD20 and a variant human TRAIL molecule, further comprises deletion or reduction in expression of CD279 (PD-1). In certain embodiments, the engineered NK cell comprising a chimeric antigen receptor that specifically binds to CD20 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD19

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD19. In certain embodiments, the engineered NK cell comprising a chimeric antigen receptor that specifically binds to CD19, further comprises a variant human TRAIL molecule. In certain embodiments, the engineered NK cell comprising a chimeric antigen receptor that specifically binds to CD19, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD19, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD19 and a variant human TRAIL molecule, further comprises deletion or reduction in expression of a checkpoint inhibitor molecule. In certain embodiments, the engineered NK cell comprising a chimeric antigen receptor that specifically binds to CD19 and a variant human TRAIL molecule, further comprises deletion or reduction in expression of CD96 (TACTILE). In certain embodiments, the engineered NK cell comprising a chimeric antigen receptor that specifically binds to CD19 and a variant human TRAIL molecule, further comprises deletion or reduction in expression of CD328 (SIGLEC7). In certain embodiments, the engineered NK cell comprising a chimeric antigen receptor that specifically binds to CD19 and a variant human TRAIL molecule, further comprises deletion or reduction in expression of CTLA-4. In certain embodiments, the engineered NK cell comprising a chimeric antigen receptor that specifically binds to CD19 and a variant human TRAIL molecule, further comprises deletion or reduction in expression of CD279 (PD-1). In certain embodiments, the engineered NK cell comprising a chimeric antigen receptor that specifically binds to CD19 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD22

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD22. In certain embodiments, the engineered NK cell comprising a chimeric antigen receptor that specifically binds to CD22, further comprises a variant human TRAIL molecule. In certain embodiments, the engineered NK cell comprising a chimeric antigen receptor that specifically binds to CD22, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD22, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD22 and a variant human TRAIL molecule, further comprises deletion or reduction in expression of a checkpoint inhibitor molecule. In certain embodiments, the engineered NK cell comprising a chimeric antigen receptor that specifically binds to CD22 and a variant human TRAIL molecule, further comprises deletion or reduction in expression of CD96 (TACTILE). In certain embodiments, the engineered NK cell comprising a chimeric antigen receptor that specifically binds to CD22 and a variant human TRAIL molecule, further comprises deletion or reduction in expression of CD328 (SIGLEC7). In certain embodiments, the engineered NK cell comprising a chimeric antigen receptor that specifically binds to CD22 and a variant human TRAIL molecule, further comprises deletion or reduction in expression of CTLA-4. In certain embodiments, the engineered NK cell comprising a chimeric antigen receptor that specifically binds to CD22 and a variant human TRAIL molecule, further comprises deletion or reduction in expression of CD279 (PD-1). In certain embodiments, the engineered NK cell comprising a chimeric antigen receptor that specifically binds to CD22 and a variant human TRAIL molecule, further comprises deletion or reduction in expression of at least two checkpoint inhibitors selected from CD96 (TACTILE), CD328 (SIGLEC7), CTLA-4, and CD279 (PD-1).

MUC1

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to MUC1. In certain embodiments, the engineered NK cell comprising a chimeric antigen receptor that specifically binds to MUC1, further comprises a variant human TRAIL molecule. In certain embodiments, the engineered NK cell comprising a chimeric antigen receptor that specifically binds to MUC1, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to MUC1, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to MUC1 and a variant human TRAIL molecule, further comprises deletion or reduction in expression of a checkpoint inhibitor molecule. In certain embodiments, the engineered NK cell comprising a chimeric antigen receptor that specifically binds to MUC1 and a variant human TRAIL molecule, further comprises deletion or reduction in expression of CD96 (TACTILE). In certain embodiments, the engineered NK cell comprising a chimeric antigen receptor that specifically binds to MUC1 and a variant human TRAIL molecule, further comprises deletion or reduction in expression of CD328 (SIGLEC7). In certain embodiments, the engineered NK cell comprising a chimeric antigen receptor that specifically binds to MUC1 and a variant human TRAIL molecule, further comprises deletion or reduction in expression of CTLA-4. In certain embodiments, the engineered NK cell comprising a chimeric antigen receptor that specifically binds to MUC1 and a variant human TRAIL molecule, further comprises deletion or reduction in expression of CD279 (PD-1). In certain embodiments, the engineered NK cell comprising a chimeric antigen receptor that specifically binds to MUC1 and a variant human TRAIL molecule, further comprises deletion or reduction in expression of at least two checkpoint inhibitors selected from CD96 (TACTILE), CD328 (SIGLEC7), CTLA-4, and CD279 (PD-1).

MUC16

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to MUC16. In certain embodiments, the engineered NK cell comprising a chimeric antigen receptor that specifically binds to MUC16, further comprises a variant human TRAIL molecule. In certain embodiments, the engineered NK cell comprising a chimeric antigen receptor that specifically binds to MUC16, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to MUC16, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to MUC16 and a variant human TRAIL molecule, further comprises deletion or reduction in expression of a checkpoint inhibitor molecule. In certain embodiments, the engineered NK cell comprising a chimeric antigen receptor that specifically binds to MUC16 and a variant human TRAIL molecule, further comprises deletion or reduction in expression of CD96 (TACTILE). In certain embodiments, the engineered NK cell comprising a chimeric antigen receptor that specifically binds to MUC16 and a variant human TRAIL molecule, further comprises deletion or reduction in expression of CD328 (SIGLEC7). In certain embodiments, the engineered NK cell comprising a chimeric antigen receptor that specifically binds to MUC16 and a variant human TRAIL molecule, further comprises deletion or reduction in expression of CTLA-4. In certain embodiments, the engineered NK cell comprising a chimeric antigen receptor that specifically binds to MUC16 and a variant human TRAIL molecule, further comprises deletion or reduction in expression of CD279 (PD-1). In certain embodiments, the engineered NK cell comprising a chimeric antigen receptor that specifically binds to MUC16 and a variant human TRAIL molecule, further comprises deletion or reduction in expression of at least two checkpoint inhibitors selected from CD96 (TACTILE), CD328 (SIGLEC7), CTLA-4, and CD279 (PD-1).

Her2/Neu

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to Her2/Neu. In certain embodiments, the engineered NK cell comprising a chimeric antigen receptor that specifically binds to Her2/Neu, further comprises a variant human TRAIL molecule. In certain embodiments, the engineered NK cell comprising a chimeric antigen receptor that specifically binds to Her2/Neu, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to Her2/Neu, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to Her2/Neu and a variant human TRAIL molecule, further comprises deletion or reduction in expression of a checkpoint inhibitor molecule. In certain embodiments, the engineered NK cell comprising a chimeric antigen receptor that specifically binds to Her2/Neu and a variant human TRAIL molecule, further comprises deletion or reduction in expression of CD96 (TACTILE). In certain embodiments, the engineered NK cell comprising a chimeric antigen receptor that specifically binds to Her2/Neu and a variant human TRAIL molecule, further comprises deletion or reduction in expression of CD328 (SIGLEC7). In certain embodiments, the engineered NK cell comprising a chimeric antigen receptor that specifically binds to Her2/Neu and a variant human TRAIL molecule, further comprises deletion or reduction in expression of CTLA-4. In certain embodiments, the engineered NK cell comprising a chimeric antigen receptor that specifically binds to Her2/Neu and a variant human TRAIL molecule, further comprises deletion or reduction in expression of CD279 (PD-1). In certain embodiments, the engineered NK cell comprising a chimeric antigen receptor that specifically binds to Her2/Neu and a variant human TRAIL molecule, further comprises deletion or reduction in expression of at least two checkpoint inhibitors selected from CD96 (TACTILE), CD328 (SIGLEC7), CTLA-4, and CD279 (PD-1).

Epidermal Growth Factor Receptor (EGFR)

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to EGFR. In certain embodiments, the engineered NK cell comprising a chimeric antigen receptor that specifically binds to EGFR, further comprises a variant human TRAIL molecule. In certain embodiments, the engineered NK cell comprising a chimeric antigen receptor that specifically binds to EGFR, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to EGFR, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to EGFR and a variant human TRAIL molecule, further comprises deletion or reduction in expression of a checkpoint inhibitor molecule. In certain embodiments, the engineered NK cell comprising a chimeric antigen receptor that specifically binds to EGFR and a variant human TRAIL molecule, further comprises deletion or reduction in expression of CD96 (TACTILE). In certain embodiments, the engineered NK cell comprising a chimeric antigen receptor that specifically binds to EGFR and a variant human TRAIL molecule, further comprises deletion or reduction in expression of CD328 (SIGLEC7). In certain embodiments, the engineered NK cell comprising a chimeric antigen receptor that specifically binds to EGFR and a variant human TRAIL molecule, further comprises deletion or reduction in expression of CTLA-4. In certain embodiments, the engineered NK cell comprising a chimeric antigen receptor that specifically binds to EGFR and a variant human TRAIL molecule, further comprises deletion or reduction in expression of CD279 (PD-1). In certain embodiments, the engineered NK cell comprising a chimeric antigen receptor that specifically binds to EGFR and a variant human TRAIL molecule, further comprises deletion or reduction in expression of at least two checkpoint inhibitors selected from CD96 (TACTILE), CD328 (SIGLEC7), CTLA-4, and CD279 (PD-1).

Mesothelin

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to Mesothelin. In certain embodiments, the engineered NK cell comprising a chimeric antigen receptor that specifically binds to Mesothelin, further comprises a variant human TRAIL molecule. In certain embodiments, the engineered NK cell comprising a chimeric antigen receptor that specifically binds to Mesothelin, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to Mesothelin, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to Mesothelin and a variant human TRAIL molecule, further comprises deletion or reduction in expression of a checkpoint inhibitor molecule. In certain embodiments, the engineered NK cell comprising a chimeric antigen receptor that specifically binds to Mesothelin and a variant human TRAIL molecule, further comprises deletion or reduction in expression of CD96 (TACTILE). In certain embodiments, the engineered NK cell comprising a chimeric antigen receptor that specifically binds to Mesothelin and a variant human TRAIL molecule, further comprises deletion or reduction in expression of CD328 (SIGLEC7). In certain embodiments, the engineered NK cell comprising a chimeric antigen receptor that specifically binds to Mesothelin and a variant human TRAIL molecule, further comprises deletion or reduction in expression of CTLA-4. In certain embodiments, the engineered NK cell comprising a chimeric antigen receptor that specifically binds to Mesothelin and a variant human TRAIL molecule, further comprises deletion or reduction in expression of CD279 (PD-1). In certain embodiments, the engineered NK cell comprising a chimeric antigen receptor that specifically binds to Mesothelin and a variant human TRAIL molecule, further comprises deletion or reduction in expression of at least two checkpoint inhibitors selected from CD96 (TACTILE), CD328 (SIGLEC7), CTLA-4, and CD279 (PD-1).

CLL-1

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CLL-1. In certain embodiments, the engineered NK cell comprising a chimeric antigen receptor that specifically binds to CLL-1, further comprises a variant human TRAIL molecule. In certain embodiments, the engineered NK cell comprising a chimeric antigen receptor that specifically binds to CLL-1, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CLL-1, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CLL-1 and a variant human TRAIL molecule, further comprises deletion or reduction in expression of a checkpoint inhibitor molecule. In certain embodiments, the engineered NK cell comprising a chimeric antigen receptor that specifically binds to CLL-1 and a variant human TRAIL molecule, further comprises deletion or reduction in expression of CD96 (TACTILE). In certain embodiments, the engineered NK cell comprising a chimeric antigen receptor that specifically binds to CLL-1 and a variant human TRAIL molecule, further comprises deletion or reduction in expression of CD328 (SIGLEC7). In certain embodiments, the engineered NK cell comprising a chimeric antigen receptor that specifically binds to CLL-1 and a variant human TRAIL molecule, further comprises deletion or reduction in expression of CTLA-4. In certain embodiments, the engineered NK cell comprising a chimeric antigen receptor that specifically binds to CLL-1 and a variant human TRAIL molecule, further comprises deletion or reduction in expression of CD279 (PD-1). In certain embodiments, the engineered NK cell comprising a chimeric antigen receptor that specifically binds to CLL-1 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD38

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD38. In certain embodiments, the engineered NK cell comprising a chimeric antigen receptor that specifically binds to CD38, further comprises a variant human TRAIL molecule. In certain embodiments, the engineered NK cell comprising a chimeric antigen receptor that specifically binds to CD38, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD38, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD38 and a variant human TRAIL molecule, further comprises deletion or reduction in expression of a checkpoint inhibitor molecule. In certain embodiments, the engineered NK cell comprising a chimeric antigen receptor that specifically binds to CD38 and a variant human TRAIL molecule, further comprises deletion or reduction in expression of CD96 (TACTILE). In certain embodiments, the engineered NK cell comprising a chimeric antigen receptor that specifically binds to CD38 and a variant human TRAIL molecule, further comprises deletion or reduction in expression of CD328 (SIGLEC7). In certain embodiments, the engineered NK cell comprising a chimeric antigen receptor that specifically binds to CD38 and a variant human TRAIL molecule, further comprises deletion or reduction in expression of CTLA-4. In certain embodiments, the engineered NK cell comprising a chimeric antigen receptor that specifically binds to CD38 and a variant human TRAIL molecule, further comprises deletion or reduction in expression of CD279 (PD-1). In certain embodiments, the engineered NK cell comprising a chimeric antigen receptor that specifically binds to CD38 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD38 (SEQ ID NO: 1 and 2)

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD38. In certain embodiments, the engineered NK cell that comprises a chimeric antigen receptor that specifically binds to CD38 comprises a CAR targeting domain comprising an amino acid sequence at least 90% identical to that set forth in SEQ ID NO: 1, and an amino acid sequence at least 90% identical to that set forth in SEQ ID NO: 2. In certain embodiments, the engineered NK cell that comprises a chimeric antigen receptor that specifically binds to CD38 comprises a CAR targeting domain comprising an amino acid sequence at least 95% identical to that set forth in SEQ ID NO: 1, and an amino acid sequence at least 95% identical to that set forth in SEQ ID NO: 2. In certain embodiments, the engineered NK cell that comprises a chimeric antigen receptor that specifically binds to CD38 comprises a CAR targeting domain comprising an amino acid sequence at least 98% identical to that set forth in SEQ ID NO: 1, and an amino acid sequence at least 98% identical to that set forth in SEQ ID NO: 2. In certain embodiments, the engineered NK cell that comprises a chimeric antigen receptor that specifically binds to CD38 comprises a CAR targeting domain comprising an amino acid sequence identical to that set forth in SEQ ID NO: 1, and an amino acid sequence identical to that set forth in SEQ ID NO: 2. In certain embodiments, the engineered NK cell that comprises a chimeric antigen receptor that specifically binds to CD38 comprises a CAR targeting domain comprising an amino acid sequence identical to that set forth in SEQ ID NO: 1, and an amino acid sequence identical to that set forth in SEQ ID NO: 2. In certain embodiments, the engineered NK cell comprising a chimeric antigen receptor that specifically binds to CD38, further comprises a variant human TRAIL molecule. In certain embodiments, the engineered NK cell comprising a chimeric antigen receptor that specifically binds to CD38, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD38, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD38 and a variant human TRAIL molecule, further comprises deletion or reduction in expression of a checkpoint inhibitor molecule. In certain embodiments, the engineered NK cell comprising a chimeric antigen receptor that specifically binds to CD38 and a variant human TRAIL molecule, further comprises deletion or reduction in expression of CD96 (TACTILE). In certain embodiments, the engineered NK cell comprising a chimeric antigen receptor that specifically binds to CD38 and a variant human TRAIL molecule, further comprises deletion or reduction in expression of CD328 (SIGLEC7). In certain embodiments, the engineered NK cell comprising a chimeric antigen receptor that specifically binds to CD38 and a variant human TRAIL molecule, further comprises deletion or reduction in expression of CTLA-4. In certain embodiments, the engineered NK cell comprising a chimeric antigen receptor that specifically binds to CD38 and a variant human TRAIL molecule, further comprises deletion or reduction in expression of CD279 (PD-1). In certain embodiments, the engineered NK cell comprising a chimeric antigen receptor that specifically binds to CD38 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD38 (SEQ ID NO: 3 and 4)

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD38. In certain embodiments, the engineered NK cell that comprises a chimeric antigen receptor that specifically binds to CD38 comprises a CAR targeting domain comprising an amino acid sequence at least 90% identical to that set forth in SEQ ID NO: 3, and an amino acid sequence at least 90% identical to that set forth in SEQ ID NO: 4. In certain embodiments, the engineered NK cell that comprises a chimeric antigen receptor that specifically binds to CD38 comprises a CAR targeting domain comprising an amino acid sequence at least 95% identical to that set forth in SEQ ID NO: 3, and an amino acid sequence at least 95% identical to that set forth in SEQ ID NO: 4. In certain embodiments, the engineered NK cell that comprises a chimeric antigen receptor that specifically binds to CD38 comprises a CAR targeting domain comprising an amino acid sequence at least 98% identical to that set forth in SEQ ID NO: 3, and an amino acid sequence at least 98% identical to that set forth in SEQ ID NO: 4. In certain embodiments, the engineered NK cell that comprises a chimeric antigen receptor that specifically binds to CD38 comprises a CAR targeting domain comprising an amino acid sequence identical to that set forth in SEQ ID NO: 3, and an amino acid sequence identical to that set forth in SEQ ID NO: 4. In certain embodiments, the engineered NK cell that comprises a chimeric antigen receptor that specifically binds to CD38 comprises a CAR targeting domain comprising an amino acid sequence identical to that set forth in SEQ ID NO: 3, and an amino acid sequence identical to that set forth in SEQ ID NO: 4. In certain embodiments, the engineered NK cell comprising a chimeric antigen receptor that specifically binds to CD38, further comprises a variant human TRAIL molecule. In certain embodiments, the engineered NK cell comprising a chimeric antigen receptor that specifically binds to CD38, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD38, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD38 and a variant human TRAIL molecule, further comprises deletion or reduction in expression of a checkpoint inhibitor molecule. In certain embodiments, the engineered NK cell comprising a chimeric antigen receptor that specifically binds to CD38 and a variant human TRAIL molecule, further comprises deletion or reduction in expression of CD96 (TACTILE). In certain embodiments, the engineered NK cell comprising a chimeric antigen receptor that specifically binds to CD38 and a variant human TRAIL molecule, further comprises deletion or reduction in expression of CD328 (SIGLEC7). In certain embodiments, the engineered NK cell comprising a chimeric antigen receptor that specifically binds to CD38 and a variant human TRAIL molecule, further comprises deletion or reduction in expression of CTLA-4. In certain embodiments, the engineered NK cell comprising a chimeric antigen receptor that specifically binds to CD38 and a variant human TRAIL molecule, further comprises deletion or reduction in expression of CD279 (PD-1). In certain embodiments, the engineered NK cell comprising a chimeric antigen receptor that specifically binds to CD38 and a variant human TRAIL molecule, further comprises deletion or reduction in expression of at least two checkpoint inhibitors selected from CD96 (TACTILE), CD328 (SIGLEC7), CTLA-4, and CD279 (PD-1).

CD38 (SEQ ID NO: 5 and 6)

In certain embodiments, described herein, are engineered NK cells. In certain embodiments, the engineered NK cell exhibits a high level of E-selectin ligand. In certain embodiments, the engineered NK cell that exhibits a high level of E-selectin ligand exhibits a level of HECA-452 binding greater than that of an NK-92 cell. In certain embodiments, the engineered NK cell comprises a chimeric antigen receptor that specifically binds to CD38. In certain embodiments, the engineered NK cell that comprises a chimeric antigen receptor that specifically binds to CD38 comprises a CAR targeting domain comprising an amino acid sequence at least 90% identical to that set forth in SEQ ID NO: 5, and an amino acid sequence at least 90% identical to that set forth in SEQ ID NO: 6. In certain embodiments, the engineered NK cell that comprises a chimeric antigen receptor that specifically binds to CD38 comprises a CAR targeting domain comprising an amino acid sequence at least 95% identical to that set forth in SEQ ID NO: 5, and an amino acid sequence at least 95% identical to that set forth in SEQ ID NO: 6. In certain embodiments, the engineered NK cell that comprises a chimeric antigen receptor that specifically binds to CD38 comprises a CAR targeting domain comprising an amino acid sequence at least 98% identical to that set forth in SEQ ID NO: 5, and an amino acid sequence at least 98% identical to that set forth in SEQ ID NO: 6. In certain embodiments, the engineered NK cell that comprises a chimeric antigen receptor that specifically binds to CD38 comprises a CAR targeting domain comprising an amino acid sequence identical to that set forth in SEQ ID NO: 5, and an amino acid sequence identical to that set forth in SEQ ID NO: 6. In certain embodiments, the engineered NK cell that comprises a chimeric antigen receptor that specifically binds to CD38 comprises a CAR targeting domain comprising an amino acid sequence identical to that set forth in SEQ ID NO: 5, and an amino acid sequence identical to that set forth in SEQ ID NO: 6. In certain embodiments, the engineered NK cell comprising a chimeric antigen receptor that specifically binds to CD38, further comprises a variant human TRAIL molecule. In certain embodiments, the engineered NK cell comprising a chimeric antigen receptor that specifically binds to CD38, further comprises a variant human TRAIL molecule, wherein the variant human TRAIL molecule comprises three amino acid mutations; G131R, N199R, and K201H. In certain embodiments, the engineered NK cell comprising a chimeric antigen receptor that specifically binds to CD38, further comprises a variant human TRAIL molecule, wherein the variant human TRAIL molecule comprises two amino acid mutations; D269H and E195R. In certain embodiments, the engineered NK cell comprising a chimeric antigen receptor that specifically binds to CD38 and a variant human TRAIL molecule, further comprises deletion or reduction in expression of a checkpoint inhibitor molecule. In certain embodiments, the engineered NK cell comprising a chimeric antigen receptor that specifically binds to CD38 and a variant human TRAIL molecule, further comprises deletion or reduction in expression of CD96 (TACTILE). In certain embodiments, the engineered NK cell comprising a chimeric antigen receptor that specifically binds to CD38 and a variant human TRAIL molecule, further comprises deletion or reduction in expression of CD328 (SIGLEC7). In certain embodiments, the engineered NK cell comprising a chimeric antigen receptor that specifically binds to CD38 and a variant human TRAIL molecule, further comprises deletion or reduction in expression of CTLA-4. In certain embodiments, the engineered NK cell comprising a chimeric antigen receptor that specifically binds to CD38 and a variant human TRAIL molecule, further comprises deletion or reduction in expression of CD279 (PD-1). In certain embodiments, the engineered NK cell comprising a chimeric antigen receptor that specifically binds to CD38 and a variant human TRAIL molecule, further comprises deletion or reduction in expression of at least two checkpoint inhibitors selected from CD96 (TACTILE), CD328 (SIGLEC7), CTLA-4, and CD279 (PD-1).

Further embodiments of the invention are as follows:

1. A pharmaceutical composition comprising an engineered natural killer cell, wherein the engineered natural killer cell exhibits a high level of cell-surface expression of E-selectin ligand, wherein the engineered natural killer cell comprises a chimeric antigen receptor (CAR).

2. The pharmaceutical composition of embodiment 1, wherein the engineered natural killer cell comprises a plurality of engineered natural killer cells that are greater than 25% positive for an antigen bound by the HECA-452 antibody.

3. The pharmaceutical composition of embodiment 1, wherein the engineered natural killer cell exhibits a low level of cell-surface expression of a TRAIL receptor, wherein the TRAIL receptor comprises TNFRSF10A (DR4) or TNFRSF10B (DR5).

4. The pharmaceutical composition of any one of embodiments 1 to 3, wherein the engineered natural killer cell comprises a primary natural killer cell.

5. The pharmaceutical composition of any one of embodiments 1 to 3, wherein the engineered natural killer cell comprises a transformed natural killer cell line.

6. The pharmaceutical composition of embodiment 5, wherein the transformed natural killer cell line is an NK-92 cell line or a KHYG-1 cell line.

7. The pharmaceutical composition of embodiment 5, wherein the transformed natural killer cell line is a KHYG-1 cell line.

8. The pharmaceutical composition of any one of embodiments 1 to 7, wherein the CAR specifically binds a cancer associated antigen.

9. The pharmaceutical composition of embodiment 8, wherein the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEUSGC, NeuGcGM3, GD2, CLL-1, or HERV-K.

10. The pharmaceutical composition of embodiment 8, wherein the cancer associated antigen comprises a blood cancer associated antigen.

11. The pharmaceutical composition of embodiment 10, wherein the blood cancer associated antigen comprises CD38, CD319/SLAMF-7, TNFRSF17/BCMA, SYND1/CD138, CD229, CD47, CD123/IL3-RA, CD19, CD20, CD22, or CLL-1.

12. The pharmaceutical composition of embodiment 10, wherein the blood cancer associated antigen comprises CD38.

13. The pharmaceutical composition of embodiment 12, wherein the CAR comprises a targeting domain amino acid sequence that is at least 80% identical to that set forth in any one of SEQ ID NOs: 1-6.

14. The pharmaceutical composition of embodiment 12, wherein the CAR comprises a targeting domain amino acid sequence that is at least 90% identical to that set forth in any one of SEQ ID NOs: 1-6.

15. The pharmaceutical composition of embodiment 12, wherein the CAR comprises a targeting domain amino acid sequence that is at least 95% identical to that set forth in any one of SEQ ID NOs: 1-6.

16. The pharmaceutical composition of embodiment 12, wherein the CAR comprises a targeting domain amino acid sequence that is at least 98% identical to that set forth in any one of SEQ ID NOs: 1-6.

17. The pharmaceutical composition of embodiment 12, wherein the CAR comprises a targeting domain amino acid sequence that is at least identical to that set forth in any one of SEQ ID NOs: 1-6.

18. The pharmaceutical composition of embodiment 12, wherein the CAR comprises a targeting domain amino acid sequence that is at least 90% identical to that set forth in SEQ ID NOs: 1 and 2.

19. The pharmaceutical composition of embodiment 12, wherein the CAR comprises a targeting domain amino acid sequence that is at least 95% identical to that set forth in SEQ ID NOs: 1 and 2.

20. The pharmaceutical composition of embodiment 12, wherein the CAR comprises a targeting domain amino acid sequence that is at least 98% identical to that set forth in SEQ ID NOs: 1 and 2.

21. The pharmaceutical composition of embodiment 12, wherein the CAR comprises a targeting domain amino acid sequence that is identical to that set forth in SEQ ID NOs: 1 and 2.

22. The pharmaceutical composition of embodiment 12, wherein the CAR comprises a targeting domain amino acid sequence that is at least 90% identical to that set forth in SEQ ID NOs: 3 and 4.

23. The pharmaceutical composition of embodiment 12, wherein the CAR comprises a targeting domain amino acid sequence that is at least 95% identical to that set forth in SEQ ID NOs: 3 and 4.

24. The pharmaceutical composition of embodiment 12, wherein the CAR comprises a targeting domain amino acid sequence that is at least 98% identical to that set forth in SEQ ID NOs: 3 and 4.

25. The pharmaceutical composition of embodiment 12, wherein the CAR comprises a targeting domain amino acid sequence that is identical to that set forth in SEQ ID NOs: 3 and 4.

26. The pharmaceutical composition of embodiment 12, wherein the CAR comprises a targeting domain amino acid sequence that is at least 90% identical to that set forth in SEQ ID NOs: 5 and 6.

27. The pharmaceutical composition of embodiment 12, wherein the CAR comprises a targeting domain amino acid sequence that is at least 95% identical to that set forth in SEQ ID NOs: 5 and 6.

28. The pharmaceutical composition of embodiment 12, wherein the CAR comprises a targeting domain amino acid sequence that is at least 98% identical to that set forth in SEQ ID NOs: 5 and 6.

29. The pharmaceutical composition of embodiment 12, wherein the CAR comprises a targeting domain amino acid sequence that is identical to that set forth in SEQ ID NOs: 5 and 6.

30. The pharmaceutical composition of any one of embodiments 1 to 29, wherein the CAR comprises a transmembrane domain derived from a human CD8 alpha protein.

31. The pharmaceutical composition of any one of embodiments 1 to 30, wherein the CAR comprises a DAP10, DAP12, 2B4 (CD244), or human 4-1BB protein.

32. The pharmaceutical composition of any one of embodiments 1 to 31, wherein the CAR comprises a human 4-1BB protein.

33. The pharmaceutical composition of any one of embodiments 1 to 32, wherein the CAR comprises a human CD3 zeta protein.

34. The pharmaceutical composition of any one of embodiments 1 to 33, wherein the CAR comprises a targeting domain that is derived from an antibody that exhibits a lower affinity for CD38 than Daratumumab.

35. The pharmaceutical composition of any one of embodiments 1 to 34, further comprising a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

36. The pharmaceutical composition of any one of embodiments 1 to 35, further comprising a mutant TNF-related apoptosis-inducing ligand (TRAIL) polypeptide, wherein the mutant TRAIL polypeptide induces increased signaling or possesses increased binding affinity to a TRAIL ligand.

37. The pharmaceutical composition of embodiment 36, wherein the TRAIL ligand comprises TNFRSF10A (DR4) or TNFRSF10B (DR5).

38. The pharmaceutical composition of embodiment 36, wherein the mutant TRAIL polypeptide comprises a D269H/E195R mutation of human TRAIL.

39. The pharmaceutical composition of embodiment 36, wherein the mutant TRAIL polypeptide comprises a G131R/N199R/K201H mutation of human TRAIL.

40. The pharmaceutical composition of any one of embodiments 1 to 39, wherein the CAR or the mutant TRAIL polypeptide is integrated into the genome of the engineered natural killer cell.

41. The pharmaceutical composition of any one of embodiments 1 to 40, wherein the engineered natural killer cell further comprises a deletion or reduction in activity of a checkpoint inhibitory receptor.

42. The pharmaceutical composition of embodiment 41, wherein the checkpoint inhibitory receptor comprises CD85d, CD85j, CD96, CD152, CD159a, CD223, CD279, CD328, SIGLEC9, TIGIT or TIM-3.

43. The pharmaceutical composition of embodiment 42, wherein the checkpoint inhibitory receptor comprises CD96, CD152, or CD328.

44. The pharmaceutical composition of embodiment 42, wherein the checkpoint inhibitory receptor comprises CD96.

45. The pharmaceutical composition of embodiment 42, wherein the checkpoint inhibitory receptor comprises CD152

46. The pharmaceutical composition of embodiment 42, wherein the checkpoint inhibitory receptor comprises CD328.

47. The pharmaceutical composition of any one of embodiments 41 to 46, wherein the checkpoint inhibitory receptor is deleted in whole or in part from the engineered natural killer cell genome, or is disrupted by insertion or deletion of one or more nucleotides at the chromosomal level.

48. The pharmaceutical composition of any one of embodiments 41 to 46, wherein the engineered natural killer cell comprises an siRNA that targets a checkpoint inhibitory receptor.

49. The pharmaceutical composition of any one of embodiments 1 to 48, further comprising a pharmaceutically acceptable carrier, stabilizer, or excipient.

50. The pharmaceutical composition of embodiment 49, wherein the pharmaceutical composition is formulated for intraperitoneal administration.

51. The pharmaceutical composition of embodiment 49, formulated for intravenous administration.
52. The pharmaceutical composition of any one of embodiments 1 to 51, for use in treating cancer.
53. The pharmaceutical composition of embodiment 52, wherein the cancer comprises a leukemia, a lymphoma, or a myeloma.
54. The pharmaceutical composition of embodiment 52, wherein the cancer comprises multiple myeloma.
55. A method of treating a subject with cancer comprising administering to the subject a pharmaceutical composition comprising an engineered natural killer cell, wherein the engineered natural killer cell exhibits a high level of cell-surface expression of E-selectin ligand, wherein the engineered natural killer cell comprises a chimeric antigen receptor (CAR).
56. The method of embodiment 55, wherein the engineered natural killer cell comprises a plurality of engineered natural killer cells that are greater than 25% positive for an antigen bound by the HECA-452 antibody.
57. The method of embodiment 55, wherein the engineered natural killer cell exhibits a low level of cell-surface expression of a TRAIL receptor, wherein the TRAIL receptor comprises TNFRSF10A (DR4) or TNFRSF10B (DR5).
58. The method of any one of embodiments 55 to 57, wherein the engineered natural killer cell comprises a primary natural killer cell.
59. The method of any one of embodiments 55 to 57, wherein the engineered natural killer cell comprises a transformed natural killer cell line.
60. The method of embodiment 59, wherein the transformed natural killer cell line is an NK-92 cell line or a KHYG-1 cell line.
61. The method of embodiment 59, wherein the transformed natural killer cell line is an KHYG-1 cell line.
62. The method of any one of embodiments 55 to 61, wherein the CAR specifically binds a cancer associated antigen.
63. The method of embodiment 62, wherein the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.
64. The method of embodiment 62, wherein the cancer associated antigen comprises a blood cancer associated antigen.
65. The method of embodiment 64, wherein the blood cancer associated antigen comprises CD38, CD319/SLAMF-7, TNFRSF17/BCMA, SYND1/CD138, CD229, CD47, CD123/IL3-RA, CD19, CD20, CD22, or CLL-1.
66. The method of embodiment 64, wherein the blood cancer associated antigen comprises CD38.
67. The method of embodiment 66, wherein the CAR comprises a targeting domain amino acid sequence that is at least 80% identical to that set forth in any one of SEQ ID NOs: 1-6.
68. The method of embodiment 66, wherein the CAR comprises a targeting domain amino acid sequence that is at least 90% identical to that set forth in any one of SEQ ID NOs: 1-6.
69. The method of embodiment 66, wherein the CAR comprises a targeting domain amino acid sequence that is at least 95% identical to that set forth in any one of SEQ ID NOs: 1-6.
70. The method of embodiment 66, wherein the CAR comprises a targeting domain amino acid sequence that is at least 98% identical to that set forth in any one of SEQ ID NOs: 1-6.
71. The method of embodiment 66, wherein the CAR comprises a targeting domain amino acid sequence that is identical to that set forth in any one of SEQ ID NOs: 1-6.
72. The method of embodiment 66, wherein the CAR comprises a targeting domain amino acid sequence that is at least 90% identical to that set forth in SEQ ID NOs: 1 and 2.
73. The method of embodiment 66, wherein the CAR comprises a targeting domain amino acid sequence that is at least 95% identical to that set forth in SEQ ID NOs: 1 and 2.
74. The method of embodiment 66, wherein the CAR comprises a targeting domain amino acid sequence that is at least 98% identical to that set forth in SEQ ID NOs: 1 and 2.
75. The method of embodiment 66, wherein the CAR comprises a targeting domain amino acid sequence that is identical to that set forth in SEQ ID NOs: 1 and 2.
76. The method of embodiment 66, wherein the CAR comprises a targeting domain amino acid sequence that is at least 90% identical to that set forth in SEQ ID NOs: 3 and 4.
77. The method of embodiment 66, wherein the CAR comprises a targeting domain amino acid sequence that is at least 95% identical to that set forth in SEQ ID NOs: 3 and 4.
78. The method of embodiment 66, wherein the CAR comprises a targeting domain amino acid sequence that is at least 98% identical to that set forth in SEQ ID NOs: 3 and 4.
79. The method of embodiment 66, wherein the CAR comprises a targeting domain amino acid sequence that is identical to that set forth in SEQ ID NOs: 3 and 4.
80. The method of embodiment 66, wherein the CAR comprises a targeting domain amino acid sequence that is at least 90% identical to that set forth in SEQ ID NOs: 5 and 6.
81. The method of embodiment 66, wherein the CAR comprises a targeting domain amino acid sequence that is at least 95% identical to that set forth in SEQ ID NOs: 5 and 6.
82. The method of embodiment 66, wherein the CAR comprises a targeting domain amino acid sequence that is at least 98% identical to that set forth in SEQ ID NOs: 5 and 6.
83. The method of embodiment 66, wherein the CAR comprises a targeting domain amino acid sequence that is identical to that set forth in SEQ ID NOs: 5 and 6.
84. The method of any one of embodiments 55 to 83, wherein the CAR comprises a transmembrane domain derived from a human CD8 protein.
85. The method of any one of embodiments 55 to 84, wherein the CAR comprises a DAP10, DAP12, 2B4 (CD244), or human 4-1BB protein.
86. The method of any one of embodiments 55 to 85, wherein the CAR comprises a human 4-1BB protein.
87. The method of any one of embodiments 55 to 86, wherein the CAR comprises a human CD3 zeta protein.
88. The method of any one of embodiments 55 to 87, wherein the CAR comprises a targeting domain that is derived from an antibody that exhibits a lower affinity for CD38 than Daratumumab.

89. The method of any one of embodiments 55 to 88, wherein the engineered natural killer cell further comprises a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

90. The method of any one of embodiments 55 to 89, wherein the engineered natural killer cell further comprises a mutant TNF-related apoptosis-inducing ligand (TRAIL) polypeptide, wherein the mutant TRAIL polypeptide induces increased signaling or possesses increased binding affinity to a TRAIL ligand.

91. The method of embodiment 90, wherein the TRAIL ligand comprises TNFRSF10A (DR4) or TNFRSF10B (DR5).

92. The method of embodiment 90, wherein the mutant TRAIL polypeptide comprises a D269H/E195R mutation of human TRAIL.

93. The method of embodiment 90, wherein the mutant TRAIL polypeptide comprises a G131R/N199R/K201H mutation of human TRAIL.

94. The method of any one of embodiments 55 to 93, wherein the CAR or the mutant TRAIL polypeptide is integrated into the genome of the engineered natural killer cell.

95. The method of any one of embodiments 55 to 94, wherein the engineered natural killer cell further comprises a deletion or reduction in activity of a checkpoint inhibitory receptor.

96. The method of embodiment 95, wherein the checkpoint inhibitory receptor comprises CD85d, CD85j, CD96, CD152, CD159a, CD223, CD279, CD328, SIGLEC9, TIGIT or TIM-3.

97. The method of embodiment 96, wherein the checkpoint inhibitory receptor comprises CD96, CD152, or CD328.

98. The method of embodiment 97, wherein the checkpoint inhibitory receptor comprises CD96.

99. The method of embodiment 97, wherein the checkpoint inhibitory receptor comprises CD152

100. The method of embodiment 97, wherein the checkpoint inhibitory receptor comprises CD328.

101. The method of embodiments 41 or 46, wherein the checkpoint inhibitory receptor is deleted in whole or in part from the engineered natural killer cell genome, or is disrupted by insertion or deletion of one or more nucleotides at the chromosomal level.

102. The method of any one of embodiments 95 to 101, wherein the engineered natural killer cell comprises an siRNA that targets a checkpoint inhibitory receptor.

103. The method of any one of embodiments 95 to 102, wherein the checkpoint inhibitory receptor is deleted from the engineered natural killer cell genome.

104. The method of any one of embodiments 55 to 103, wherein the pharmaceutical composition comprises a pharmaceutically acceptable carrier, stabilizer, or excipient.

105. The method of embodiment 104, wherein the pharmaceutical composition is formulated for intravenous administration.

106. The method of embodiment 104, wherein the pharmaceutical composition is formulated for intraperitoneal administration.

107. The method of any one of embodiments 55 to 106, wherein the cancer comprises a leukemia, a lymphoma, or a myeloma.

108. The method of any one of embodiments 55 to 107, wherein the cancer comprises multiple myeloma.

109. The method of any one of embodiments 55 to 108, wherein the pharmaceutical composition is administered before during or after administration of a proteasome inhibitor.

110. The method of any one of embodiments 55 to 108, wherein the pharmaceutical composition is administered before, during, or after a low-dose metronomic cyclophosphamide treatment regimen.

111. A method of making a pharmaceutical composition comprising an engineered natural killer cell, wherein the engineered natural killer cell exhibits a high level of cell-surface expression of E-selectin ligand, wherein the engineered natural killer cell comprises a chimeric antigen receptor (CAR), wherein the method comprises incubating a natural killer cell with a polynucleotide that encodes the CAR.

112. The method of embodiment 111, wherein the engineered natural killer cell comprises a plurality of engineered natural killer cells that are greater than 25% positive for an antigen bound by the HECA-452 antibody.

113. The method of embodiment 111, wherein the engineered natural killer cell exhibits a low level of cell-surface expression of a TRAIL receptor, wherein the TRAIL receptor comprises TNFRSF10A (DR4) or TNFRSF10B (DR5).

114. The method of any one of embodiments 111 to 113, wherein the engineered natural killer cell comprises a primary natural killer cell.

115. The method of any one of embodiments 111 to 113, wherein the engineered natural killer cell comprises a transformed natural killer cell line.

116. The method of embodiment 115, wherein the transformed natural killer cell line is the NK-92 cell line or the KHYG-1 cell line.

117. The method of embodiment 115, wherein the transformed natural killer cell line is the KHYG-1 cell line.

118. The method of any one of embodiments 111 to 117, wherein the CAR specifically binds a cancer associated antigen.

119. The method of embodiment 118, wherein the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

120. The method of embodiment 118, wherein the cancer associated antigen comprises a blood cancer associated antigen.

121. The method of embodiment 120, wherein the blood cancer associated antigen comprises CD38, CD319/SLAMF-7, TNFRSF17/BCMA, SYND1/CD138, CD229, CD47, CD123/IL3-RA, CD19, CD20, CD22, or CLL-1.

122. The method of embodiment 120, wherein the blood cancer associated antigen comprises CD38.

123. The method of embodiment 122, wherein the CAR comprises a targeting domain amino acid sequence that is at least 80% identical to that set forth in any one of SEQ ID NOs: 1-6.

124. The method of embodiment 122, wherein the CAR comprises a targeting domain amino acid sequence that is at least 90% identical to that set forth in any one of SEQ ID NOs: 1-6.

125. The method of embodiment 122, wherein the CAR comprises a targeting domain amino acid sequence that is at least 95% identical to that set forth in any one of SEQ ID NOs: 1-6.
126. The method of embodiment 122, wherein the CAR comprises a targeting domain amino acid sequence that is at least 98% identical to that set forth in any one of SEQ ID NOs: 1-6.
127. The method of embodiment 122, wherein the CAR comprises a targeting domain amino acid sequence that is identical to that set forth in any one of SEQ ID NOs: 1-6.
128. The method of embodiment 122, wherein the CAR comprises a targeting domain amino acid sequence that is at least 90% identical to that set forth in SEQ ID NOs: 1 and 2.
129. The method of embodiment 122, wherein the CAR comprises a targeting domain amino acid sequence that is at least 95% identical to that set forth in SEQ ID NOs: 1 and 2.
130. The method of embodiment 122, wherein the CAR comprises a targeting domain amino acid sequence that is at least 98% identical to that set forth in SEQ ID NOs: 1 and 2.
131. The method of embodiment 122, wherein the CAR comprises a targeting domain amino acid sequence that is identical to that set forth in SEQ ID NOs: 1 and 2.
132. The method of embodiment 122, wherein the CAR comprises a targeting domain amino acid sequence that is at least 90% identical to that set forth in SEQ ID NOs: 3 and 4.
133. The method of embodiment 122, wherein the CAR comprises a targeting domain amino acid sequence that is at least 95% identical to that set forth in SEQ ID NOs: 3 and 4.
134. The method of embodiment 122, wherein the CAR comprises a targeting domain amino acid sequence that is at least 98% identical to that set forth in SEQ ID NOs: 3 and 4.
135. The method of embodiment 122, wherein the CAR comprises a targeting domain amino acid sequence that is identical to that set forth in SEQ ID NOs: 3 and 4.
136. The method of embodiment 122, wherein the CAR comprises a targeting domain amino acid sequence that is at least 90% identical to that set forth in SEQ ID NOs: 5 and 6.
137. The method of embodiment 122, wherein the CAR comprises a targeting domain amino acid sequence that is at least 95% identical to that set forth in SEQ ID NOs: 5 and 6.
138. The method of embodiment 122, wherein the CAR comprises a targeting domain amino acid sequence that is at least 98% identical to that set forth in SEQ ID NOs: 5 and 6.
139. The method of embodiment 122, wherein the CAR comprises a targeting domain amino acid sequence that is identical to that set forth in SEQ ID NOs: 5 and 6.
140. The method of any one of embodiments 111 to 139, wherein the CAR comprises a transmembrane domain derived from a human CD8 alpha polypeptide.
141. The method of any one of embodiments 111 to 140, wherein the CAR comprises an intracellular domain comprising a DAP10, DAP12, 2B4 (CD244), or a human 4-1BB protein.
142. The method of any one of embodiments 111 to 141, wherein the CAR comprises a human 4-1BB polypeptide
143. The method of any one of embodiments 111 to 142, wherein the CAR comprises a human CD3 zeta polypeptide.
144. The method of any one of embodiments 111 to 143, wherein the CAR comprises a targeting domain that is derived from an antibody that exhibits a lower affinity for CD38 than Daratumumab.
145. The method of any one of embodiments 111 to 144, further comprising incubating the engineered natural killer cell with a polynucleotide that encodes a second chimeric antigen receptor, the second chimeric antigen receptor comprising CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.
146. The method of any one of embodiments 111 to 145, further comprising incubating the engineered natural killer cell with a polynucleotide that encodes a mutant TNF-related apoptosis-inducing ligand (TRAIL) polypeptide, wherein the mutant TRAIL polypeptide induces increased signaling or possesses increased binding affinity to a TRAIL ligand.
147. The method of embodiment 146, wherein the TRAIL ligand comprises TNFRSF10A (DR4) or TNFRSF10B (DR5).
148. The method of embodiment 146, wherein the mutant TRAIL polypeptide comprises a D269H/E195R mutation of human TRAIL.
149. The method of embodiment 146, wherein the mutant TRAIL polypeptide comprises a G131R/N199R/K201H mutation of human TRAIL.
150. The method of any one of embodiments 111 to 149, wherein the CAR or the mutant TRAIL polynucleotide is integrated into the genome of the engineered natural killer cell.
151. The method of any one of embodiments 111 to 150, further comprising incubating the engineered natural killer cell with a polynucleotide that deletes or reduces activity of a checkpoint inhibitory receptor.
152. The method of embodiment 151, wherein the checkpoint inhibitory receptor comprises CD85d, CD85j, CD96, CD152, CD159a, CD223, CD279, CD328, SIGLEC9, TIGIT or TIM-3.
153. The method of embodiment 151, wherein the checkpoint inhibitory receptor comprises CD96, CD152, or CD328.
154. The method of embodiment 153, wherein the checkpoint inhibitory receptor comprises CD96.
155. The method of embodiment 153, wherein the checkpoint inhibitory receptor comprises CD152
156. The method of embodiment 153, wherein the checkpoint inhibitory receptor comprises CD328.
157. The method of embodiments of any one of 111 to 156, wherein the checkpoint inhibitory receptor is deleted in whole or in part from the engineered natural killer cell genome, or is disrupted by insertion or deletion of one or more nucleotides at the chromosomal level.
158. The method of any one of embodiments 111 to 157, wherein the engineered natural killer cell comprises an siRNA that targets a checkpoint inhibitory receptor.
159. The method of any one of embodiments 111 to 158, wherein the polynucleotide comprises a viral vector.
160. The method of embodiment 159, wherein the viral vector is a lentivirus.
161. The method of embodiment 159, wherein the viral vector is a retrovirus.
162. The method of any one of embodiments 111 to 161, wherein the polynucleotide comprises mRNA.

163. The method of any one of embodiments 111 to 162, wherein the polynucleotide is integrated into the genome of the engineered natural killer cell.

164. The method of any one of embodiments 111 to 163, wherein the cell is treated with a chemical to increase fucosylation of the engineered natural killer cell.

165. The method of any one of embodiments 111 to 163, further comprising admixing the engineered natural killer cell with a pharmaceutically acceptable carrier, stabilizer, or excipient.

166. A pharmaceutical composition comprising an engineered natural killer cell, wherein the engineered natural killer cell exhibits expression of the FUT6 or FUT7 protein, wherein the engineered natural killer cell comprises a chimeric antigen receptor (CAR).

167. The pharmaceutical composition of embodiment 166, wherein the engineered natural killer cell comprises an exogenous polynucleotide encoding the FUT6 or FUT7 protein.

168. The pharmaceutical composition of embodiment 166, wherein the CAR specifically binds a cancer associated antigen.

169. The pharmaceutical composition of embodiment 167, wherein the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

170. The pharmaceutical composition of embodiment 167, wherein the cancer associated antigen comprises a blood cancer associated antigen.

171. The pharmaceutical composition of embodiment 170, wherein the blood cancer associated antigen comprises CD38, CD319/SLAMF-7, TNFRSF17/BCMA, SYND1/CD138, CD229, CD47, CD123/IL3-RA, CD19, CD20, CD22, or CLL-1.

172. The pharmaceutical composition of embodiment 170, wherein the blood cancer associated antigen comprises CD38.

173. The pharmaceutical composition of embodiment 172, wherein the CAR comprises a targeting domain amino acid sequence that is at least 80% identical to that set forth in any one of SEQ ID NOs: 1-6.

174. The pharmaceutical composition of embodiment 172, wherein the CAR comprises a targeting domain amino acid sequence that is at least 90% identical to that set forth in any one of SEQ ID NOs: 1-6.

175. The pharmaceutical composition of embodiment 172, wherein the CAR comprises a targeting domain amino acid sequence that is at least 95% identical to that set forth in any one of SEQ ID NOs: 1-6.

176. The pharmaceutical composition of embodiment 172, wherein the CAR comprises a targeting domain amino acid sequence that is at least 98% identical to that set forth in any one of SEQ ID NOs: 1-6.

177. The pharmaceutical composition of embodiment 172, wherein the CAR comprises a targeting domain amino acid sequence that is identical to that set forth in any one of SEQ ID NOs: 1-6.

178. The pharmaceutical composition of embodiment 172, wherein the CAR comprises a targeting domain amino acid sequence that is at least 90% identical to that set forth in SEQ ID NOs: 1 and 2.

179. The pharmaceutical composition of embodiment 172, wherein the CAR comprises a targeting domain amino acid sequence that is at least 95% identical to that set forth in SEQ ID NOs: 1 and 2.

180. The pharmaceutical composition of embodiment 172, wherein the CAR comprises a targeting domain amino acid sequence that is at least 98% identical to that set forth in SEQ ID NOs: 1 and 2.

181. The pharmaceutical composition of embodiment 172, wherein the CAR comprises a targeting domain amino acid sequence that is identical to that set forth in SEQ ID NOs: 1 and 2.

182. The pharmaceutical composition of embodiment 172, wherein the CAR comprises a targeting domain amino acid sequence that is at least 90% identical to that set forth in SEQ ID NOs: 3 and 4.

183. The pharmaceutical composition of embodiment 172, wherein the CAR comprises a targeting domain amino acid sequence that is at least 95% identical to that set forth in SEQ ID NOs: 3 and 4.

184. The pharmaceutical composition of embodiment 172, wherein the CAR comprises a targeting domain amino acid sequence that is at least 98% identical to that set forth in SEQ ID NOs: 3 and 4.

185. The pharmaceutical composition of embodiment 172, wherein the CAR comprises a targeting domain amino acid sequence that is identical to that set forth in SEQ ID NOs: 3 and 4.

186. The pharmaceutical composition of embodiment 172, wherein the CAR comprises a targeting domain amino acid sequence that is at least 90% identical to that set forth in SEQ ID NOs: 5 and 6.

187. The pharmaceutical composition of embodiment 172, wherein the CAR comprises a targeting domain amino acid sequence that is at least 95% identical to that set forth in SEQ ID NOs: 5 and 6.

188. The pharmaceutical composition of embodiment 172, wherein the CAR comprises a targeting domain amino acid sequence that is at least 98% identical to that set forth in SEQ ID NOs: 5 and 6.

189. The pharmaceutical composition of embodiment 172, wherein the CAR comprises a targeting domain amino acid sequence that is identical to that set forth in SEQ ID NOs: 5 and 6.

190. A method of treating a subject with cancer comprising administering to the subject a pharmaceutical composition comprising an engineered natural killer cell, wherein the engineered natural killer cell exhibits expression of the FUT6 or FUT7 protein, wherein the engineered natural killer cell comprises a chimeric antigen receptor (CAR).

191. The method of embodiment 190, wherein the engineered natural killer cell comprises an exogenous polynucleotide encoding the FUT6 or FUT7 protein.

192. The method of embodiment 190, wherein the CAR specifically binds a cancer associated antigen.

193. The method of embodiment 192, wherein the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

194. The method of embodiment 192, wherein the cancer associated antigen comprises a blood cancer associated antigen.

195. The method of embodiment 194, wherein the blood cancer associated antigen comprises CD38, CD319/

SLAMF-7, TNFRSF17/BCMA, SYND1/CD138, CD229, CD47, CD123/IL3-RA, CD19, CD20, CD22, or CLL-1.

196. The method of embodiment 195, wherein the blood cancer associated antigen comprises CD38.

197. The method of embodiment 196, wherein the CAR comprises a targeting domain amino acid sequence that is at least 80% identical to that set forth in any one of SEQ ID NOs: 1-6.

198. The method of embodiment 196, wherein the CAR comprises a targeting domain amino acid sequence that is at least 90% identical to that set forth in any one of SEQ ID NOs: 1-6.

199. The method of embodiment 196, wherein the CAR comprises a targeting domain amino acid sequence that is at least 95% identical to that set forth in any one of SEQ ID NOs: 1-6.

200. The method of embodiment 196, wherein the CAR comprises a targeting domain amino acid sequence that is at least 98% identical to that set forth in any one of SEQ ID NOs: 1-6.

201. The method of embodiment 196, wherein the CAR comprises a targeting domain amino acid sequence that is identical to that set forth in any one of SEQ ID NOs: 1-6.

202. The method of embodiment 196, wherein the CAR comprises a targeting domain amino acid sequence that is at least 90% identical to that set forth in SEQ ID NOs: 1 and 2.

203. The method of embodiment 196, wherein the CAR comprises a targeting domain amino acid sequence that is at least 95% identical to that set forth in SEQ ID NOs: 1 and 2.

204. The method of embodiment 196, wherein the CAR comprises a targeting domain amino acid sequence that is at least 98% identical to that set forth in SEQ ID NOs: 1 and 2.

205. The method of embodiment 196, wherein the CAR comprises a targeting domain amino acid sequence that is identical to that set forth in SEQ ID NOs: 1 and 2.

206. The method of embodiment 196, wherein the CAR comprises a targeting domain amino acid sequence that is at least 90% identical to that set forth in SEQ ID NOs: 3 and 4.

207. The method of embodiment 196, wherein the CAR comprises a targeting domain amino acid sequence that is at least 95% identical to that set forth in SEQ ID NOs: 3 and 4.

208. The method of embodiment 196, wherein the CAR comprises a targeting domain amino acid sequence that is at least 98% identical to that set forth in SEQ ID NOs: 3 and 4.

209. The method of embodiment 196, wherein the CAR comprises a targeting domain amino acid sequence that is identical to that set forth in SEQ ID NOs: 3 and 4.

210. The method of embodiment 196, wherein the CAR comprises a targeting domain amino acid sequence that is at least 90% identical to that set forth in SEQ ID NOs: 5 and 6.

211. The method of embodiment 196, wherein the CAR comprises a targeting domain amino acid sequence that is at least 95% identical to that set forth in SEQ ID NOs: 5 and 6.

212. The method of embodiment 196, wherein the CAR comprises a targeting domain amino acid sequence that is at least 98% identical to that set forth in SEQ ID NOs: 5 and 6.

213. The method of embodiment 196, wherein the CAR comprises a targeting domain amino acid sequence that is identical to that set forth in SEQ ID NOs: 5 and 6.

214. A method of making a pharmaceutical composition comprising an engineered natural killer cell, wherein the engineered natural killer cell exhibits expression of the FUT6 or FUT7 protein, wherein the engineered natural killer cell comprises a chimeric antigen receptor (CAR), wherein the method comprises incubating a natural killer cell with a polynucleotide that encodes the CAR.

215. The method of embodiment 214, wherein the engineered natural killer cell comprises an exogenous polynucleotide encoding the FUT6 or FUT7 protein.

216. The method of embodiment 214, wherein the CAR specifically binds a cancer associated antigen.

217. The method of embodiment 216, wherein the cancer associated antigen comprises CD38, CD319/SLAMF-7, TNFRSF17/BCMA, SYND1/CD138, CD229, CD47, Her2/Neu, epidermal growth factor receptor (EGFR), CD123/IL3-RA, CD19, CD20, CD22, Mesothelin, EpCAM, MUC1, MUC16, Tn antigen, NEU5GC, NeuGcGM3, GD2, CLL-1, or HERV-K.

218. The method of embodiment 216, wherein the cancer associated antigen comprises a blood cancer associated antigen.

219. The method of embodiment 218, wherein the blood cancer associated antigen comprises CD38, CD319/SLAMF-7, TNFRSF17/BCMA, SYND1/CD138, CD229, CD47, CD123/IL3-RA, CD19, CD20, CD22, or CLL-1.

220. The method of embodiment 218, wherein the blood cancer associated antigen comprises CD38.

221. The method of embodiment 220, wherein the CAR comprises a targeting domain amino acid sequence that is at least 80% identical to that set forth in any one of SEQ ID NOs: 1-6.

222. The method of embodiment 220, wherein the CAR comprises a targeting domain amino acid sequence that is at least 90% identical to that set forth in any one of SEQ ID NOs: 1-6.

223. The method of embodiment 220, wherein the CAR comprises a targeting domain amino acid sequence that is at least 95% identical to that set forth in any one of SEQ ID NOs: 1-6.

224. The method of embodiment 220, wherein the CAR comprises a targeting domain amino acid sequence that is at least 98% identical to that set forth in any one of SEQ ID NOs: 1-6.

225. The method of embodiment 220, wherein the CAR comprises a targeting domain amino acid sequence that is identical to that set forth in any one of SEQ ID NOs: 1-6.

226. The method of embodiment 220, wherein the CAR comprises a targeting domain amino acid sequence that is at least 90% identical to that set forth in SEQ ID NOs: 1 and 2.

227. The method of embodiment 220, wherein the CAR comprises a targeting domain amino acid sequence that is at least 95% identical to that set forth in SEQ ID NOs: 1 and 2.

228. The method of embodiment 220, wherein the CAR comprises a targeting domain amino acid sequence that is at least 98% identical to that set forth in SEQ ID NOs: 1 and 2.

229. The method of embodiment 220, wherein the CAR comprises a targeting domain amino acid sequence that is identical to that set forth in SEQ ID NOs: 1 and 2.

230. The method of embodiment 220, wherein the CAR comprises a targeting domain amino acid sequence that is at least 90% identical to that set forth in SEQ ID NOs: 3 and 4.

231. The method of embodiment 220, wherein the CAR comprises a targeting domain amino acid sequence that is at least 95% identical to that set forth in SEQ ID NOs: 3 and 4.

232. The method of embodiment 220, wherein the CAR comprises a targeting domain amino acid sequence that is at least 98% identical to that set forth in SEQ ID NOs: 3 and 4.

233. The method of embodiment 220, wherein the CAR comprises a targeting domain amino acid sequence that is identical to that set forth in SEQ ID NOs: 3 and 4.

234. The method of embodiment 220, wherein the CAR comprises a targeting domain amino acid sequence that is at least 90% identical to that set forth in SEQ ID NOs: 5 and 6.

235. The method of embodiment 220, wherein the CAR comprises a targeting domain amino acid sequence that is at least 95% identical to that set forth in SEQ ID NOs: 5 and 6.

236. The method of embodiment 220, wherein the CAR comprises a targeting domain amino acid sequence that is at least 98% identical to that set forth in SEQ ID NOs: 5 and 6.

237. The method of embodiment 220, wherein the CAR comprises a targeting domain amino acid sequence that is identical to that set forth in SEQ ID NOs: 5 and 6.

EXAMPLES

The following examples are merely illustrative of the various embodiments disclosed herein and do not limit the claims in any way.

Figure 2A:
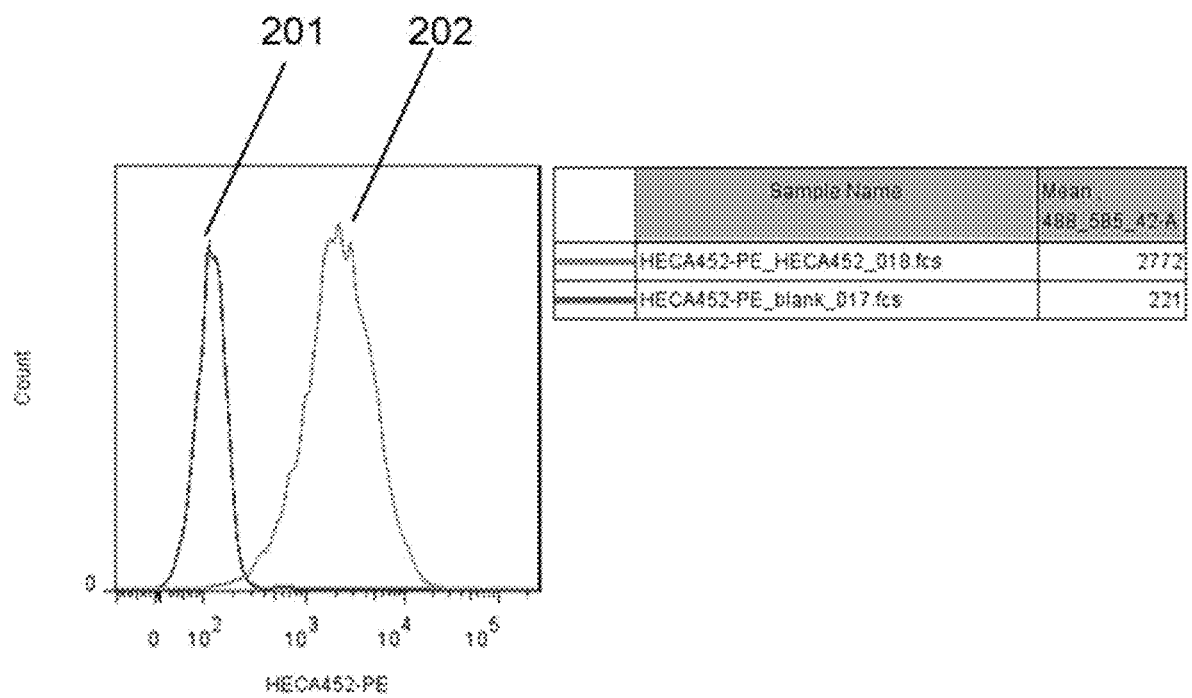
FIGS. 2A-B illustrate binding of the HECA-452 antibody to KHYG-1 cells (A) and NK-92 cells (B) as analyzed by flow cytometry.
Figure 2B:
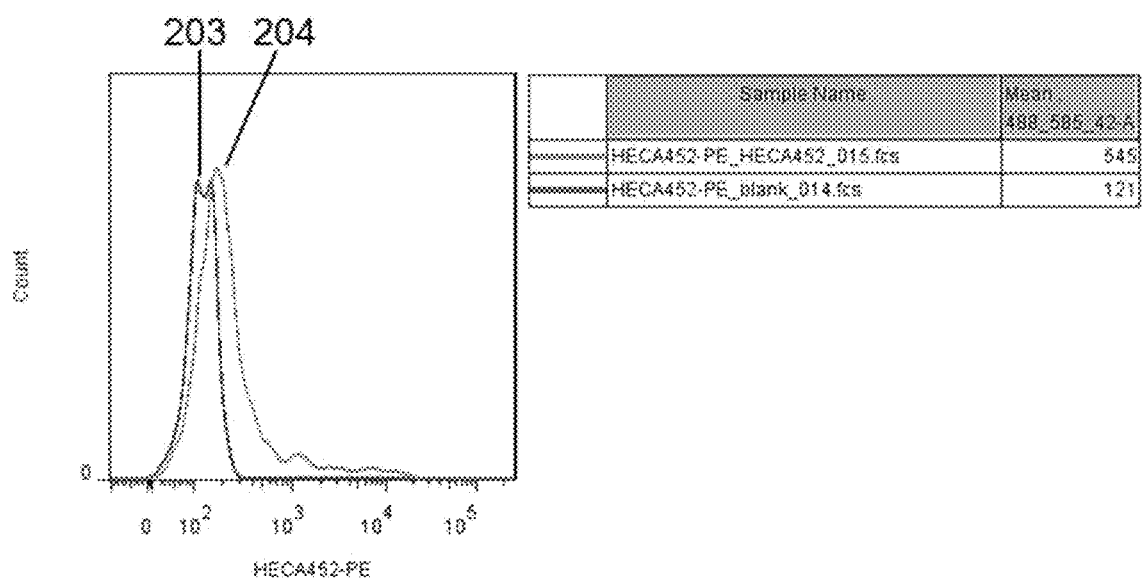

Example 1—The NK Cell Line KHYG-1 Exhibits Higher Level Expression of E-Selectin Ligands than the NK-92 Cell Line To determine expression of E-selectin ligands on different NK cell lines we cultured NK-92 and KHYG-1 cells in RPMI 1640 medium supplemented with 10% FBS and IL-2 at 10 ng/ml. Cells were taken from culture, washed, and stained with PE conjugated HECA-452 antibody or PE-isotype control. Cells were then run on a flow cytometer and mean fluorescence intensity (MFI) was determined for each cell line compared to control. FIG. 2A is a representative experiment and shows that KHYG-1 cells exhibit much higher HECA-452 reactivity 202 when compared to isotype control 201 (MFI of 2772 vs. 221). FIG. 2B shows the opposite result with NK-92 cells which exhibit low HECA-452 reactivity 204 when compared to isotype control 203 (MFI of 545 vs. 121).

Figure 3:
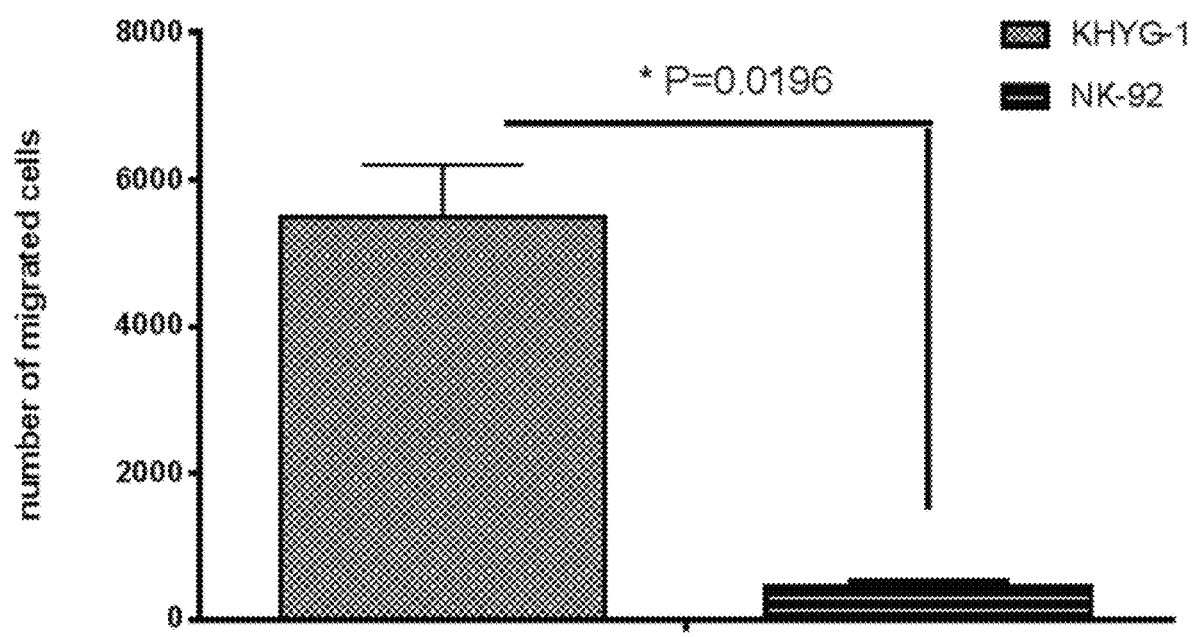
FIG. 3 illustrates migration of KHYG-1 cells along an SDF-1 gradient as compared to NK-92 cells.
Figure 4A:
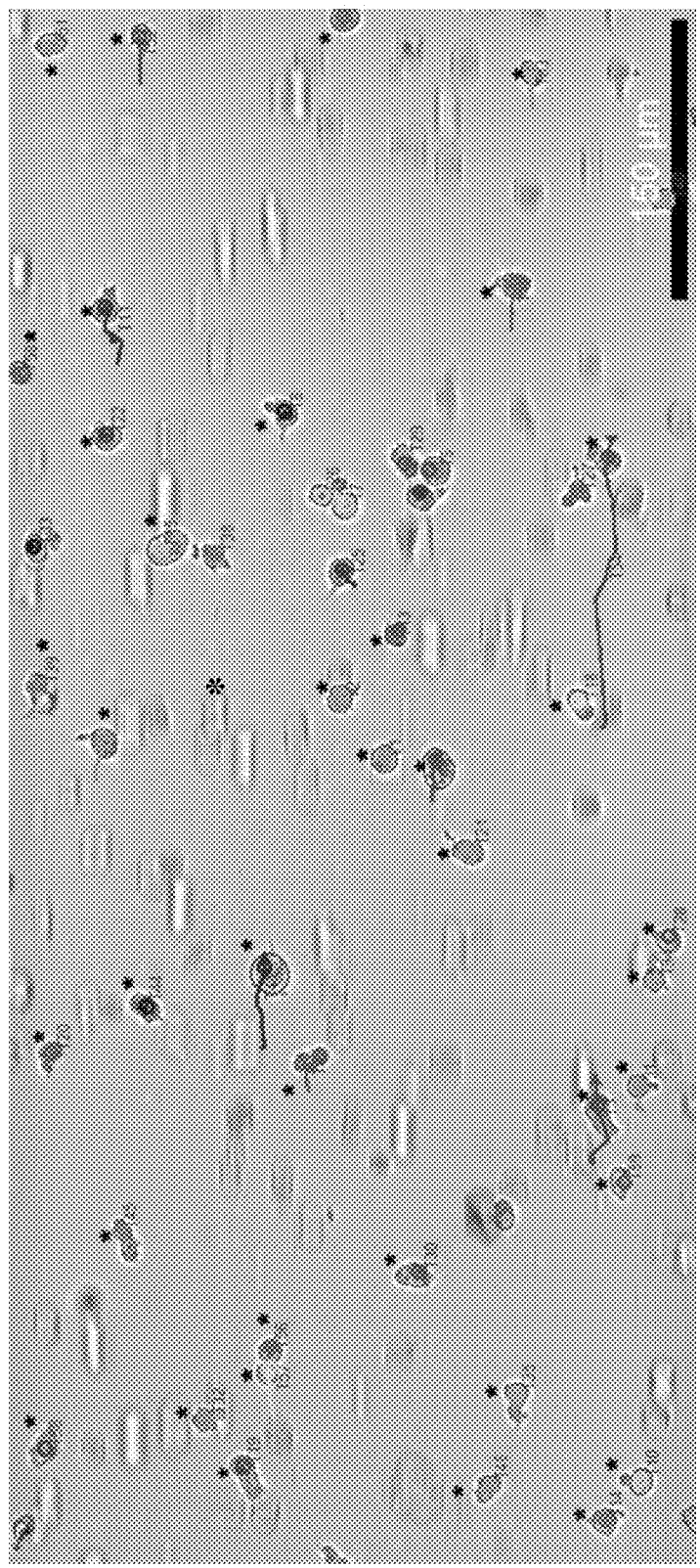
FIGS. 4A-B illustrate a still frame from a video observing migration of KHYG-1 cells (A) and NK-92 cells (B) in a flow cell. Cells that are stalled or migrating slowly are marked with an asterisk.
Figure 4B:
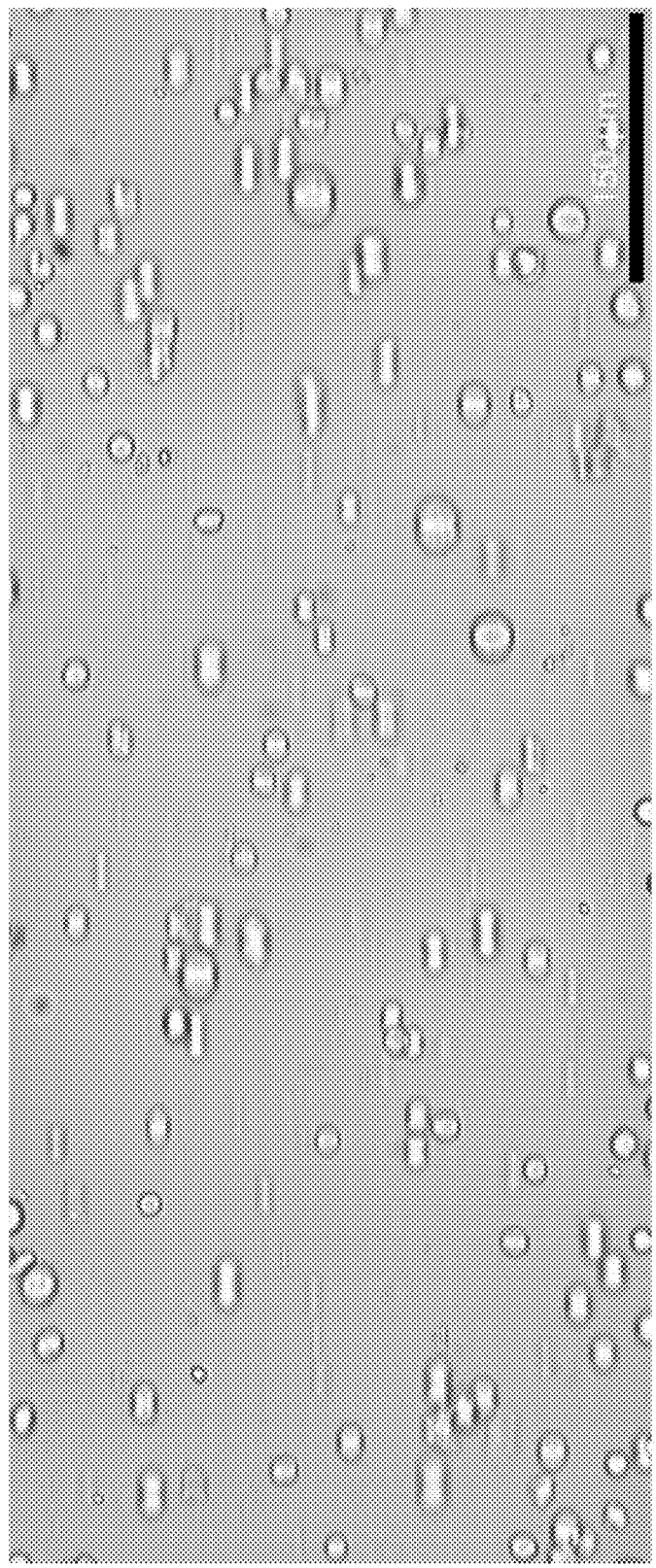

Example 2—The NK Cell Line KHYG-1 Exhibits an In Vitro Phenotype of Reduced E-Selectin Ligand To determine if this increased HECA-452 reactivity translated into a phenotypic difference in migration of KHYG-1 and NK-92 cells were examined in vitro. First, migration along a Stromal-derived factor-1 (SDF-1) gradient was examined. FIG. 3 shows that KHYG-1 cells (left bar) exhibited approximately a 6-fold increase in migration when compared to NK-92 cells (right bar). Additionally, migration in an E-selectin coated flow-cell was monitored. FIGS. 4A and B show still frame shots of video taken during the flow cell assay. FIG. 4A shows that many KHYG-1 cells are immobile or exhibit very slow movement in the flow cell assay (asterisks). To the contrary FIG. 4B shows that NK-92 flow unimpeded through the frame of the flow-cell.

Migration Assay

The log phase NK-92 or KHYG1 cells were harvested, washed and suspended in serum free culture medium (RPMI1640 for KHYG1, aMEM for NK-92) containing 10 ng/mL of IL-2 to starve for 4 hours. 600 µL of serum free culture medium containing 100 ng/mL of SDF1 and 10 ng/mL of IL-2 was added to each well (for 12 well plate), then 100 µL of starved cell suspension was loaded to the upper migration chambers that pore size is 5.0 µm (Costar; Corning). The cells were then cultivated for 4 hours at 37° C. cells in CO2 incubator. After 4 hours, the medium in lower compartment (containing migrated cells) was harvested and the cell number was counted by using BD Accuri™ C6 flow cytometer.

Flow Cell/Rolling Assay

Rolling assay was performed in 8 channel microfluidic biochips (Cellix Limited, Dublin, Ireland) using a Mirus Evo NanoPump (Cellix Limited). The biochip's channels Vena8 Fluoro+(Cellix Limited) were coated with 15 µg/mL of E-selectin (PeProtech, Rocky Hill, US) in Tris.HCl pH 7.4 supplemented with 1 mM $CaCl_2$ and incubated overnight at 4° C. Each channel was blocked with 1% BSA (bovine serum albumin) or where indicated with 15 µg/mL of anti-E-selectin blocking antibody (Clone BBIG-E1, R&D System; Minneapolis, US) and incubated at 37° C. 1 h before the assay. Cells were washed and resuspended in rolling assay buffer (RPMI 1640 media without phenol red supplemented with 1% heat-inactivated FBS (fetal bovine serum), 5 mM HEPES and 1 mM CaCl2) at $2\times10^6$ cells/ml. 80 µL of cell suspension were loaded onto the microchannels and rolling assay was run at 0.5 dyne/$cm^2$ at room temperature. Cells were monitored in 5 different positions along the channel using an A-Plan 10×/0.25 objective lens (Carl Zeiss Microscopy GmbH; Jena, Germany) of an AX10Vert.A1 Microscope (Carl Zeiss Microscopy GmbH). 30 frames per position were collected at 0.5 sec from each other using a 01 QIClick F-M-12 Mono 12-bit camera (QImaging; Surrey, Canada). Images were acquired using the Vena Flux assay software (Cellix Limited) and analyzed using the Image-Pro Premiere software (Media Cybernetics; Rockville, US). A rolling cell was defined as a cell travelling a distance corresponding to more than its diameter. The total cell number of 5 different positions per channel was counted, then the average number of all channels was calculated.

Example 3—In Vivo Homing of the NK Cell Line KHYG-1

In an in vivo mouse model, we will track homing of NK cells to distant bone marrow niches. This will be done by using in vivo confocal microscopy or flow cytometric analysis on bone marrow. Cell lines to analyzed for bone marrow homing will be the KHYG-1 (high HECA-452 binding) and the NK-92 high (low HECA-452 binding). Both cell lines will be injected into the same mouse, but will be labeled with two different fluorophores to perform a competitive bone marrow homing analysis. We would look at one time point, such as 4, 8, 12, or 24 hours.

NK cells will be labeled with fluorescent dyes (Calcein AM or CellTracker Dyes). Then homing to the BM will be imaged in vivo using a Zeiss 710 confocal system (Carl Zeiss Microimaging, Jena, Germany) or quantified using a FACS Aria II flow cytometer. In the confocal, a skin flap will be made in the scalp of the mice to expose the underlying dorsal skull surface. Images of the tumors will be captured in approximately 1 hour-long sessions using in vivo confocal microscopy. Images with cellular detail will be obtained through the intact mouse skull at depths of up to 250 µm from the surface of the skull using a 10×0.45NA Plan-Apo objective (Carl Zeiss Microimaging). Multiple imaging depths will be acquired, and a maximum intensity z-projection will be performed in Image J to merge the images. GFP will excite with the 488 nm line on an Argon laser. Blood vessels will be imaged using Evans Blue (Sigma-Aldrich, St. Louis, Mo.) excited with a 633 nm laser. Emission signals will be collected by the Zeiss internal confocal Quasar detectors.

Example 4—In Vivo Efficacy of CD38 CAR Expressing NK Cells Against Multiple Myeloma Transduce KHYG-1 Cells with High, Intermediate and Low Affinity CD38 CARs Second generation CD38 CAR constructs are generated with targeting domains of different affinities: high, intermediate and low. The CAR also comprises a CD3ζ and 4-1BB costimulatory domain and linked by a 2A sequence to ΔNGFR (the marker gene that will be used to trace CAR-transduced cells) separated as a transduction marker. The different affinity CD38 CARs will be generated as lenti- or retroviral constructs as it is not well known which type of constructs will transduce the KHYG-1 cells better. We will use sequences for the CAR targeting domain derived from SEQ ID NOs: 1-6. Depending on the results of the pilot experiments in which we will address this issue, we will transduce KHYG-1 cells with the different CD38 CAR constructs and select them for high purity to test their functional efficacy against multiple myeloma (MM) cell lines as described below.

In the functional testing stage, we will monitor the CAR transduced KHYG-1 cells for proliferation and expansion (cell counting), CD16, CD56, CD3, KIR2DL1, KIR2DL2/3, KIR3DL1 and NKG2A expression at day 0 week 1, 3 and 6 (at the end of expansion) Expression of the apoptosis marker annexin-V will also be investigated. Another important phenotypical parameter is the expression of CD38, since we have observed that CAR T cells do not express CD38, despite their activated status. We will subsequently assess their CD38-dependent proliferative and cytokine (IFNγ and TNFα)-secretion capacity against CD38+ MM cells (CFSE assays). BLI based cytotoxicity assays will be used to measure the cytotoxic activity of CD38 CAR NK cells toward various luciferase transduced MM cell lines. We will also use NK cell susceptible K562 cell line as a target cell.

The CD38 dependent degranulation of NK cells upon stimulation with UM9 (high CD38) vs. U266 (CD38 negative) will be assayed by analyzing the up regulation of CD107a on the surface of ΔNGFR positive CAR NK cells using flow cytometry. The cytotoxic reactivity against primary MM cells will be assessed in FACS-based cytotoxicity assays using the BMMNCs derived from patients, as described earlier. Briefly, CD38 CAR NK cells will be co-cultured with the BMMNCs containing 5-50% MM cells at different effector to target ratios. 24 to 48 later, the survival of MM cells will be assessed by enumeration of CD138 positive plasma cells using quantitative flow cytometry. The cytotoxic activity will be deduced from these survival data as previously described.

In this phase of the research it is also important to determine the reactivity against non-malignant CD38 positive hematopoietic cells. This will be assessed by FACS-based cytotoxicity assays using PBMC or BMMNC of healthy individuals or patients. After co-incubation of CD38 CAR NK cells with PBMC or BMMNC for 24 to 48 hours, the survival of non-malignant hematopoietic cells, including CD34+ hematopoietic progenitor cells (only in BMMNC samples), CD3+ T cells, CD14+ Monocytes, CD56+ NK cells, CD19/20+ B cells will be determined in single platform quantitative FACS analyses. In all these assays, mock-vector transduced NK cells will be used as negative control, earlier-established CD38 CART cells will be used as positive controls.

Transduce the most optimal CD38 CAR NK-92 cell with TRAIL variant (TRAILv) and TRAIL wildtype (TRAILwt). Transduce the Most Optimal CD38 CAR KHYG-1 Cell with TRAILv and TRAIL wt.

The CD38 CAR NK cells that are best in killing MM cells without affecting normal CD38+ cells will be selected and further transduced with wild type TRAIL and TRAIL variant constructs. In a similar setting described above these cells will be tested against DR5+CD38+, DR5+CD38−, DR5−CD38+, DR5−, CD38− MM cell lines to compare their CD38 and DR-5 dependent cytotoxic activities and to compare their target cell specificity. Primary MM cells will also be studied for susceptibility against these cells. To generate the inducible TRAILv construct we will clone the TRAILv gene in a replication incompetent VSV-g pseudotyped self inactivating lentiviral construct under the control of a minimal (m)CMV promoter and tandem repeats of the NFAT transcriptional response element (TRE). By this way we will enable the rapid induction of the TRAILv upon CAR triggering, which induces gene expression under NFAT control. Consequently, upon CAR triggering, the CD3zeta domain activates NFAT which then will induce a rapid transcription and subsequent expression of TRAILv. The generated cells will be first evaluated for CD38 CAR dependent TRAILv Expression. After studying the on/off kinetics of this inducible gene, the cells will be, in a similar setting described above studied for the capacity of killing DR5+CD38+, DR5+CD38−, DR5−CD38+, DR5−, CD38− MM cell lines and primary MM cells.

Evaluate the Best CD38 CARs In Vivo Anti-MM Efficacy and MM vs Normal Hematopoietic Cell Discriminative Capacity In this stage we will determine the in vivo safety and anti-MM efficacy of the best CD38 CAR NK cells functioning in vitro. The in vivo activity of NK cells transduced with the best CD38 CAR (and TRAILv) will be assessed in our recently developed Rag2-/-γc-/--based xenograft model in which human MM tumors grow in a humanized microenvironment which is generated through the subcutaneous inoculation of scaffolds that are coated with human bone marrow derived MSCs. Briefly, in this model CD38 positive UM-9 and CD38 negative U266 MM tumors will be established in a humanized BM microenvironment. After demonstrating the engraftment of MM tumors in the humanized scaffolds by BLI (usually 1-2 weeks after inoculation), mice will be treated with iCasp9-CD38 CAR NK cells. The cells will be injected i.v. or intra-scaffold at escalating doses (a total dose of 3, 6 and 30×10$^6$ cells/mouse iv; 1,5, 3, 9×10$^6$ cells intra scaffold). The total CAR NK cell dose will be divided into three and each dose will be administered with one-week intervals. Tumor burden will be monitored by BLI. Mock-transduced NK cells and CD38 CART cells will be used as negative and positive controls, respectively.

Example 5—Protocol for Multiple Myeloma Therapy by CD38 CAR NK Cells Receptors As indicated above CD38 CAR NK cells can be administered to individuals with different types of cancer. The following protocol was developed for use in treating patients with multiple myeloma. Following diagnosis of a patient with a CD38 positive cancer, such as multiple myeloma, an aliquot of modified NK cells can be thawed and cultured prior to administration to the patient. Alternatively, a transient transfection can be prepared using lentivirus carrying a polynucleotide encoding a CD38 CAR, or electroporation with mRNA encoding a CAR, as described herein. For electroporation, the MaxCyte Flow Electroporation platform offers a suitable solution for achieving fast large-scale transfections in the clinic. After a CD38 CAR expressing NK cell is transfected it is cultured to allow for expression of the CAR and then administered i.v. to the patient.

Example 6—In Vitro Efficacy of TRAIL Variant Expressing NK Cells Against Multiple Myeloma and Acute Myelogenous Leukemia Multiple myeloma (MM), Acute Myeloid Leukemia (AML), and renal cell carcinoma (RCC) are debilitating and frequently fatal malignancies. RCC, MM and AML are susceptible to NK cell cytotoxicity via multiple effector pathways including NK cell TRAIL. Treatment of malignant cells with bortezomib upregulates DR5 expression on many malignancies and enhances their susceptibility to TRAIL-mediated apoptosis. Importantly, NK cells expanded ex vivo using EBV-LCL substantially upregulate surface expression of TRAIL, further augmenting NK cell mediated tumor killing of bortezomib-exposed tumors. Thus, genetic modification of NK cells to express the full length mutated DR5-specific TRAIL variant might enhance tumor specific cytotoxicity of NK cells independent of granule mediated cytotoxicity. Further, tumors exposed to bortezomib which upregulate DR5 would be predicted to become exquisitely sensitive to killing by these genetically modified NK cells.

In Vitro Experimental Plan

Ex vivo expanded NK cells (NK cells expanded using GMP conditions and the SMI-LCL feeder cell line) genetically modified to express DR-5 specific recombinant TRAIL (rhTRAIL D269H/E195R) will be examined to see if they can potentiate NK cell mediating killing against RCC, AML and MM tumor targets in vitro, and further, whether tumor killing can be improved by pretreating tumor targets with bortezomib. Tumor cytotoxicity experiments will be performed in vitro, using a Chromium Release Assay (CRA) and NK cell degranulation assays (CD107a), with ex vivo expanded NK cells against a panel of tumor cell lines know to express DR-5, which may be upregulated with bortezomib treatment. To identify if NK cell tumor killing is effected differently between NK cell populations tumor cytotoxicity assays utilizing different NK cell preparations will be performed. The populations include: a) freshly isolated NK cells; b) overnight IL-2 activated NK cells; c) 14 day ex vivo expanded NK cells using EBV-LCL feeder cells; d) 14 day ex vivo expanded NK cells mRNA electroporated using the Maxcyte GT system to express DR-5 specific recombinant TRAIL; and e) 14 day ex vivo expanded NK cells transduced using a lentiviral vector (LV) to express DR-5 specific recombinant TRAIL.

Various MOIs of transduction will be tested to optimize TRAIL surface expression. The goals will be to: a) define the kinetics of TRAIL surface expression over a 4 week period following NK cell transduction (in vitro); b) define the kinetics of NK cell tumor killing via TRAIL over multiple periods following NK cell transduction; c) valuate the effects of DR-5 specific TRAIL transduction on the phenotype, cytokine secretion potential, and functional cytotoxicity of NK cells; evaluate the effects of DR-5 specific TRAIL transduction on NK cell proliferation in vitro; and d) evaluate the effects of DR-5 specific TRAIL transduction on NK cell viability Various concentrations of mRNA encoding DR-5 specific recombinant TRAIL will be tested to optimize the transfection of NK cells to express recombinant TRAIL (in vitro). The goals will be to: a) define the kinetics of recombinant TRAIL expression over 4-7 days following mRNA transfection; b) compare these kinetics of TRAIL expression to NK cells transfected with mRNA encoding surface expressed CD34 as a control; c) define the kinetics of NK cell tumor killing via TRAIL following transfection of NK cells with DR-5 recombinant TRAIL over a one week period; d) evaluate the effects of DR-5 specific TRAIL mRNA transfection on the phenotype, cytokine secretion potential, and functional cytotoxicity of NK cells; e) evaluate the effects of DR-5 specific TRAIL mRNA transfection on NK cell proliferation in vitro; f) and evaluate the effects of DR-5 specific TRAIL mRNA transfection on NK cell viability We will also target NK cells (genetically manipulated vs. wild-type) against RCC, MM, and AML tumor target+/− being pretreated with bortezomib to upregulate tumor surface expression of the DR5 receptor.

In Vivo Experimental Plan

Next, ex-vivo expanded NK cells genetically modified to express DR-5 specific recombinant TRAIL will be examined to see if they can potentiate NK cell killing against RCC, AML and MM tumor targets in vivo. Ex vivo expanded NK cells genetically modified to express DR-5 specific recombinant TRAIL will be adoptively infused into MM1S tumor-bearing mice (NSG) to compare outcomes of untreated and treated mice using bioluminescence imaging (BLI). Conditions will include fresh, IL-2 activated, and expanded NK cells as well as expanded NK cells genetically modified to express DR-5 specific recombinant TRAIL via viral transduction and mRNA transfection. The same approach will be evaluated in the RCC with SAUJ-Luc and in AML in MOLM14-Luc tumor-bearing mice. Luciferase transduced tumor targets will allow us to use BLI imaging to evaluate tumor burden in these models.

Whether the timing of the treatment impacts the outcomes will be investigated. NK cells will be infused immediately following mRNA transfection versus delaying the infusion of NK cells following mRNA transfection until the time when surface expression of TRAIL peaks. The impact of exogenous IL-2 and/or IL-15 administration on in vivo NK cell killing of tumors will also be investigated. The impact of pretreating animals with bortezomib on tumor killing by NK cells genetically modified to express recombinant DR-5 specific TRAIL will be investigated. We will also evaluate the above in vivo experiments in MM and AML with ex vivo expanded NK cells genetically modified to express DR-5 using an expanded NK cell population that has either undergone; a) genetic modification; b) a culture modification; or c) ex vivo manipulation to have improved homing to the bone marrow.

Example 7—Knockout of Inhibitory Receptor Function

CRISPR/Cas9

Cells having inhibitory receptor function removed were prepared as follows. gRNA constructs were designed and prepared to target genes encoding the 'classical' inhibitory receptor LIR2 and the 'checkpoint' inhibitory receptor CTLA4 in the human genome of NK cells. CRISPR/Cas9 genome editing was then used to knock out the LIR2 and CTLA4 target genes.

Two gRNA candidates were selected for each target gene and their cleavage efficacies in K562 cells determined. The sequences of the gRNA candidates are shown in Table 1.

TABLE 1 gRNA candidates and sequences

| Gene | Plasmid Name | Sequence |
| --- | --- | --- |
| hLIR2 | SM682.LIR2.g9 | GAGTCACAGGTGGCATTTGGCGG (SEQ ID NO: 24) |
|  | SM682.LIR2.g18 | CGAATCGCAGGTGGTCGCACAGG (SEQ ID NO: 25) |
| hCTLA4 | SM683.CTLA4.g7 | CACTCACCTTTGCAGAAGACAGG (SEQ ID NO: 26) |
|  | SM683.CTLA4.g15 | CCTTGTGCCGCTGAAATCCAAGG (SEQ ID NO: 27) |

Figure 5:
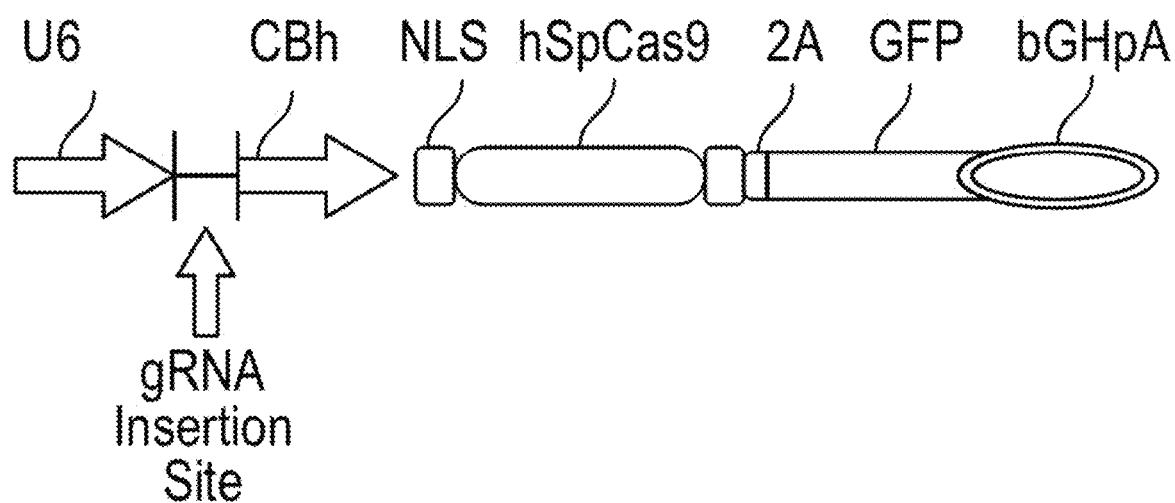
FIG. 5 illustrates a gRNA construct (expression vector) used to target deletion of CTLA4.

K562 cells were transfected with the prepared gRNA constructs (FIG. 5) and subsequently harvested for PCR amplification. The presence of GFP expression was used to report successful incorporation of the gRNA construct into the K562 cells. This confirmed expression of the Cas9 gene and therefore the ability to knock out expression of the LIR2 and CTLA4 genes. The cleavage activity of the gRNA constructs was determined using an in vitro mismatch detection assay. T7E1 endonuclease I recognizes and cleaves non-perfectly matched DNA, allowing the parental LIR2 and CTLA4 genes to be compared to the mutated genes following CRISPR/Cas9 transfection and non-homologous end joining (NHEJ).

Figure 6:
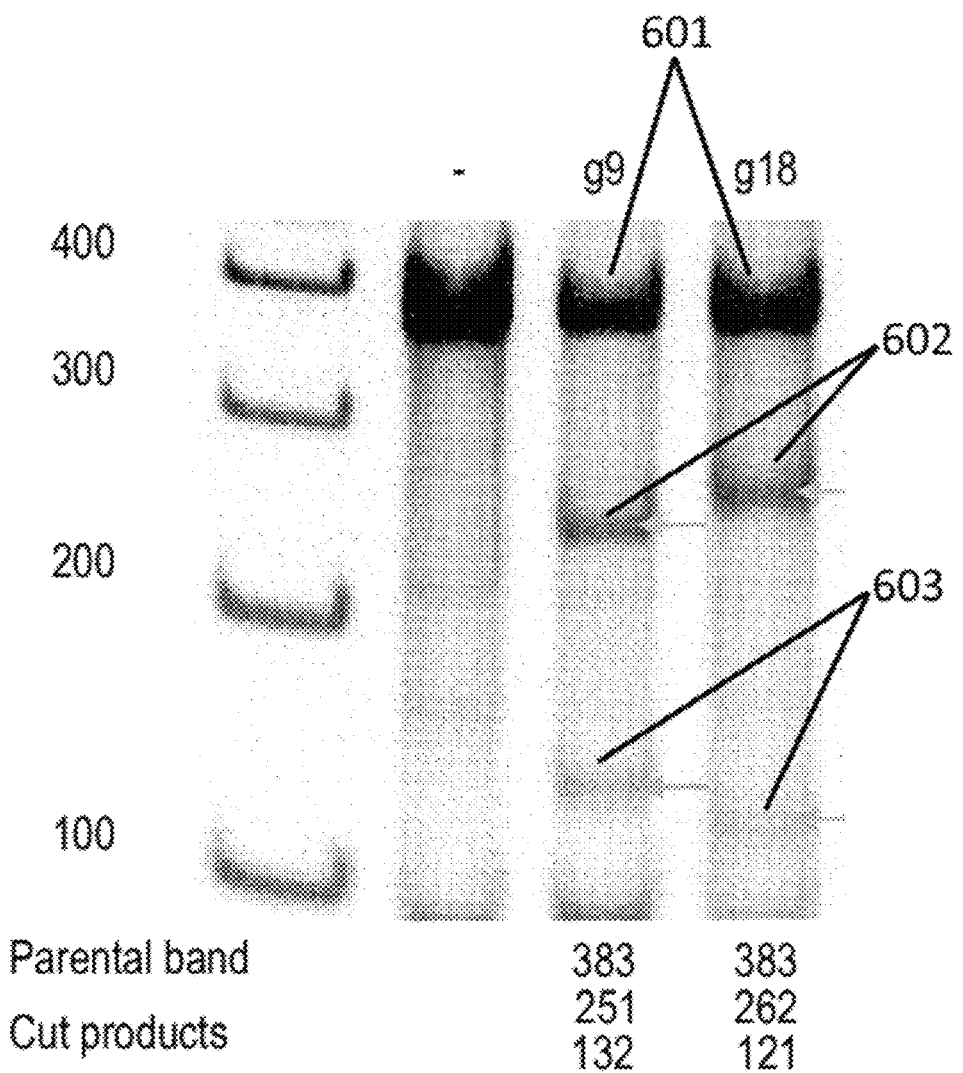
FIG. 6 illustrates gel electrophoresis bands for parental and mutated LIR2 DNA, before and after transfection with CRISPR/Cas9 gRNA.

FIG. 6 shows the resulting bands following agarose gel electrophoresis after knockout of the LIR2 gene with the g9 and g18 gRNA sequences. The three bands corresponding to each mutation relate to the parental gene (601) and the two resulting strands following detection of a mismatch in the DNA sequence after transfection (602 and 603). The g9 gRNA sequence resulted in an 11% success rate of transfection, whereas the g18 gRNA resulted in 10%.

Figure 7:
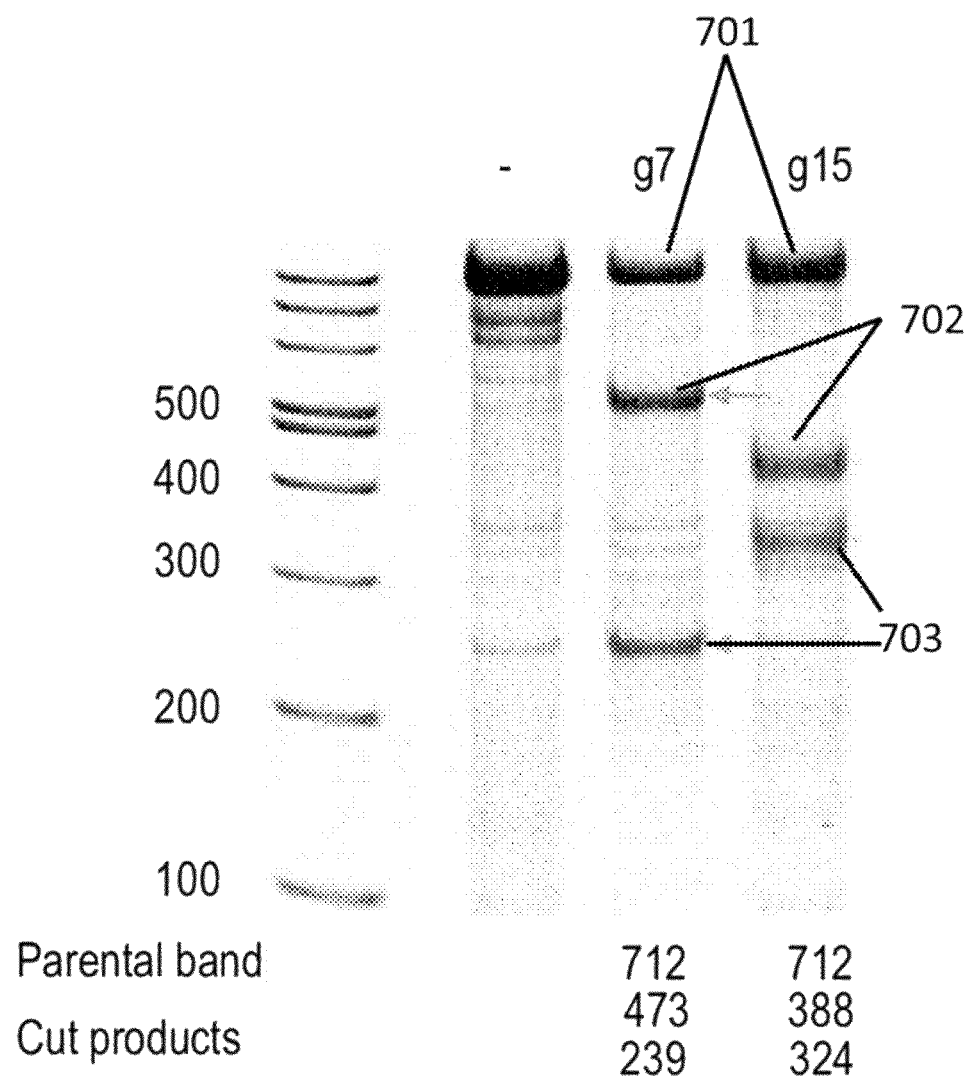
FIG. 7 illustrates gel electrophoresis bands for parental and mutated CTLA4 DNA, before and after transfection with CRISPR/Cas9 gRNA.

FIG. 7 shows the resulting bands following agarose gel electrophoresis after knockout of the CTLA4 gene with the g7 and g15 gRNA sequences. 701 shows the parental bands and 702; 703 show the two resulting bands after mismatch detection. The g7 gRNA sequence resulted in a 32% success rate of transfection, whereas the g15 gRNA resulted in 26%.

Following the successful knockout of LIR2 and CTLA4 in K562 cells, KHYG-1 cells were transfected with gRNA constructs. KHYG-1 derivative clones having homozygous deletions were selected. A Cas9/puromycin acetyltransferase (PAC) expression vector was used for this purpose. Successfully transfected cells were selected, based on their resistance to the antibiotic puromycin.

Cas9 RNP

Another protocol used for knockout of checkpoint inhibitory receptors in NK cells was that of Cas9 RNP transfection. An advantage of using this protocol was that similar transfection efficiencies were achievable but with significantly lower toxicity compared to using the DNA plasmids of the CRISPR/Cas9 protocol. 1×10⁶ KHYG1 cells were harvested for each transfection experiment. The cells were washed with PBS and spun down in a centrifuge. The supernatant was then discarded. The CRISPR RNP (RNA binding protein) materials were then prepared as follows: (1) a 20 μM solution of the required synthesized crRNA and tRNA (purchased from Dharmacon) was prepared; (2) 4 μl of crRNA (20 μM) and 4 μl of tRNA (20 μM) were mixed together; (3) the mixture was then added to 2 μl Cas9 protein (5 μg/μl); (4) all of the components were mixed and incubated at room temperature for 10 minutes. Following the Neon® Transfection System, the cells were mixed with Cas9 RNP and electroporation was performed using the following parameters: Voltage: 1450v; pulse width, 30 ms; pulse number: 1. The cells were then transferred to one well of a 12-well plate containing growth medium (including IL-2 and IL-15). The cells were harvested after 48-72 hours to confirm gene editing efficiency by T7 endonuclease assay and/or Sanger sequencing. The presence of indels were confirmed, indicating successful knockout of CTLA4, PD1 and CD96 in KHYG1 cells.

Site-Specific Nucleases

Another protocol used for knockout of checkpoint inhibitory receptors in NK cells was that of XTN TALEN transfection. An advantage of using this protocol was that a particularly high level of specificity was achievable compared to wildtype CRISPR Step 1: Preparation of Reagents KHYG-1 cells were assayed for certain attributes including transfection efficiency, single cell cloning efficiency and karyotype/copy number. The cells were then cultured in accordance with the supplier's recommendations. Depending on the checkpoint inhibitory receptor being knockout out, nucleases were prepared by custom-design of at least 2 pairs of XTN TALENs. The step of custom-design includes evaluation of gene locus, copy number and functional assessment (i.e. homologs, off-target evaluation).

Step 2: Cell Line Engineering

The cells were transfected with the nucleases of Step 1; this step was repeated up to 3 times in order to obtain high levels of cutting and cultures were split and intermediate cultures maintained prior to each transfection. Initial screening occurred several days after each transfection; the pools of cells were tested for cutting efficiency via the Cel-1 assay. Following the level of cutting reaching acceptable levels or plateaus after repeated transfections, the cells were deemed ready for single cell cloning. The pooled cells were sorted to one cell per well in a 96-well plate; the number of plates for each pool was dependent on the single cell cloning efficiency determined in Step 1. Plates were left to incubate for 3-4 weeks.

Step 3: Screening and Expansion

Once the cells were confluent in the 96-well plates, cultures were consolidated and split into triplicate 96-well plates; one plate was frozen as a backup, one plate was re-plated to continue the expansion of the clones and the final plate was used for genotype confirmation. Each clone in the genotype plate was analyzed for loss of qPCR signal, indicating all alleles had been modified. Negative clones were PCR amplified and cloned to determine the nature of the indels and lack of any wildtype or in-frame indels. Clones with the confirmed knockout were consolidated into no more than one 24-well plate and further expanded; typically 5-10 frozen cryovials containing 1×10⁶ cells per vial for up to 5 individual clones were produced per knockout.

Step 4: Validation

Cells were banked under aseptic conditions. Basic release criteria for all banked cells included viable cell number (pre-freeze and post-thaw), confirmation of identity via STR, basic sterility assurance and *mycoplasma* testing; other release criteria were applied when necessary (karyotype, surface marker expression, high level sterility, knockout evaluation of transcript or protein, etc).

Example 8—Knockdown of Checkpoint Inhibitory Receptor CD96 Function Via RNAi siRNA knockdown of CD96 in KHYG-1 cells was performed by electroporation. The Nucleofection Kit was used, in conjunction with the Amaxa Nucleofector II, from Lonza, as it is appropriate for use with cell lines and can successfully transfect both dividing and non-dividing cells and achieves transfection efficiencies of up to 90%. Control siRNA (catalog number: sc-37007) and CD96 siRNA (catalog number: sc-45460) were obtained from Santa Cruz Biotechnology. Antibiotic-free RPMI-1640 containing 10% FBS, 2 mM L-glutamine was used for post-Nucleofection culture. Mouse anti-human CD96-APC (catalog number: 338409) was obtained from Biolegend for staining.

A 20 μM of siRNA stock solution was prepared. The lyophilized siRNA duplex was resuspended in 341 of the RNAse-free water (siRNA dilution buffer: sc-29527) to FITC-control/control-siRNA, in 165 μl of the RNAse-free water for the target gene siRNA (siRNA CD96). The tube was heated to 90° C. for 1 minute and then incubated at 37° C. for 60 minutes. The siRNA stock was then stored at −20° C. until needed.

Figure 8A:
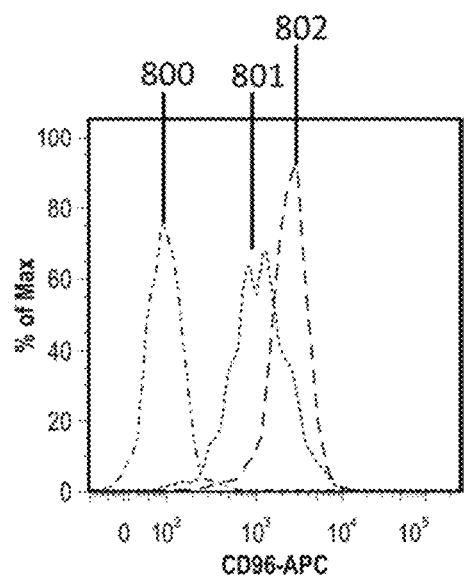
FIGS. 8A-B illustrate knockdown of CD96 in KHYG-1 cells using siRNA as analyzed by flow cytometry. Two independent experiments are shown (A and B).
Figure 8B:
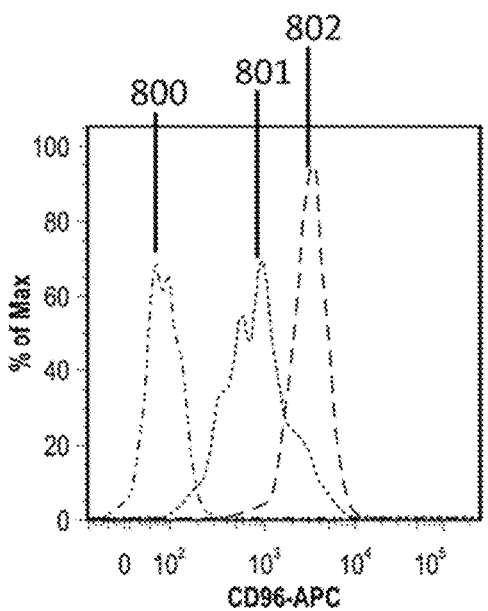

The KHYG-1 cells were passaged one to two days before Nucleofection, as the cells must be in logarithmic growth phase. The Nucleofector solution was warmed to room temperature (100 ul per sample). An aliquot of culture medium containing serum and supplements was also pre-warmed at 37° C. in a 50 ml tube. 6-well plates were prepared by adding 1.5 ml of culture medium containing serum and supplements. The plates were pre-incubated in a humidified 37° C./5% $CO_2$ incubator. $2 \times 10^6$ cells in 100 μl Nucleofection solution was mixed gently with 4 μl 20 μM siRNA solution (1.5 μg siRNA). Air bubbles were avoided during mixing. The mixture was transferred into Amaxa certified cuvettes and placed into the Nucleofector cuvette holder and program U-001 selected. The program was allowed to finish, and the samples in the cuvettes were removed immediately. 500 μl pre-equilibrated culture medium was then added to each cuvette. The sample in each cuvette was then gently transferred to a corresponding well of the prepared 6-well plate, in order to establish a final volume of 2 ml per well. The cells were then incubated in a humidified 37° C./5% $CO_2$ incubator until transfection analysis was performed. Flow cytometry analysis was performed 16-24 hours after electroporation, in order to measure CD96 expression levels. This electroporation protocol was carried out multiple times. FIGS. 8A and 8B show that this protocol resulted in reliable CD96 knockdown 801 (Mean fluorescence intensity of 1107 in 8A; 810 in 8B) compared to KHYG-1 cells transfected with control siRNA 802 (Mean fluorescence intensity of 2409 in 8A; 3002 in 8B). Isotype is shown by 800 802 (Mean fluorescence intensity of 90 in 8A; 76 in 8B).

Example 9—Enhanced Cytotoxicity of NK Cells with a CD96 Knockdown

Figure 9:
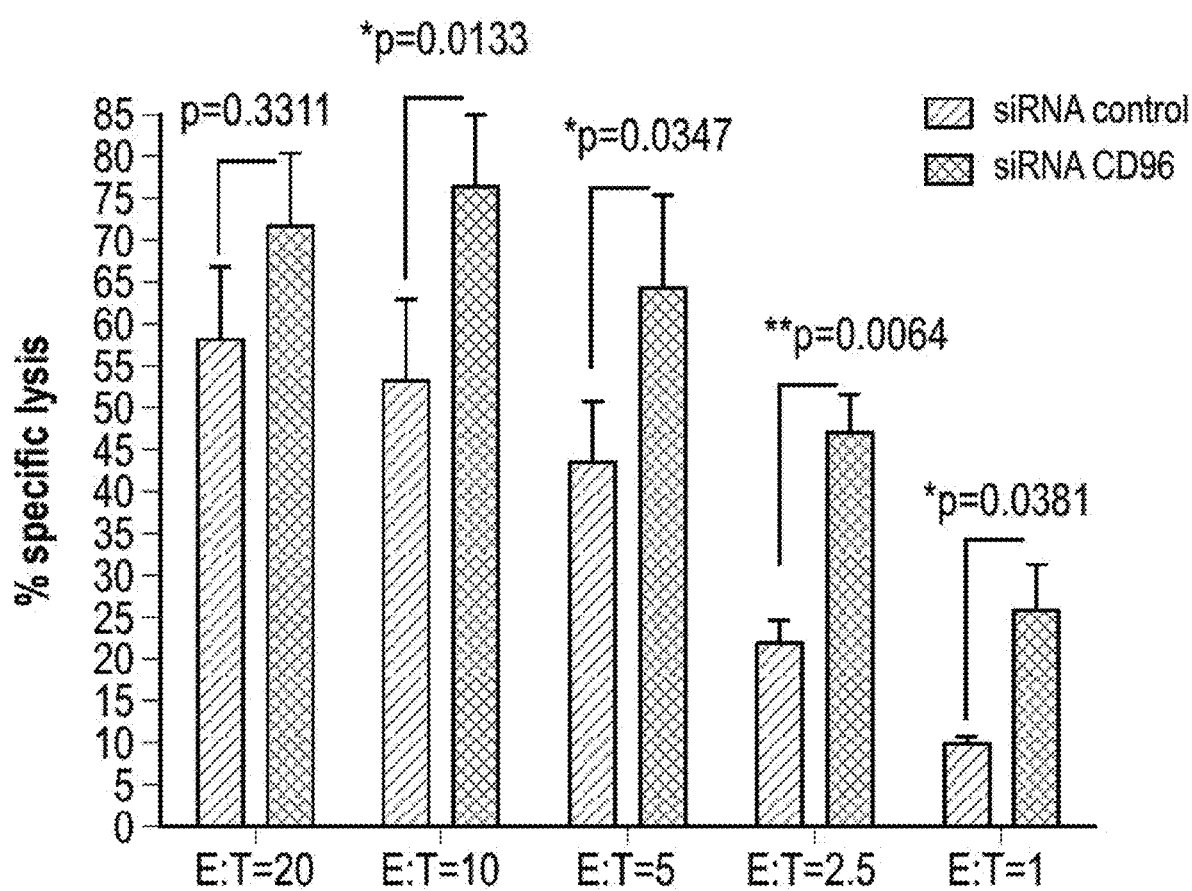
FIG. 9 illustrates increased killing by KHYG-1 cells with CD96 reduction at different effector to target ratios.

KHYG-1 cells with and without the CD96 knockdown were co-cultured with K562 cells at different effector: target (E:T) ratios. Cytotoxicity was measured 4 hours after co-culture, using the DELFIA EuTDA Cytotoxicity Kit from PerkinElmer (Catalog number: AD0116). Target cells K562 were cultivated in RPMI-1640 medium containing 10% FBS, 2 mM L-glutamine and antibiotics. 96-well V-bottom plates (catalog number: 83.3926) were bought from SARSTEDT. An Eppendorf centrifuge 5810R (with plate rotor) was used to spin down the plate. A VARIOSKAN FLASH (with Scanit software 2.4.3) was used to measure the fluorescence signal produced by lysed K562 cells. K562 cells were washed with culture medium and the number of cells adjusted to $1 \times 10^6$ cells/mL with culture medium. 2-4 mL of cells was added to 5 μl of BATDA reagent and incubated for 10 minutes at 37° C. Within the cell, the ester bonds are hydrolyzed to form a hydrophilic ligand, which no longer passes through the membrane. The cells were centrifuged at 1500 rpm for 5 mins to wash the loaded K562 cells. This was repeated 3-5 times with medium containing 1 mM Probenecid (Sigma P8761). After the final wash the cell pellet was resuspended in culture medium and adjusted to about $5 \times 10^4$ cells/mL. Wells were set up for detection of background, spontaneous release and maximum release. 100 μL, of loaded target cells (5,000 cells) were transferred to wells in a V-bottom plate and 100 μL, of effector cells (KHYG-1 cells) were added at varying cell concentrations, in order to produce effector to target ratios ranging from 1:1 to 20:1. The plate was centrifuged at 100×g for 1 minute and incubated for 4 hours in a humidified 5% $CO_2$ atmosphere at 37° C. For maximum release wells 104, of lysis buffer was added to each well 15 minutes before harvesting the medium. The plate was centrifuged at 500×g for 5 minutes. 20 μL, of supernatant was transferred to a flat-bottom 96 well plate 2004, of pre-warmed Europium solution added. This was incubated at room temperature for 15 mins using a plate shaker. As K562 cells are lysed by the KHYG-1 cells, they release ligand into the medium. This ligand then reacts with the Europium solution to form a fluorescent chelate that directly correlates with the amount of lysed cells. The fluorescence was then measured in a time-resolved fluorometer by using VARIOSKAN FLASH. The specific release was calculated using the following formula: % specific release=Experiment release−Spontaneous release/Maximum release−Spontaneous release. Statistical analysis was performed using Graphpad Prism 6.04 software. A paired t test was used to compare the difference between siRNA CD96 knockdown KHYG-1 cells and control groups (n=3). The specific release was found to be significantly increased in co-cultures containing the CD96 knockdown KHYG-1 cells. This was the case at all E:T ratios (see FIG. 9). As fluorescence directly correlates with cell lysis, it was confirmed that knocking down CD96 expression in KHYG-1 cells resulted in an increase in their ability to kill K562 cancer target cells.

Example 10—Enhanced Cytotoxicity of NK Cells with a CD328 (Siglec-7) Knockdown SiRNA-Mediated Knock-Down of CD328 in NK-92 Cells Materials, Reagents and Instruments Control siRNA (catalog number: sc-37007) and CD328 siRNA (catalog number: sc-106757) were bought from Santa Cruz Biotechnology. To achieve transfection efficiencies of up to 90% with high cell viability (>75%) in NK-92 cells with the Nucleofector™ Device (Nucleofector II, Lonza), a Nucleofector™ Kit T from Lonza was used. RPMI-1640 containing 10% FBS, 2 mM L-glutamine, antibiotics free, was used for post-Nucleofection culture. Mouse anti-human CD328-APC (catalog number: 339206) was bought from Biolegend.

Protocol

To make 10 μM of siRNA stock solution. Resuspend lyophilized siRNA duplex in 66 μl of the RNAse-free water (siRNA dilution buffer: sc-29527) to FITC-control/control-siRNA, in 330 μl of the RNAse-free water for the target gene siRNA (siRNA CD328). Heat the tube to 90° C. for 1 minute. Incubate at 37° C. for 60 minutes. Store siRNA stock at −20° C. if not used directly. One Nucleofection sample contains (for 100 μl standard cuvette). Cell number: $2 \times 10^6$ cells. siRNA: 4 μl of 10 μM stock. Nucleofector solution: 100 μl.

Nucleofection

Cultivate the required number of cells. (Passage one or two day before Nucleofection, cells must be in logarithmic growth phase). Prepare siRNA for each sample. Pre-warm the Nucleofector solution to room temperature (100 μl per sample). Pre-warm an aliquot of culture medium containing serum and supplements at 37° C. in a 50 ml tube. Prepare 6-well plates by filling with 1.5 ml of culture medium containing serum and supplements and pre-incubate plates in a humidified 37° C./5% $CO_2$ incubator. Take an aliquot of cell culture and count the cells to determine the cell density. Centrifuge the required number of cells at 1500 rpm for 5 min. Discard supernatant completely so that no residual medium covers the cell pellet. Resuspend the cell pellet in room temperature Nucleofector Solution to a final concentration of $2 \times 10^6$ cells/100 μl. Avoid storing the cell suspension longer than 15-20 min in Nucleofector Solution, as this reduces cell viability and gene transfer efficiency. Mix 100 μl of cell suspension with siRNA. Transfer the sample into an Amaxa certified cuvette. Make sure that the sample covers the bottom of the cuvette, avoid air bubbles while pipetting. Close the cuvette with the blue cap. Select the appropriate Nucleofector program (A-024 for NK-92 cells). Insert the cuvette into the cuvette holder (Nucleofector II: rotate the carousel clockwise to the final position) and press the "x" button to start the program. To avoid damage to the cells, remove the samples from the cuvette immediately after the program has finished (display showing "OK"). Add 500 μl of the pre-warmed culture medium into the cuvette and transfer the sample into the prepared 6-well plate. Incubate cells in a humidified 37° C./5% $CO_2$ incubator. Perform flow cytometric analysis and cytotoxicity assay after 16-24 hours.

Results

Figure 10:
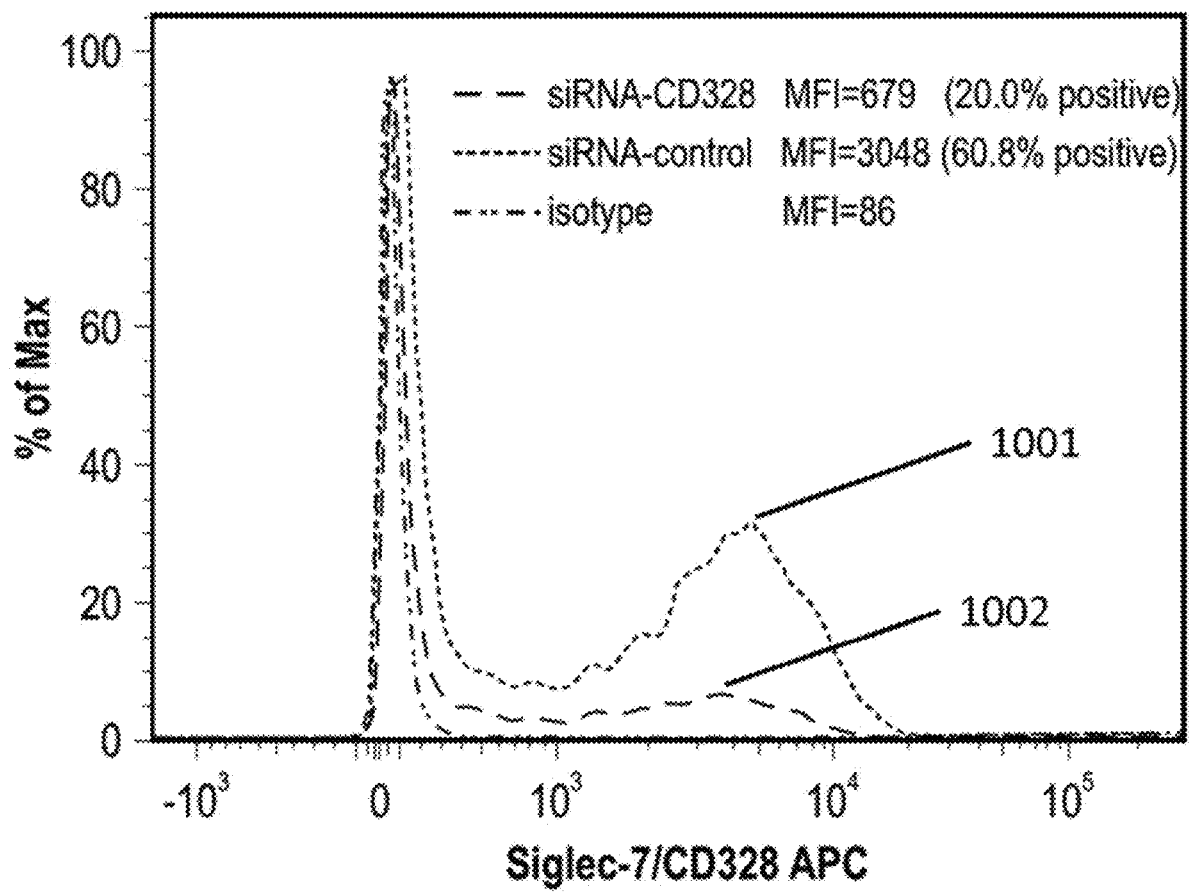
FIG. 10 illustrates knockdown of CD328 in KHYG-1 cells using siRNA as analyzed by flow cytometry.

We followed the above protocol and performed flow cytometry analysis of CD328 expression level in NK-92 cells. The results of one representative experiment is shown in FIG. 10, confirming successful knockdown (Mean fluorescence intensity of 3048 for control siRNA 1001; 679 for CD328 siRNA 1002.

Knocking Down CD328 Enhances Cytotoxicity

Materials, Reagents and Instruments

DELFIA EuTDA cytotoxicity kit based on fluorescence enhancing ligand (Catalog number: AD0116) was bought from PerkinElmer. Target cells K562 were cultivated in RPMI-1640 medium containing 10% FBS, 2 mM L-glutamine and antibiotics. 96-well V-bottom plates (catalog number: 83.3926) were bought from SARSTEDT. Eppendorf centrifuge 5810R (with plate rotor) was used to spin down the plate. VARIOSKAN FLASH (with ScanIt software 2.4.3) was used to measure the fluorescence signal produced by lysed K562 cells.

Protocol

Load target K562 cells with the fluorescence enhancing ligand DELFIA BATDA reagent Wash K562 cells with medium, adjust the number of cells to $1 \times 10^6$ cells/mL with culture medium. Add 2-4 mL of cells to 5 μl of BATDA reagent, incubate for 10 minutes at 37° C. Spin down at 1500 rpm for 5 minutes to wash the loaded K562 cells for 3-5 times with medium containing 1 mM Probenecid (Sigma P8761). After the final wash resuspend the cell pellet in culture medium and adjust to about $5 \times 10^4$ cells/mL.

Cytotoxicity Assay

Figure 11:
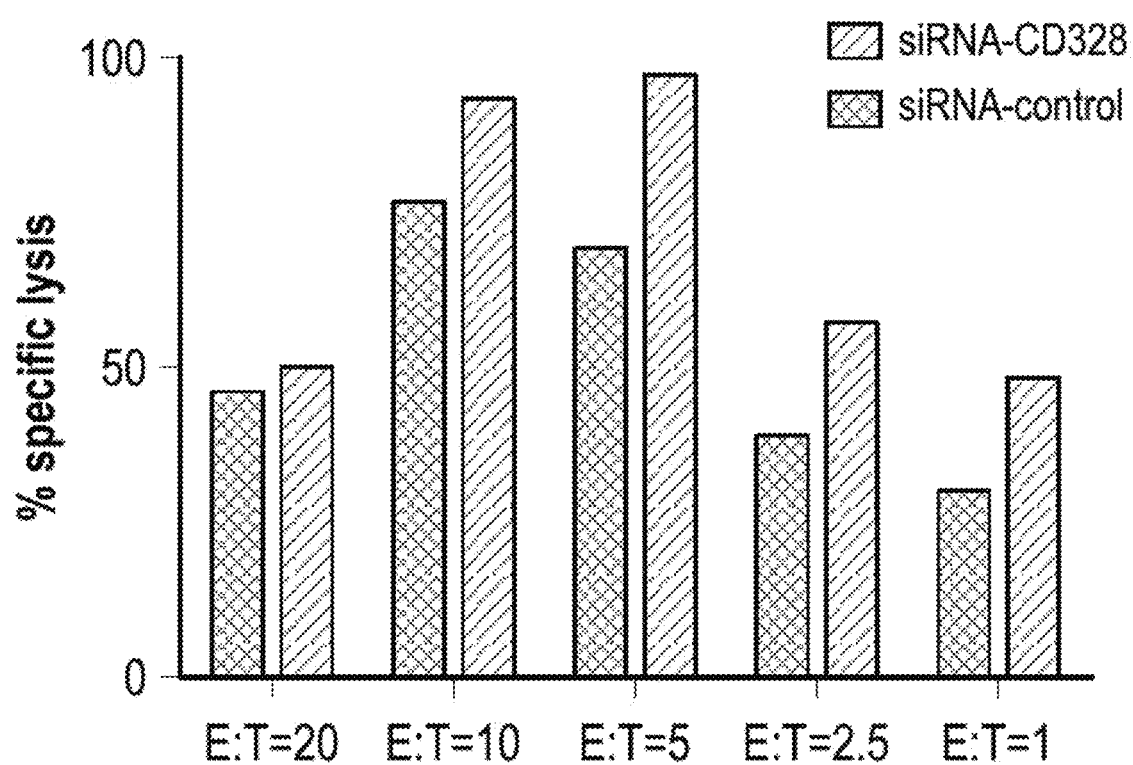
FIG. 11 illustrates increased killing by KHYG-1 cells with CD328 reduction at different effector to target ratios.

Set up wells for detection of background, spontaneously release and maximum release. Pipette 100 μL, of loaded target cells (5,000 cells) to a V-bottom plate. Add 100 μL, of effector cells (NK-92) of varying cell concentrations. Effector to target ratio ranges from 1:1 to 20:1. Spin down the plate at 100×g of RCF for 1 minute. Incubate for 2 hours in a humidified 5% $CO_2$ atmosphere at 37° C. For maximum release wells, add 10 μL of lysis buffer to each well 15 minutes before harvesting the medium. Spin down the plate at 500×g for 5 minutes. Transfer 20 μL of supernatant to a flat-bottom 96 well plate, add 200 μL of pre-warmed Europium solution, incubate at room temperature for 15 minutes using plate shaker. Measure the fluorescence in a time-resolved fluorometer by using VARIOSKAN FLASH. The specific release was calculated using the following formula:
% specific release=Experiment release−Spontaneous release/Maximum release−Spontaneous release Results We followed the above to determine the effect on cytotoxicity of the CD328 knockdown. The results of one representative experiment are shown in FIG. 11. As seen, cytotoxicity against target cells was increased in cells with the CD328 knockdown.

Example 11—Protocol for Blood Cancer Therapy by Knockdown/Knockout of Checkpoint Inhibitory Receptors As demonstrated in the above Examples, checkpoint inhibitory receptor function can be knocked down or knocked out in a variety of ways. The following protocol was developed for use in treating patients with blood cancer: Following diagnosis of a patient with a cancer suitably treated with the invention, an aliquot of modified NK cells can be thawed and cultured prior to administration to the patient. Alternatively, a transient mutation can be prepared using e.g. siRNA within a day or two, as described above. The MaxCyte Flow Electroporation platform offers a suitable solution for achieving fast large-scale transfections in the clinic. The removal of certain checkpoint inhibitory receptors may be more beneficial than others. This is likely to depend on the patient and the cancer. For this reason, the cancer is optionally biopsied and the cancer cells are grown in culture ex vivo. A range of NK cells with different checkpoint inhibitory receptor modifications can thus be tested for cytotoxicity against the specific cancer. This step can be used to select the most appropriate NK cell or derivative thereof for therapy. Following successful modification, the cells are resuspended in a suitable carrier (e.g. saline) for intravenous and/or intratumoral injection into the patient.

Example 12-KHYG-1 Knock-in of TRAIL/TRAIL Variant

KHYG-1 cells were transfected with both TRAIL and TRAIL variant, in order to assess their viability and ability to kill cancer cells following transfection. The TRAIL variant used is that described in WO 2009/077857. It is encoded by the wildtype TRAIL gene containing the D269H/E195R mutation. This mutation significantly increases the affinity of the TRAIL variant for DR5, whilst reducing the affinity for both decoy receptors (DcR1 and DcR2).

Baseline TRAIL Expression

Figure 12:
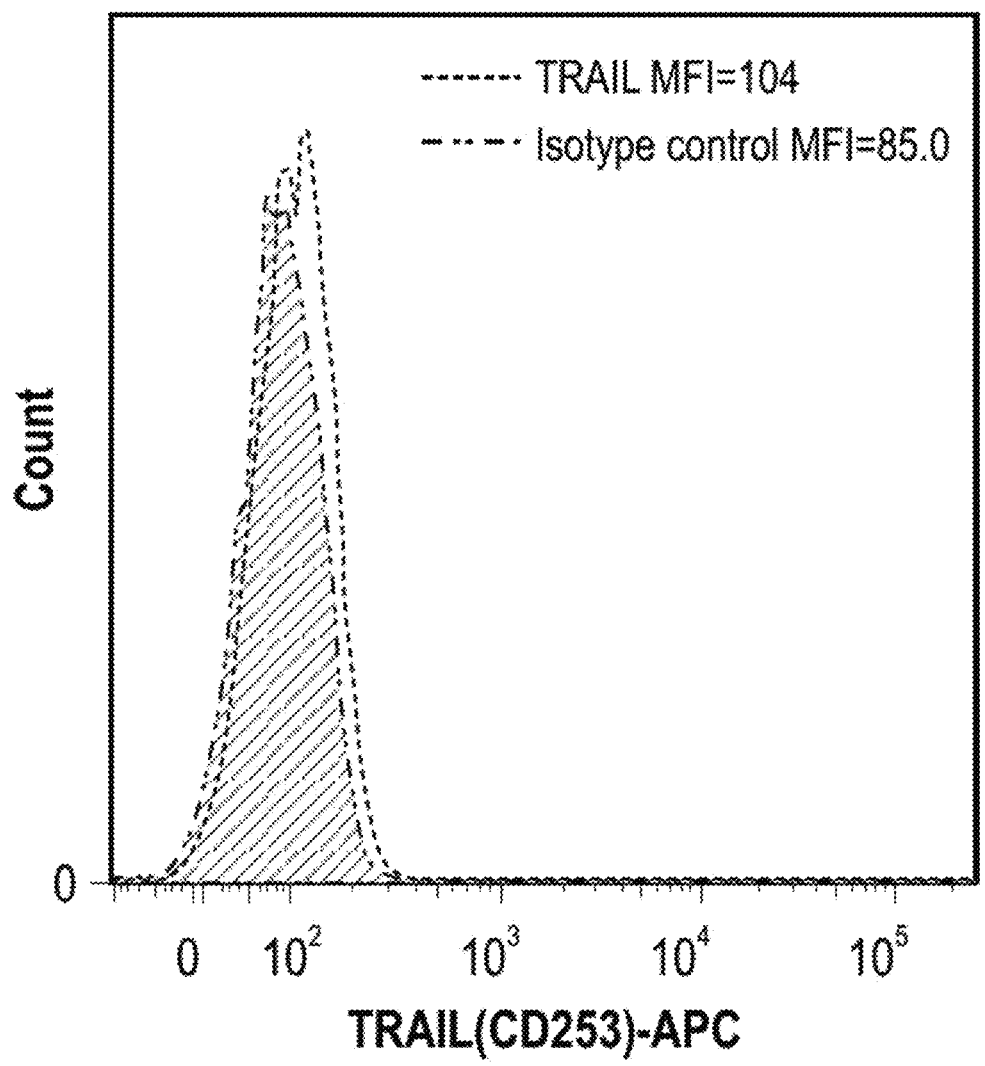
FIG. 12 illustrates that KHYG-1 cells exhibit low or absent expression of TRAIL as analyzed by flow cytometry.

Baseline TRAIL (CD253) expression in KHYG-1 cells was assayed using flow cytometry. Mouse anti-human CD253-APC (Biolegend catalog number: 308210) and isotype control (Biolegend catalog number: 400122) were used to stain cell samples and were analyzed on a BD FACS Canto II flow cytometer. KHYG-1 cells were cultured in RPMI 1640 medium containing 10% FBS, 2 mM L-glutamine, penicillin (100 U/mL)/streptomycin (100 mg/mL) and IL-2 (long/mL). $0.5\text{-}1.0\times10^6$ cells/test were collected by centrifugation (1500 rpm×5 minutes) and the supernatant was aspirated. The cells (single cell suspension) were washed with 4 mL ice cold FACS Buffer (PBS, 0.5-1% BSA, 0.1% NaN3 sodium azide). The cells were re-suspended in 100 µL ice cold FACS Buffer, add 5 uL antibody was added to each tube and incubated for 30 minutes on ice. The cells were washed 3 times by centrifugation at 1500 rpm for 5 minutes. The cells were then re-suspended in 500 µL ice cold FACS Buffer and temporarily kept in the dark on ice. The cells were subsequently analyzed on the flow cytometer (BD FACS Canto II) and the generated data were processed using FlowJo 7.6.2 software. As can be seen in FIG. 12, FACS analysis showed weak baseline expression of TRAIL on the KHYG-1 cell surface.

TRAIL/TRAIL Variant Knock-in by Electroporation

Wildtype TRAIL mRNA and TRAIL variant (D269H/195R) mRNA was synthesized by TriLink BioTechnologies, aliquoted and stored as −80° C. Mouse anti-human CD253-APC (Biolegend catalog number: 308210) and isotype control (Biolegend catalog number: 400122), and Mouse anti-human CD107a-PE (eBioscience catalog number: 12-1079-42) and isotype control (eBioscience catalog number: 12-4714) antibodies were used to stain cell samples and were analyzed on a BD FACS Canto II flow cytometer. DNA dye SYTOX-Green (Life Technologies catalog number: 57020; 5 mM Solution in DMSO) was used. To achieve transfection efficiencies of up to 90% with high cell viability in KHYG-1 cells with the Nucleofector™ Device (Nucleofector II, Lonza), a Nucleofector™ Kit T from Lonza was used. Antibiotics-free RPMI 1640 containing 10% FBS, L-glutamine (2 mM) and IL-2 (10 ng/mL) was used for post-Nucleofection culture.

Figure 13:
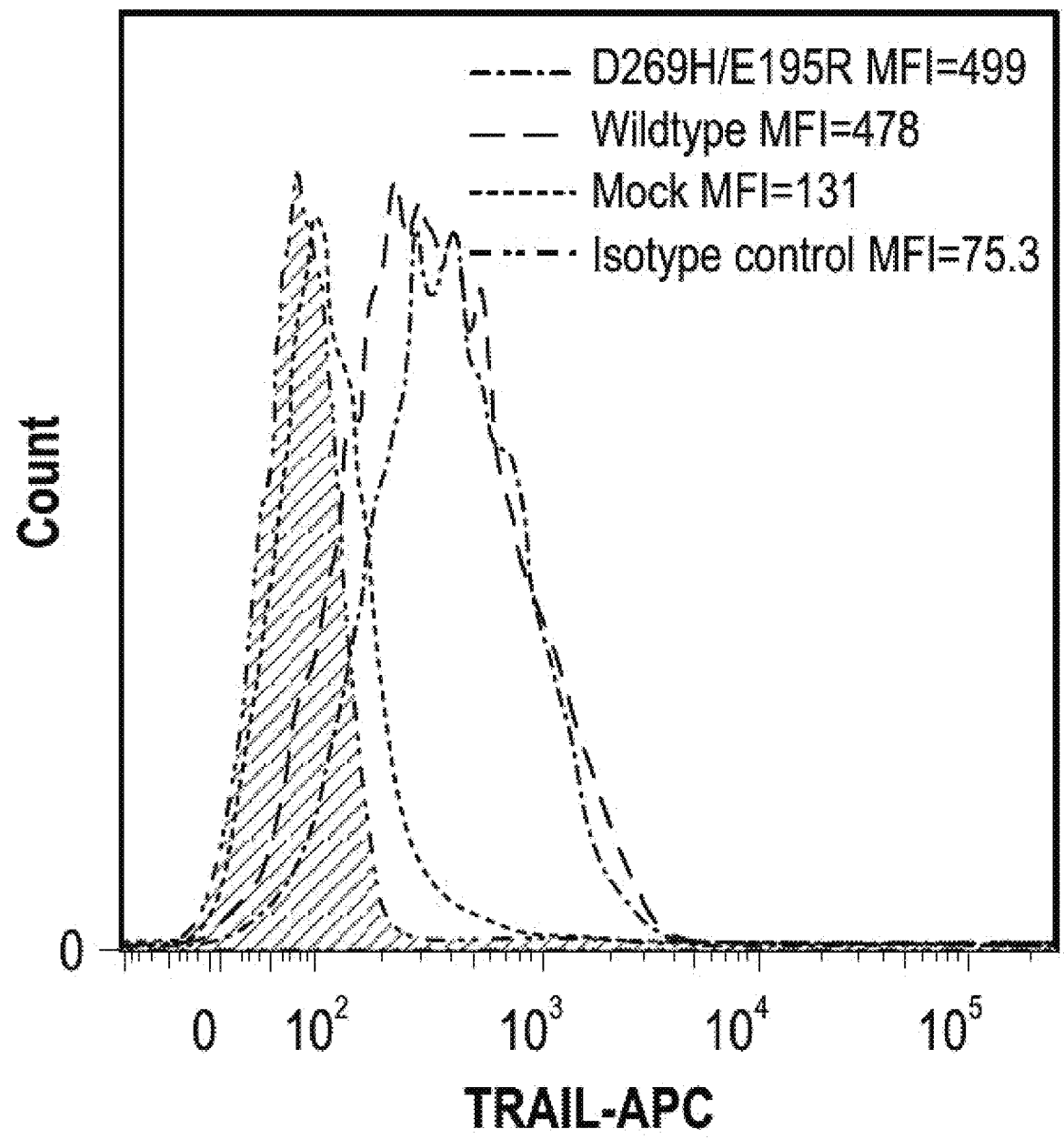
FIG. 13 illustrates increased cell-surface TRAIL expression in cells transfected with wildtype and variant TRAIL as analyzed by flow cytometry.
Figure 14:
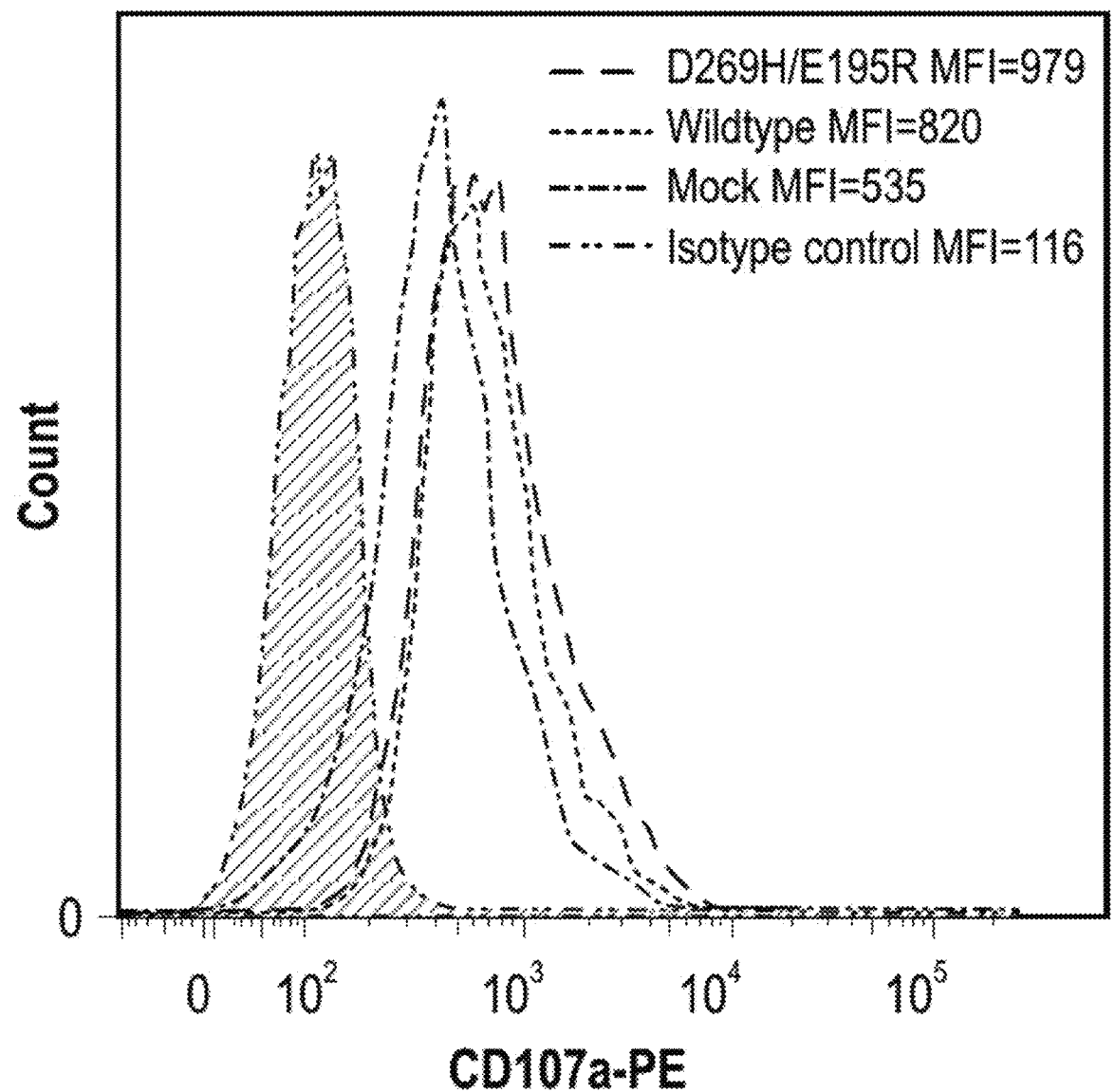
FIG. 14 illustrates increased cell-surface 107a expression in cells transfected with wildtype and variant TRAIL as analyzed by flow cytometry.

KHYG-1 and NK-92 cells were passaged one or two days before Nucleofection, as the cells must be in the logarithmic growth phase. The Nucleofector solution was pre-warmed to room temperature (100 µl per sample), along with an aliquot of culture medium containing serum and supplements at 37° C. in a 50 mL tube. 6-well plates were prepared by filling with 1.5 mL culture medium containing serum and supplements and pre-incubated in a humidified 37° C./5% $CO_2$ incubator. An aliquot of cell culture was prepared and the cells counted to determine the cell density. The required number of cells was centrifuged at 1500 rpm for 5 min, before discarding the supernatant completely. The cell pellet was re-suspended in room temperature Nucleofector Solution to a final concentration of $2\times10^6$ cells/100 µl (maximum time in suspension=20 minutes). 100 µl cell suspension was mixed with 10 µg mRNA (volume of RNA<10 The sample was transferred into an Amaxa-certified cuvette (making sure the sample covered the bottom of the cuvette and avoiding air bubbles). The appropriate Nucleofector program was selected (i.e. U-001 for KHYG-1 cells). The cuvettes were then inserted into the cuvette holder. 500 µl pre-warmed culture medium was added to the cuvette and the sample transferred into a prepared 6-well plate immediately after the program had finished, in order to avoid damage to the cells. The cells were incubated in a humidified 37° C./5% $CO_2$ incubator. Flow cytometric analysis and cytotoxicity assays were performed 12-16 hours after electroporation. Flow cytometry staining was carried out as above. As can be seen in FIGS. 13 and 14, expression of TRAIL/TRAIL variant and CD107a (NK activation marker) increased post-transfection, confirming the successful knock-in of the TRAIL genes into KHYG-1 cells.

Figure 15:
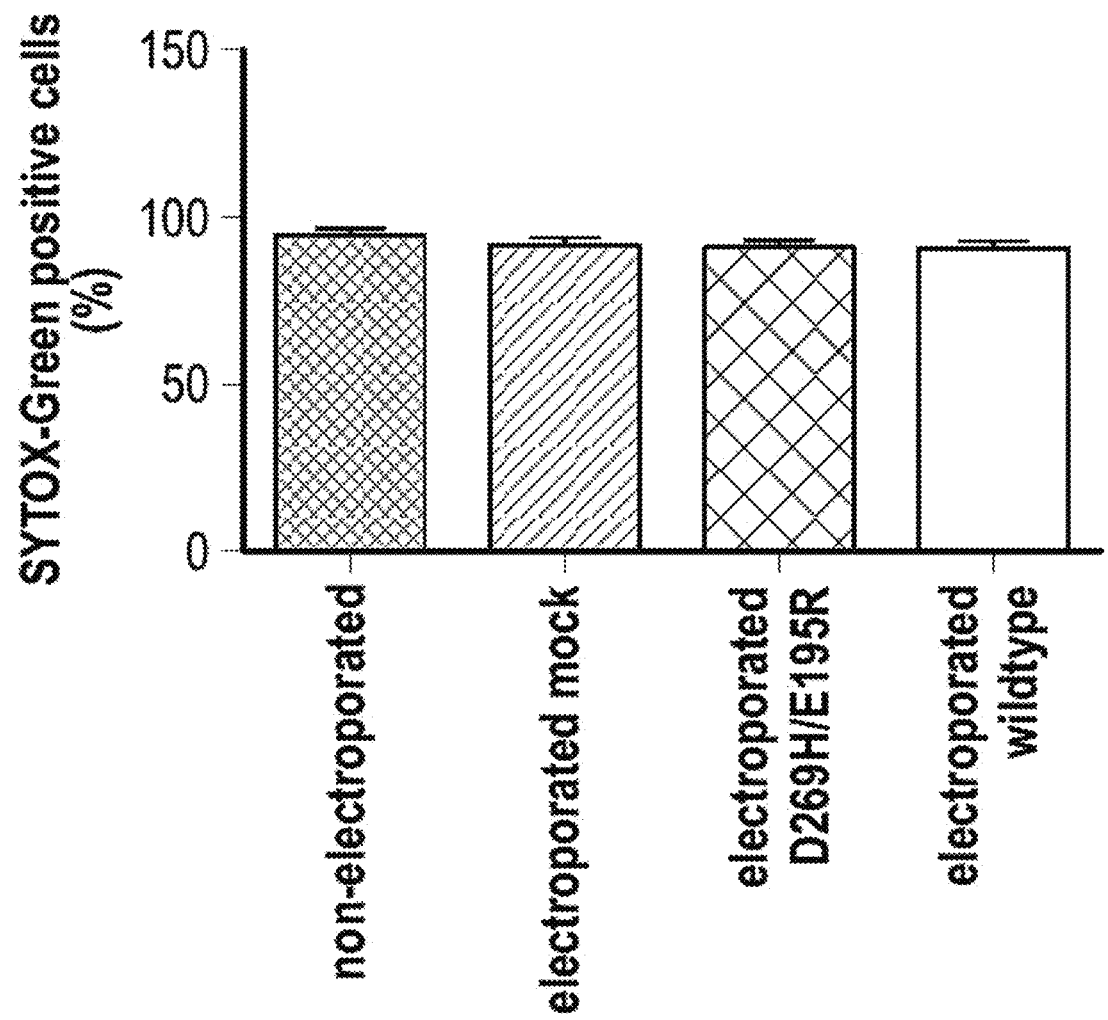
FIG. 15 illustrates viability of KHYG-1 cells transfected with wildtype or variant TRAIL.
Figure 16:
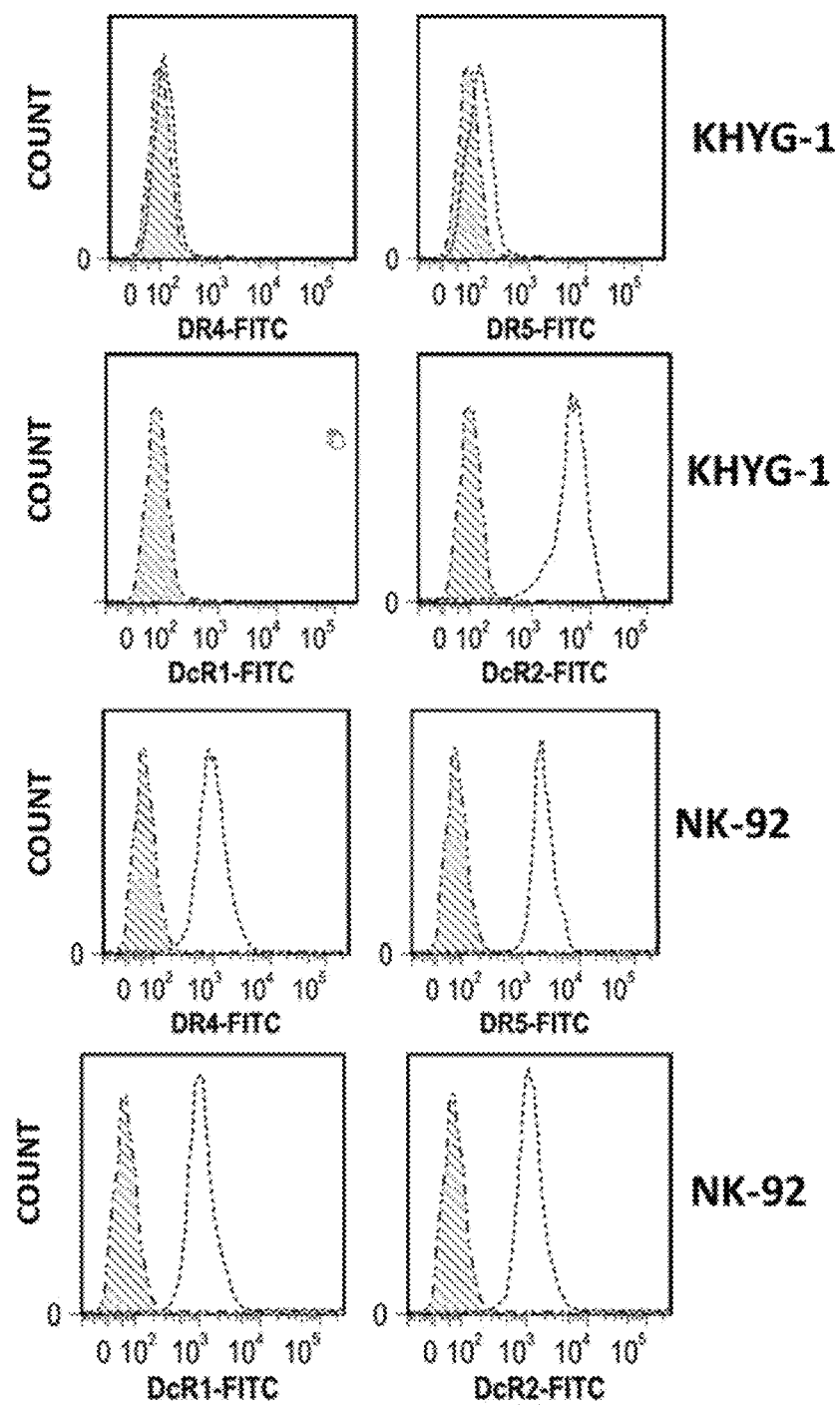
FIG. 16 illustrates expression of TRAIL receptors on the different NK cell lines; KHYG1(top four) and NK-92 (bottom four).

FIG. 15 provides evidence of KHYG-1 cell viability before and after transfection via electroporation. It can be seen that no statistically significant differences in cell viability are observed following transfection of the cells with TRAIL/TRAIL variant, confirming that the expression of wildtype or variant TRAIL is not toxic to the cells. This observation contradicts corresponding findings in NK-92 cells, which suggest the TRAIL variant gene knock-in is toxic to the cells (data not shown). Nevertheless, this is likely explained by the relatively high expression levels of TRAIL receptors DR4 and DR5 on the NK-92 cell surface (see FIG. 16).

Effects of TRAIL/TRAIL Variant on KHYG-1 Cell Cytotoxicity

Mouse anti-human CD2-APC antibody (BD Pharmingen catalog number: 560642) was used. Annexin V-FITC antibody (ImmunoTools catalog number: 31490013) was used. DNA dye SYTOX-Green (Life Technologies catalog number: 57020) was used. A 24-well cell culture plate (SARSTEDT AG catalog number: 83.3922) was used. Myelogenous leukemia cell line K562, multiple myeloma cell line RPMI8226 and MM1.S were used as target cells. K562, RPMI8226, MM1.S were cultured in RPMI 1640 medium containing 10% FBS, 2 mM L-glutamine and penicillin (100 U/mL)/streptomycin (100 mg/mL). As explained above, KHYG-1 cells were transfected with TRAIL/TRAIL variant. The target cells were washed and pelleted via centrifugation at 1500 rpm for 5 minutes. Transfected KHYG-1 cells were diluted to $0.5\times10^6$/mL. The target cell density was then adjusted in pre-warmed RPMI 1640 medium, in order to produce effector: target (E:T) ratios of 1:1. 0.5 mL KHYG-1 cells and 0.5 mL target cells were then mixed in a 24-well culture plate and placed in a humidified 37° C./5% $CO_2$ incubator for 12 hours. Flow cytometric analysis was then used to assay KHYG-1 cell cytotoxicity; co-cultured cells (at different time points) were washed and then stained with CD2-APC antibody (5 µL/test), Annexin V-FITC (5 µL/test) and SYTOX-Green (5 µL/test) using Annexin V binding buffer. Data were further analyzed using FlowJo 7.6.2 software. CD2-positive and CD2-negative gates were set, which represent KHYG-1 cell and target cell populations, respectively. The Annexin V-FITC and SYTOX-Green positive cells in the CD2-negative population were then analyzed for TRAIL-induced apoptosis.

Figure 17:
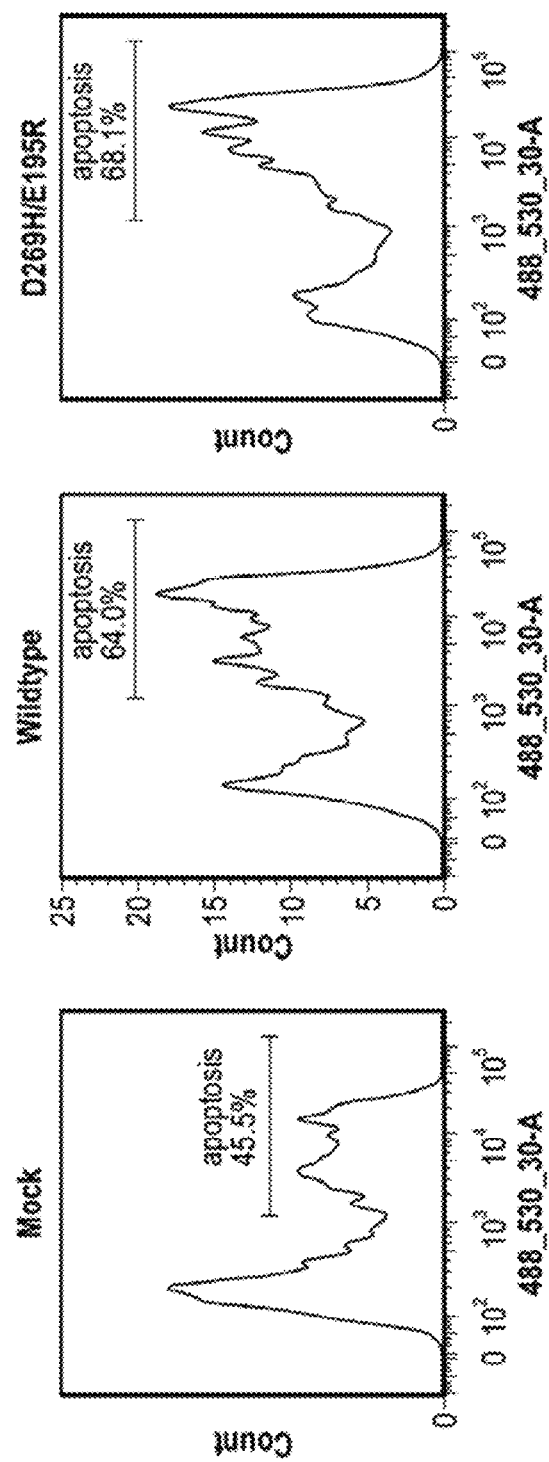
FIG. 17 illustrates the effect that KHYG-1 cells expressing wildtype TRAIL or variant TRAIL have on apoptosis of K562 cells.
Figure 18:
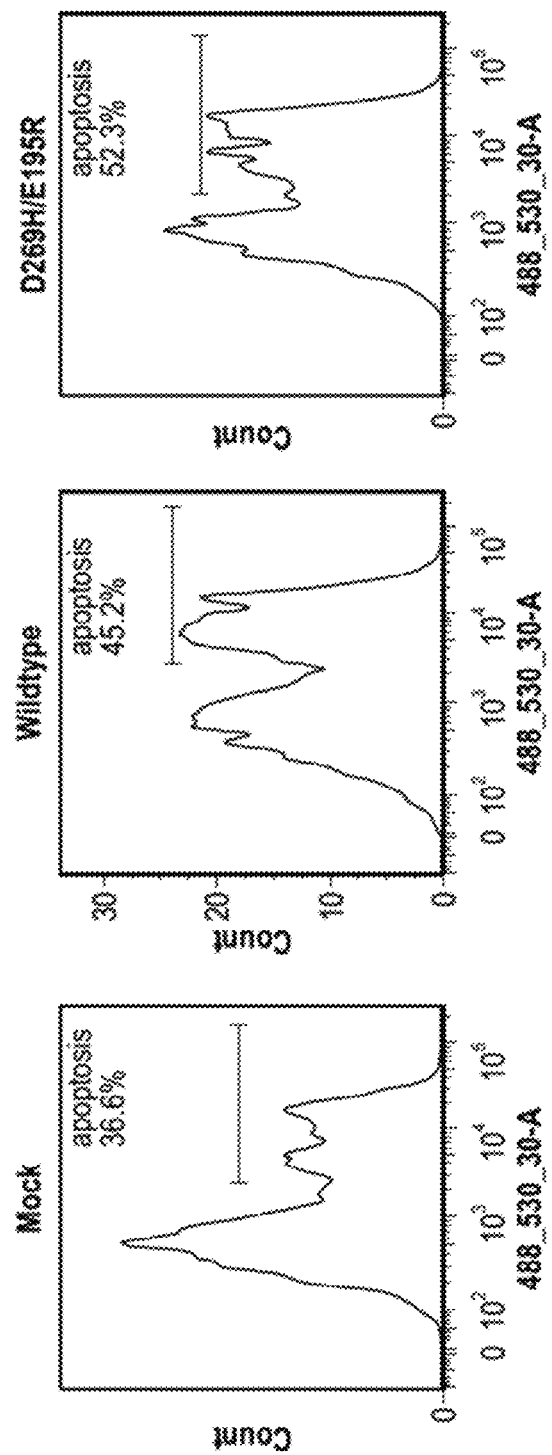
FIG. 18 illustrates the effect that KHYG-1 cells expressing wildtype TRAIL or variant TRAIL have on apoptosis of RPMI8226 cells.
Figure 19:
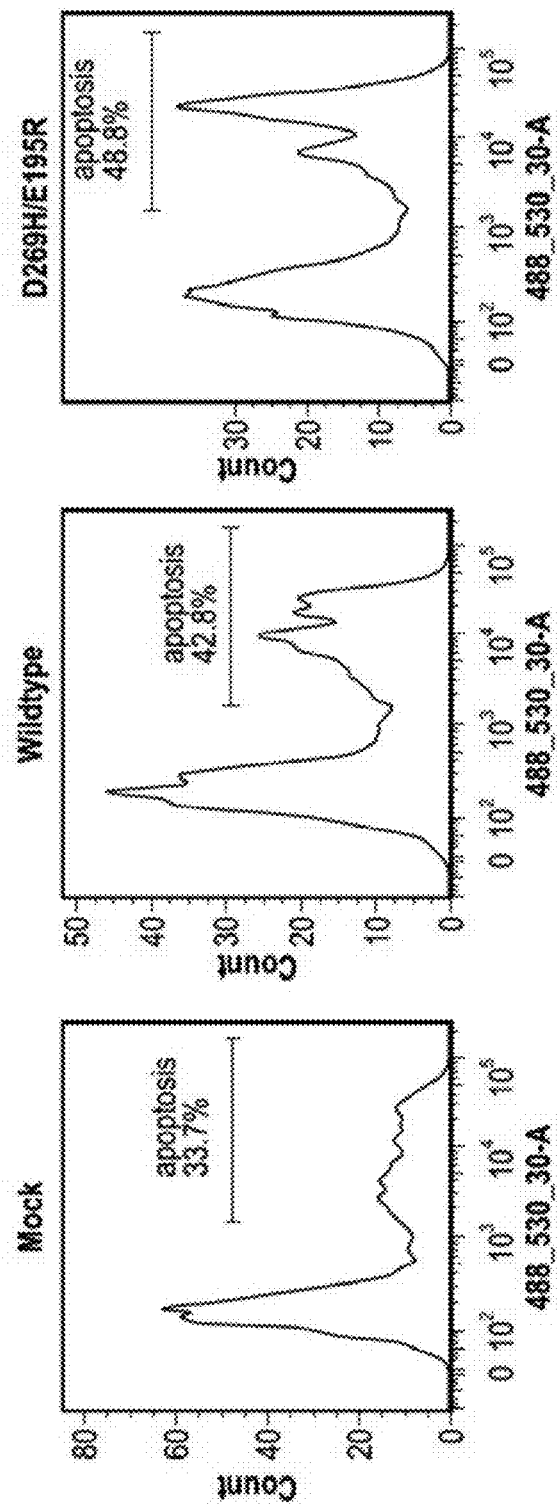
FIG. 19 illustrates the effect that KHYG-1 cells expressing wildtype TRAIL or variant TRAIL have on apoptosis of MML1.S cells.

FIGS. 17, 18 and 19 show the effects of both KHYG-1 cells expressing TRAIL or TRAIL variant on apoptosis for the three target cell lines: K562 (FIG. 17), RPMI8226 (FIG. 18) and MM1.S (FIG. 19). It is apparent for all target cell populations that TRAIL expression on KHYG-1 cells increased the level of apoptosis, when compared to normal KHYG-1 cells (not transfected with TRAIL). Moreover, TRAIL variant expression on KHYG-1 cells further increased apoptosis in all target cell lines, when compared to KHYG-1 cells transfected with wildtype TRAIL.

Cells of the invention, expressing the TRAIL variant, offer a significant advantage in cancer therapy, due to exhibiting higher affinities for the death receptor DR5. When challenged by these cells of the invention, cancer cells are prevented from developing defensive strategies to circumvent death via a certain pathway. Thus cancers cannot effectively circumvent TRAIL-induced cell death by upregulating TRAIL decoy receptors, as cells of the invention are modified so that they remain cytotoxic in those circumstances.

Example 13—Protocol for Blood Cancer Therapy Using NK Cells with TRAIL Variants Knocked-in KHYG-1 cells were transfected with TRAIL variant, as described above in Example 6. The following protocol was developed for use in treating patients with blood cancer:

Following diagnosis of a patient with a cancer suitably treated with the invention, a DR5-inducing agent, e.g. Bortezomib, is administered, prior to administration of the modified NK cells, and hence is used at low doses to upregulate expression of DR5 on the cancer, making modified NK cell therapy more effective. An aliquot of modified NK cells is then thawed, cultured and administered to the patient. Since the TRAIL variant expressed by the NK cells used in therapy has a lower affinity for decoy receptors than wildtype TRAIL, there is increased binding of death receptors on the cancer cell surface, and hence more cancer cell apoptosis as a result. Another option, prior to implementation of the above protocol, is to biopsy the cancer and culture cancer cells ex vivo. This step can be used to identify those cancers expressing particularly high levels of decoy receptors, and/or low levels of death receptors, in order to help determine whether a DR5-inducing agent is appropriate for a given patient. This step may also be carried out during therapy with the above protocol, as a given cancer might be capable of adapting to e.g. reduce its expression of DR5, and hence it may become suitable to treat with a DR5-inducing agent part-way through therapy.

Figure 20:
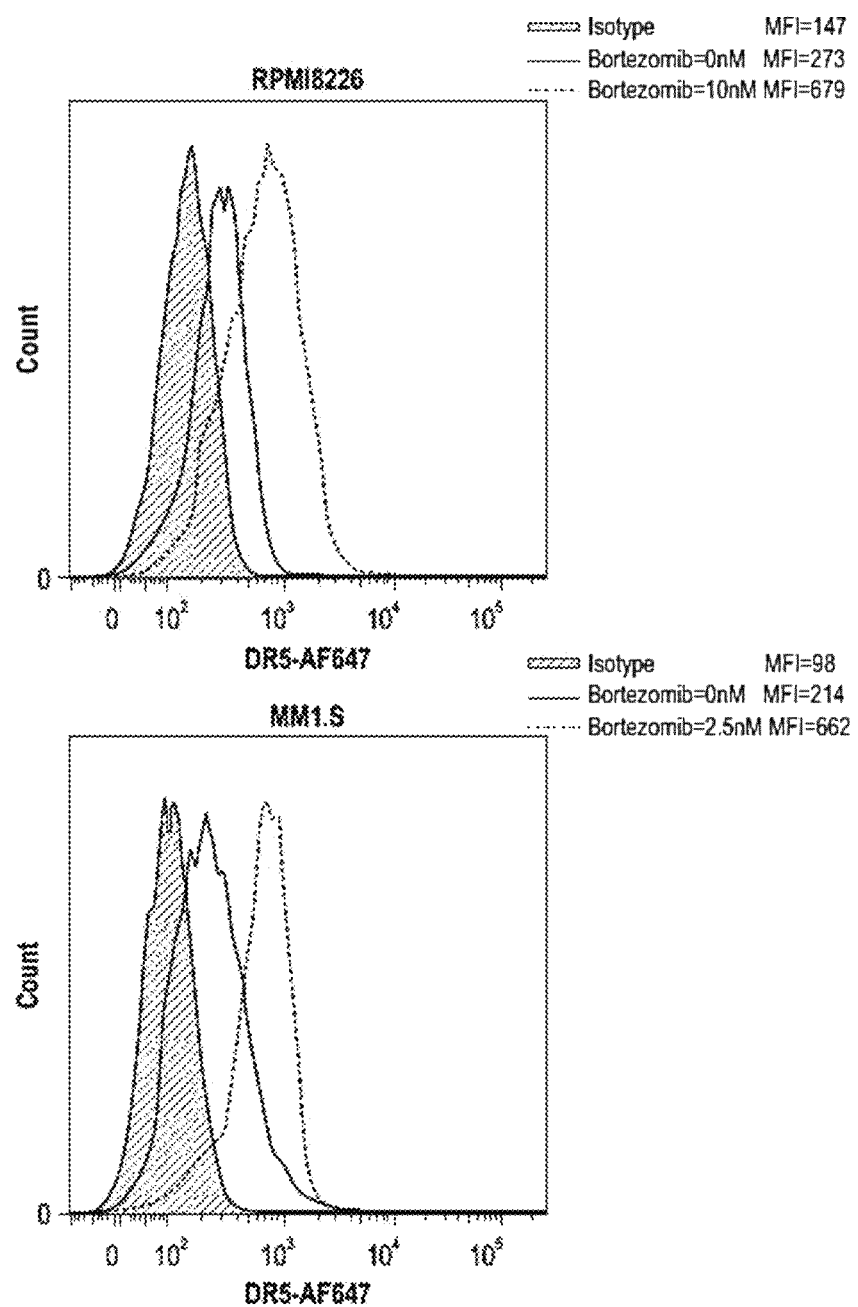
FIG. 20 illustrates FACS plots of DR5 expression on RPMI8226 cells and MM1.S cells, respectively, wherein the effects of Bortezomib treatment on DR5 expression are shown.
Figure 21:
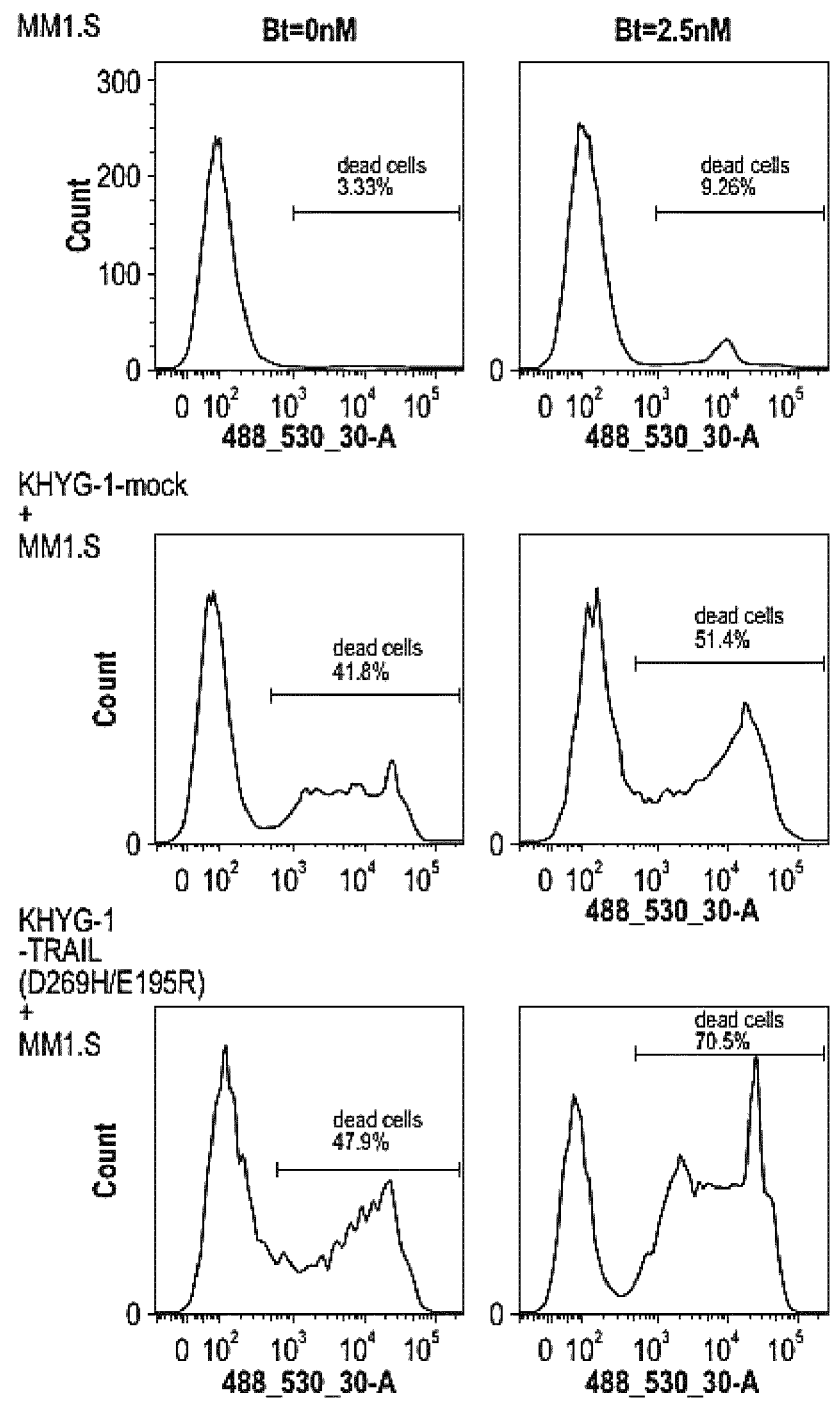
FIG. 21 illustrates two FACS plots of apoptosis in Bortezomib-pretreated/untreated MM1.S cells co-cultured with KHYG-1 cells with (bottom two) or without (middle two) a TRAIL variant.

Example 14-Effect of Proteasome Inhibition on NK Cell TRAIL Mediated Cytotoxicity Bortezomib (Bt) is a proteasome inhibitor (chemotherapy-like drug) useful in the treatment of Multiple Myeloma Bortezomib is known to upregulate DR5 expression on several different types of cancer cells, including MM cells. KHYG-1 cells were transfected with TRAIL variant, as described above in Example 12, before being used to target MM cells with or without exposure to Bortezomib.
Bortezomib-Induced DR5 Expression Bortezomib was bought from Millennium Pharmaceuticals. Mouse anti-human DR5-AF647 (catalog number: 565498) was bought from BD Pharmingen. The stained cell samples were analyzed on BD FACS Canto II. The protocol involved: (1) MM cell lines RPMI8226 and MM1.S were grown in RPMI1640 medium (Sigma, St Louis, Mo., USA) supplemented with 2 mM L-glutamine, 10 mM HEPES, 24 mM sodium bicarbonate, 0.01% of antibiotics and 10% fetal bovine serum (Sigma, St Louis, Mo., USA), in 5% CO2 atmosphere at 37° C. (2) MM cells were seeded in 6-well plates at $1\times10^6$/mL, 2 mL/well. (3) MM cells were then treated with different doses of Bortezomib for 24 hours. (4) DR5 expression in Bortezomib treated/untreated MM cells was then analyzed by flow cytometry (FIG. 20). As shown in FIG. 20 low dose Bortezomib treatment was found to increase DR5 expression in both MM cell lines: in RPMI 8226 cells (top) from a MFI of 273 to 679 with 10 nm Bortezomib; in MM1.S cells (bottom) from an MFI of 214 to 662 with 2.5 nm of Bortezomib. DR5 upregulation was associated with a minor induction of apoptosis (data not shown). It was found, however, that DR5 expression could not be upregulated by high doses of Bortezomib, due to high toxicity resulting in most of the MM cells dying.
Bortezomib-Induced Sensitization of Cancer Cells KHYG-1 cells were transfected with the TRAIL variant (TRAIL D269H/E195R), as described above in Example 12. The protocol involved the following steps (1) Bortezomib treated/untreated MM1.S cells were used as target cells. MM1.S cells were treated with 2.5 nM of Bortezomib (right column) or vehicle (left column) for 24 hours. (2) 6 hours after electroporation of TRAIL variant mRNA, KHYG-1 cells were then cultured with MM cells in 12-well plate. After washing, cell concentrations were adjusted to $1\times10^6$/mL, before mixing KHYG-1 and MM1.S cells at 1:1 ratio to culture for 12 hours. (3) Flow cytometric analysis of the cytotoxicity of KHYG-1 cells was carried out. The co-cultured cells were collected, washed and then stained with CD2-APC antibody (5 uL/test), AnnexinV-FITC (5 uL/test) and SYTOX-Green (5 uL/test) using AnnexinV binding buffer. (4) Data were further analyzed using FlowJo 7.6.2 software. CD2-negative population represents MM1.S cells. KHYG-1 cells are strongly positive for CD2. Finally, the AnnexinV-FITC and SYTOX-Green positive cells in the CD2-negative population were analyzed. Flow cytometric analysis of apoptosis was performed in Bortezomib-pretreated/untreated MM1.S cells co-cultured with KHYG-1 cells electroporated with/without TRAIL variant. As shown in FIG. 21 it was found that Bortezomib induced sensitivity of MM cells to KHYG-1 cells expressing the TRAIL variant (47.9% killing to 70.5% killing) to a much greater extent than to cells expressing wildtype TRAIL (41.8% killing to 51.4% killing). The data therefore indicated that an agent that induced DR5 expression was effective in the model in increasing cytotoxicity against cancer cells, and hence may be useful in enhancing the cancer therapy of the present invention.

Example 15—Generation of CAR Constructs

Variable heavy- and light-chain coding regions were cloned in the pcDNA3.3 (Invitrogen) based vectors p33G1f and p33Kappa, respectively. All low affinity antibodies were produced under serum-free conditions by individually co-transfecting heavy chains (SEQ ID No 1) from the high affinity CD38 antibodies (described in WO2011154453 and WO2006099875) and light chains from random germline light-chain expression vectors in HEK293F cells using 293fectin (Invitrogen), as previously described (Vink et al. 2014). Cell-free supernatants were harvested and antibody concentrations were determined by Octet IgG quantification (Forte Bio). This light chain exchange results in antibodies (in this case scFvs) having reduced affinity for CD38 compared with Daratumumab.

Affinities were measured and ranked using biolayer interferometry on an Octet HTX instrument (ForteBio). Anti-human IgG Fc Capture biosensors (ForteBio) were loaded for 1,000 s with human IgG type 1 (hIgG1) containing different heavy- and light-chain combinations directed against CD38. After a baseline (100 s), the association (1,000 s) and dissociation (1,000 s) of the extracellular domain of N-terminally His-tagged CD38 (His-CD38, 100 nM) in Sample Diluent (ForteBio) was determined. For calculations, the theoretical molecular mass of His-CD38 based on the amino acid sequence was used, i.e., 30.5 kDa. Experiments were carried out while shaking at 1,000 rpm and 30° C. Data were analyzed with Data Analysis software v8.0 (ForteBio) using the 1:1 model and a local full fit, with 1,000 s of association time and 250 s of dissociation time. Data traces were corrected by subtraction of the average of four reference biosensors loaded with IgG1-3003-028 WT and incubated with sample diluent only. The y axis was aligned to the last 5 s of the baseline, and interstep correction as well as Savitzky-Golay filtering was applied.

Homogeneous binding assays for human CD38 specific antibodies were performed in 1,536-well microtiter plates in dose response using a Tecan Evo 200 liquid handler. Binding of IgG1 antibodies to CHO cells transiently expressing human CD38, CHO wt background control, and streptavidin beads coated with purified biotinylated histagged human CD38 was detected with a secondary polyclonal goat IgG anti-human IgG (Fc)-Alexa Fluor 647 conjugate (Jackson ImmunoResearch). In parallel, the binding of IgG1 antibodies to streptavidin beads coated with purified biotinylated his-tagged human CD38 was also assessed using a monovalent secondary goat Fab anti-human IgG (H+L)-DyLight 649 conjugate (Jackson ImmunoResearch). IgG1 samples were normalized and diluted in Freestyle 293 expression medium (GIBCO). 2 mL of diluted sample was added to 5 mL of cell or bead suspensions containing secondary conjugates at 200 ng/mL IgG conjugate or 300 ng/mL Fab conjugate, respectively. Cell suspensions were prepared in FMAT buffer (PBS, 0.1% BSA, and 0.02% sodium azide)+ 0.075% Pluronic F-68. Bead suspensions were prepared in HBB (10 mM HEPES [pH 7.4], 150 mM NaCl, 5 mM KCl, 1 mM MgCl2, 1.8 mM CaCl2, 0.5% BSA, and 0.01% sodium azide+0.075% Pluronic F-68). After 8 hr of incubation at room temperature (RT) in the dark, fluorescence signals were recorded using the Applied Biosystems 8200 Cellular Detection System (ThermoFisher Scientific), with a 50-count cut-off value applied. Obtained total fluorescence intensity data were processed and visualized using ActivityBase software (IDBS).

The selected variable light chain B1 (SEQ ID NO: 23) and variable heavy chain (SEQ ID NO: 1) were amplified using PCR with primers (SEQ ID NOs: 8-22) containing homology arms, and Gibson assembly (NEB) was used to combine both chains linked with a G4S linker. The generated scFvs were cloned into an SFG retroviral vector, followed by a CD8a transmembrane domain and one of the below-mentioned co-stimulatory domains, as described for T cells in Zhao et al. (2015). The CAR constructs were linked by a 2A sequence to a truncated NGFR or dsRed sequence (Kim et al. 2011).

Example 16—Generation of Retroviral Particles

Phoenix-Ampho packaging cells were transfected with the CAR constructs, gag-pol (pHIT60), and envelope (pCOLT-GALV) vectors (Roche). 2 and 3 days after transfection, cell-free supernatants containing retroviral particles were collected and directly used for transduction.

KHYG-1 cells were retrovirally transduced using spinoculation on retronectin (Takara) coated plates. A second transduction was done after 16 hr. 72 hr post-transduction, CD38 expression was determined by flow cytometry. The transduced KHYG-1 cells were cultured. 1 week later, CAR-transduced NK cells were either stimulated with irradiated (5 Gy) UM9 cells (effector to target [E:T] ratio 1:3) or tested functionally.

Example 17-Primary Cells from MM Patients and Healthy Individuals

BM-mononuclear cells (MNCs) containing 5%-40% malignant plasma cells were isolated from BM aspirates of MM patients through Ficoll-Paque density centrifugation and either used directly or cryo-preserved in liquid nitrogen until use. PBMCs/MNCs were isolated from Buffy coats of healthy blood-bank donors by Ficoll-Paque density centrifugation. All primary samples were obtained after informed consent and approval by the medical ethical committee.

Example 18—Enhanced Cytotoxicity of CD38-CAR-Expressing NK Cells

KHYG-1 cells with and without a low-affinity chimeric antigen receptor for CD38 (CD38-CAR) were co-cultured with UM9 cells at different effector:target (E:T) ratios. Three variants of the CD38-CAR KHYG-1 cells were tested: BBz B1, 28z B1 and 28z BBL B1; these variants corresponding to co-stimulatory domains 41BB-CD3zeta, CD28-CD3zeta and CD28/4-1BB plus ligand, respectively (41BB=SEQ ID NO: 42; CD3zeta=SEQ ID NO: 41; and CD28=SEQ ID NO: 43).

Cytotoxicity was measured 4 hours after co-culture, using the DELFIA EuTDA Cytotoxicity Kit from PerkinElmer (Catalog number: AD0116). Target cells UM9 were cultivated in RPMI-1640 medium containing 10% FBS, 2 mM L-glutamine and antibiotics. 96-well V-bottom plates (catalog number: 83.3926) were bought from SARSTEDT. An Eppendorf centrifuge 5810R (with plate rotor) was used to spin down the plate. A VARIOSKAN FLASH (with ScanIt software 2.4.3) was used to measure the fluorescence signal produced by lysed UM9 cells. UM9 cells were washed with culture medium and the number of cells adjusted to $1\times10^6$ cells/mL with culture medium. 2-4 mL of cells was added to 5 µl of BATDA reagent and incubated for 10 minutes at 37° C. Within the cell, the ester bonds are hydrolyzed to form a hydrophilic ligand, which no longer passes through the membrane. The cells were centrifuged at 1500 rpm for 5 mins to wash the loaded UM9 cells. This was repeated 3-5 times with medium containing 1 mM Probenecid (Sigma P8761). After the final wash the cell pellet was re-suspended in culture medium and adjusted to about $5\times10^4$ cells/mL. Wells were set up for detection of background, spontaneous release and maximum release. 100 µL, of loaded target cells (5,000 cells) was transferred to wells in a V-bottom plate and 100 µL, of effector cells (KHYG-1 cells) was added at varying cell concentrations, in order to produce E:T ratios ranging from 0.5:1 to 2:1. The plate was centrifuged at 100×g for 1 minute and incubated for 4 hours in a humidified 5% CO2 atmosphere at 37° C. For maximum release wells 104, of lysis buffer was added to each well 15 minutes before harvesting the medium. The plate was centrifuged at 500×g for 5 minutes. 20 µl, of supernatant was transferred to a flat-bottom 96 well plate 200 µl, of pre-warmed Europium solution added. This was incubated at room temperature for 15 mins using a plate shaker. As UM9 cells are lysed by the KHYG-1 cells, they release ligand into the medium. This ligand then reacts with the Europium solution to form a fluorescent chelate that directly correlates with the amount of lysed cells. The fluorescence was then measured in a time-resolved fluorometer by using VARIOSKAN FLASH. The specific release was calculated using the following formula: % specific release=Experiment release−Spontaneous release/Maximum release−Spontaneous release. Statistical analysis was performed using Graphpad Prism 6.04 software. A paired t test was used to compare the difference between CD38-CAR KHYG-1 cells and control groups.

Bioluminescent Imaging-Based Cytotoxicity Assay

To determine the lysis of Luc-GFP-transduced human malignant cell lines by CD38 CAR NK cells 7-10 days after transduction, serial dilutions of mock or CD38-CAR NK cells were co-incubated with the malignant cell lines. The luciferase signal produced by surviving malignant cells was determined after 16-24 hr with a GloMax 96 Micro-plate Luminometer (Promega) within 15 min after the addition of 125 mg/mL beetle luciferin (Promega). % lysis cells=1 (bioluminescence imaging [BLI] signal in treated wells/BLI signal in untreated wells) 100%.

Figure 22:
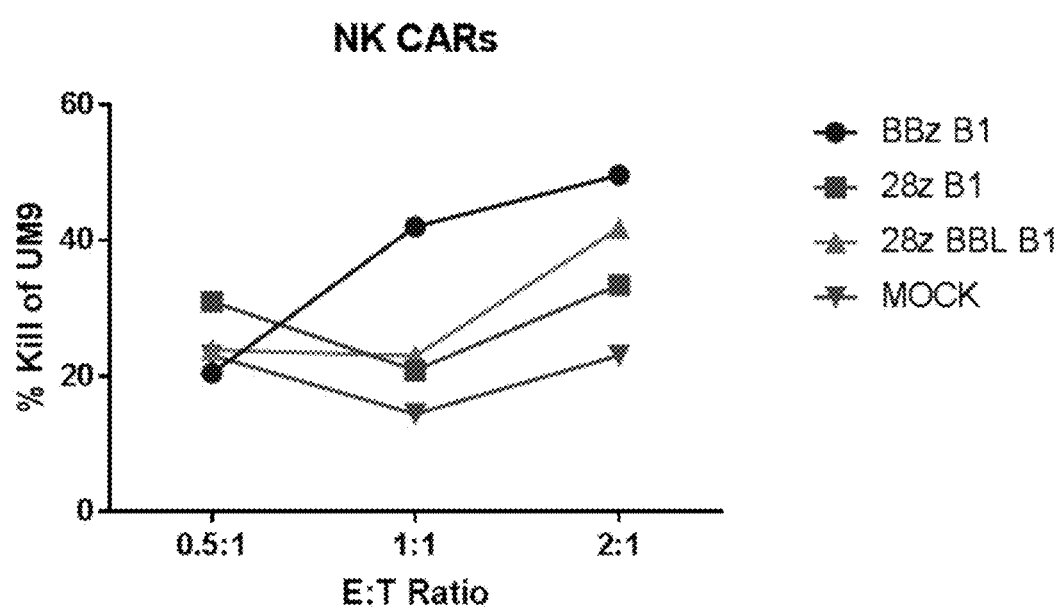
FIG. 22 shows the effect of treating multiple myeloma cell line UM9 with various low affinity CD38 NK CARs.

The specific release was found to be significantly increased in co-cultures containing the CD38-CAR KHYG-1 cells, despite only around 50% of the cells being successfully transduced. This was the case at all E:T ratios, except for the CD38-CAR KHYG-1 cells with the 41BB-CD3zeta co-stimulatory domain at an E:T ratio of 0.5:1 (see FIG. 22). More potent cytotoxic effects would be expected in higher purity samples of the effector cells carrying the CD38-CARs. As fluorescence directly correlates with cell lysis, it was confirmed that CD38-CAR expression in KHYG-1 cells resulted in an increase in their ability to kill UM9 cancer target cells.

Flow Cytometry Based Cytotoxicity Assay 7-10 days after transduction, serial dilutions of CD38-CAR-KHYG-1 cells were incubated with Violet tracer (Thermo Fisher) labeled BM-MNC or PBMC for 14 hr. After addition of flow-count fluorospheres (Beckman 7547053), cells were harvested and stained for CD38 and/or CD138. Viable cells were then quantitatively analyzed through flow-count-equalized measurements. Percentage cell lysis was calculated as follows and only if the analyzed target cell population contained >500 viable cells in the untreated samples: % lysis cells=1 (absolute number of viable target cells in treated wells/absolute number of viable target cells in untreated wells) 100%.

Figure 23:
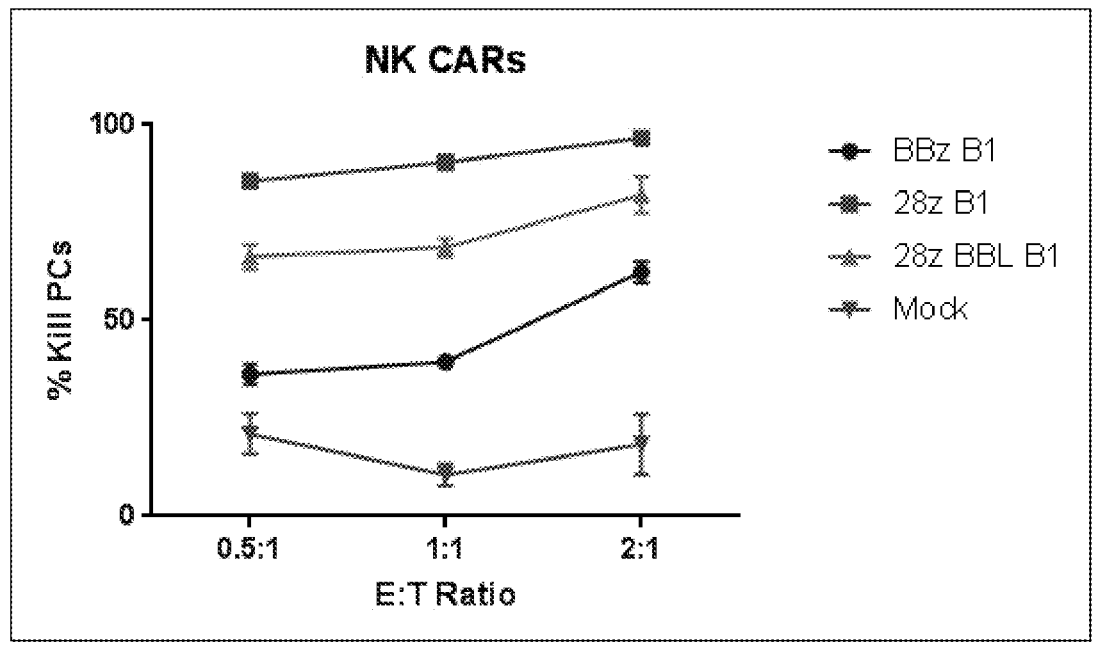
FIGS. 23 and 24 show the effect of treating primary multiple myeloma cells with various low affinity CD38 NK CARs.
Figure 24:
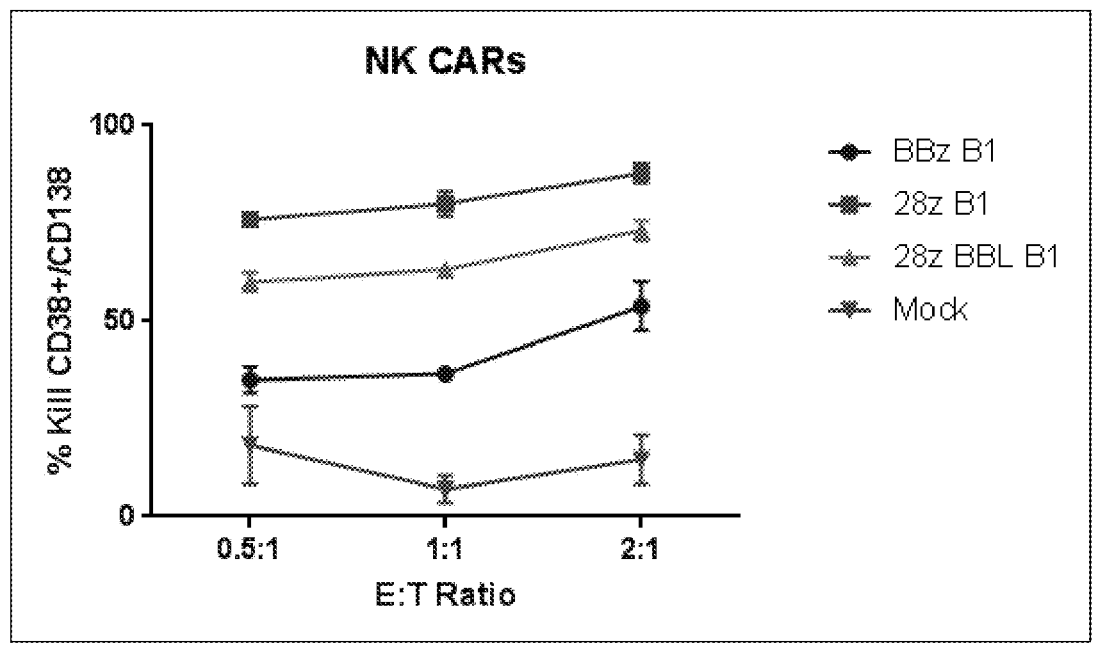
Figure 25:
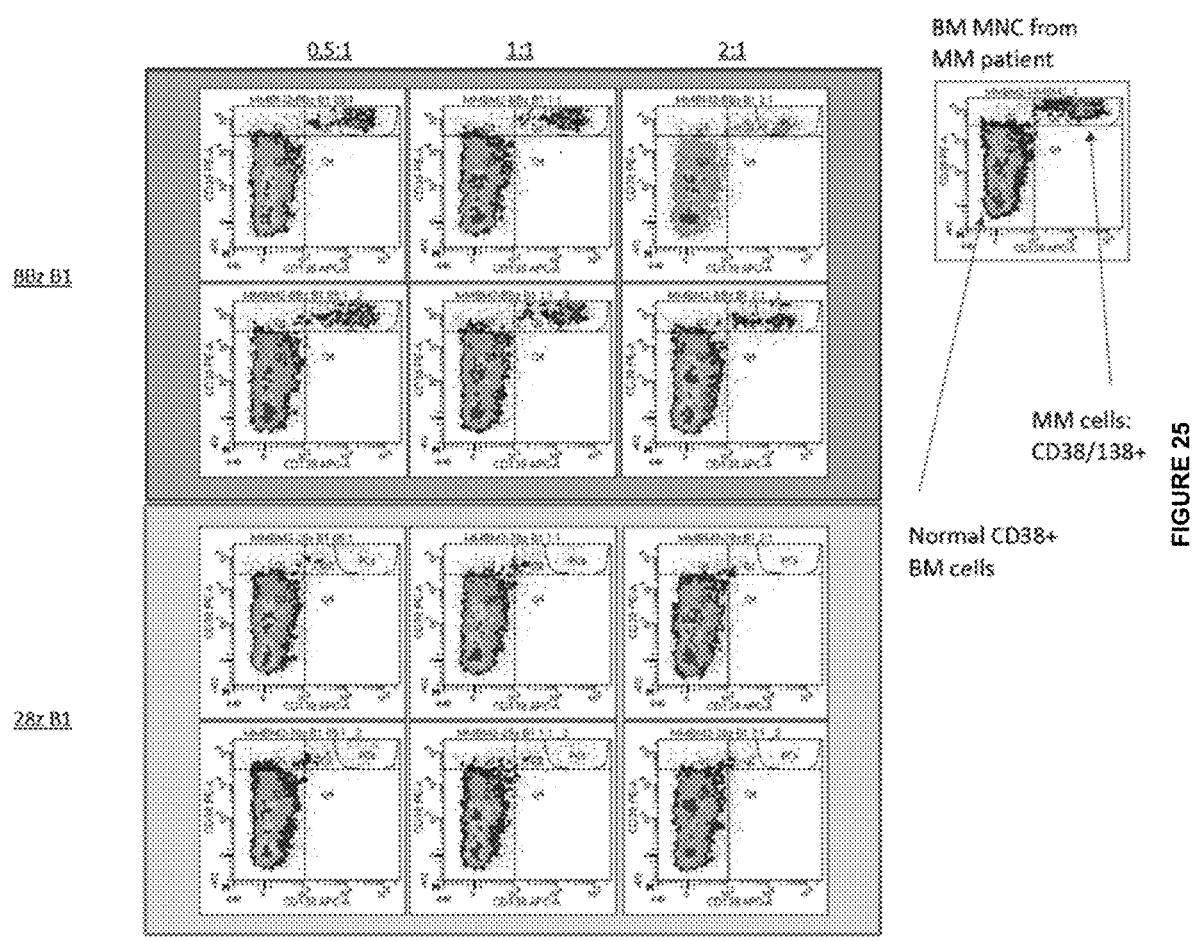
FIGS. 25 and 26 show cell subsets FACS gated according to their expression of CD38 and CD138, indicating that the low affinity CD38 CARs effectively target cancerous cells but not non-cancerous cells.
Figure 26:
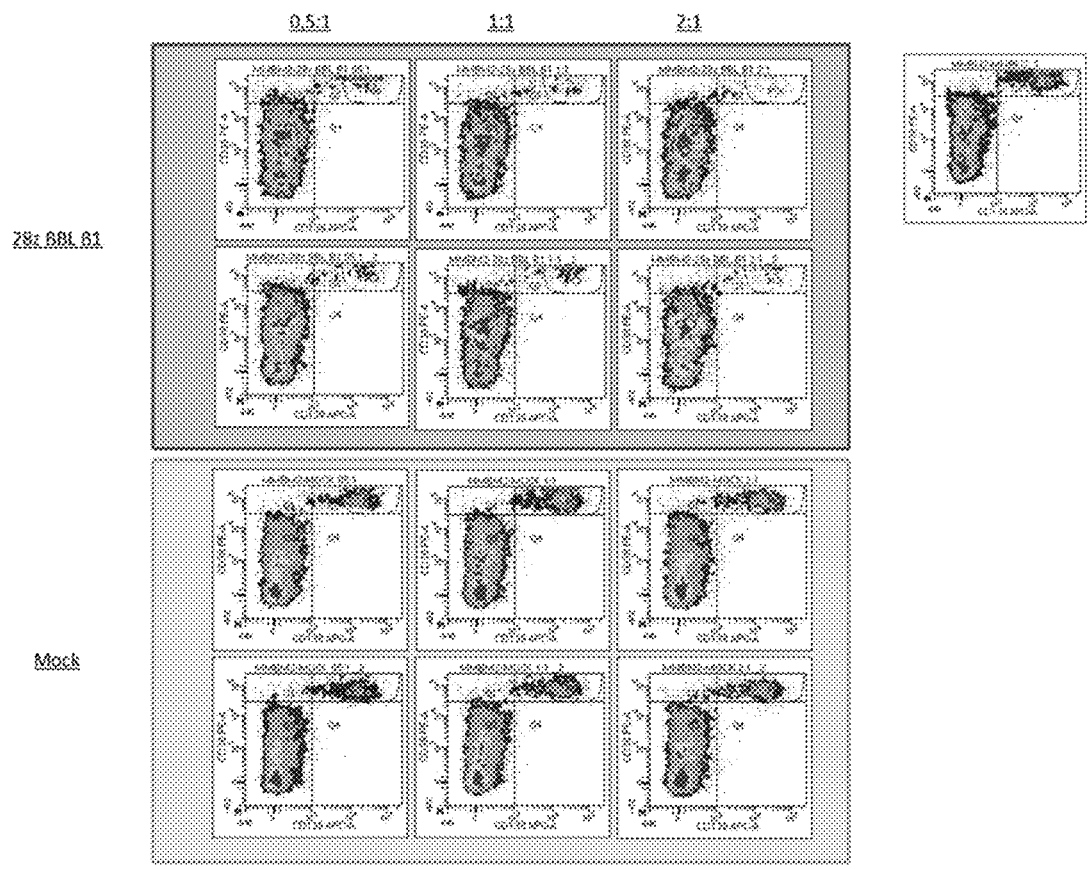

Two types of gates were used to analyse the primary MM cells: Very bright CD138+/CD38+ cells vs all CD138+/CD38 cells (see FIGS. 25 and 26). There was minimal non-significant difference in the results between subsets. Primary MM cells were susceptible to CD38-CAR-KHYG-1-induced cell death. As seen in FIGS. 23 and 24, the most significant killing of primary MM cells was observed when using CARs containing CD28-CD3 zeta (28z B1). Minimal or no killing of CD38+/CD138− cells (normal non-malignant CD38-expressing cells) was observed (see FIGS. 25 and 26)—hence the cells did not appear to be targeted by the CAR-NK cells.

Thus, it has been shown that the 'low affinity' CD38 CAR-NK cells have an ability to target and kill CD38-expressing cancer cells without causing adverse on-target off-cancer effects in normal non-malignant cells expressing CD38.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Sequence IDS

| SEQ ID NO | Amino Acid or DNA Sequence |
|---|---|
| 1 | QVQLVQSGAEVKKPGSSVKVSCKAFGGTFSSYAISWVRQAPGQGLEWMGRIIRFLGIANYAQKFQGRVTLIADKSTNTAYMELSSLRSEDTAVYYCAGEPGRERDPDAVDIWGQGTMVTVSS |
| 2 | DIQMTQSPSSLSASVGDRVTITCRASQGIRSWLAWYQQKPEKAPKSLIYAASSLQSGVPSRFSGSGSGTDFTLTISSLQPEDFATYYCQQYNSYPLTFGGGTKVEIK |
| 3 | QVQLVQSGAEVKKPGSSVKVSCKPSGGTFRSYAISWVRQAPGQGLEWMGRIIVFLGKVNYAQRFQGRVTLTADKSTTTAYMELSSLRSEDTAVYYCTGEPGARDPDAFDIWGQGTMVTVSS |
| 4 | DIQMTQSPSSLSASVGDRVTITCRASQGIRSWLAWYQQKPEKAPKSLIYAASSLQSGVPSRFSGSGSGTDFTLTISSLQPEDFATYYCQQYNNYPLTFGGGTKVEIK |
| 5 | QVQLVQSGAEVKKPGSSVKVSCKAFGGTFSSYAISWVRQAPGQGLEWMGRIIRFLGKTNHAQKFQGRVTLTADKSTNTAYMELSSLRSEDTAVYYCAGEPGDRDPDAVDIWGQGTMVTVSS |
| 6 | DIQMTQSPSSLSASVGDRVTITCRASQGIRSWLAWYQQKPEKAPKSLIYAASSLQSGVPSRFSGSGSGTDFTLTISSLQPEDFATYYCQQYNSYPLTFGGGTKVEIK |
| 7 | EVQLVQSGAEVKKPGESLKISCKGSGYSFSNYWIGWVRQMPGKGLEWMGIIYPHDSDARYSPSFQGQVTFSADKSISTAYLQWSSLKASDTAMYYCARHVGWGSRYWYFDLWGRGTLVTVSS |
| 8 | CTGCTGCTGCATGCGGCGCGCCCGGACATCCAGATGACCCAGAGC |
| 9 | CTGCTGCTGCATGCGGCGCGCCCGGACATCCAGCTGACCCAGAGC |
| 10 | CTGCTGCTGCATGCGGCGCGCCCGGCCATCCAGCTGACCCAGAGC |
| 11 | CTGCTGCTGCATGCGGCGCGCCCGGTGATCTGGATGACCCAGAGC |
| 12 | CTGCTGCTGCATGCGGCGCGCCCGGAGATCGTGCTGACCCAGAGC |
| 13 | CTGCTGCTGCATGCGGCGCGCCCGGAGATCGTGATGACCCAGAGC |
| 14 | CTGCTGCTGCATGCGGCGCGCCCGGACATCGTGATGACCCAGAGC |
| 15 | GCGGCGGAGGATCTGGGGGAGGCGGCTCTCAGGTGCAGCTGGTGCAGAGCG |
| 16 | GCGGCGGAGGATCTGGGGGAGGCGGCTCTGAAGTGCAGCTGGTGCAGTCTGG |
| 17 | CAGATCCTCCGCCGCCAGATCCGCCTCCGCCCTTGATCTCCACCTTGGTGCC |
| 18 | CAGATCCTCCGCCGCCAGATCCGCCTCCGCCCTTGATTTCCAGCTTGGTGCC |
| 19 | CAGATCCTCCGCCGCCAGATCCGCCTCCGCCCTTGATGTCCACCTTGGTGCC |
| 20 | CAGATCCTCCGCCGCCAGATCCGCCTCCGCCCTTGATTTCCAGCCGGGTGCC |
| 21 | GGGGCGGGTGTAGGCGGCCGCGGAGCTGGTGTTGTTGTGCTGGACACGGTGACCATTGTG |
| 22 | GGGGCGGGTGTAGGCGGCCGCGGAGCTGGTGTTGTTGTGCTAGACACGGTCACGAGGGTG |
| 23 | EIVLTQSPDFQSVTPKEKVTITCRASQSIGSSLHWYQQKPDQSPKLLIKYASQSFSGVPSRFSGSGSGTDFTLTINSLEAEDAATYYCHQSSSLPYTFGQGTKLEIK |
| 24 | GAGTCACAGGTGGCATTTGGCGG |
| 25 | CGAATCGCAGGTGGTCGCACAGG |
| 26 | CACTCACCTTTGCAGAAGACAGG |
| 27 | CCTTGTGCCGCTGAAATCCAAGG |

| SEQ ID NO | Amino Acid or DNA Sequence |
|---|---|
| 28 | DIQMTQSPSSLSASVGDRVTITCRASQGISNYLAWFQQKPGKAPKSLIYAASSLQSGVPSRFSGSGSGTDFTLTISSLQPEDFATYYCQQYNSYPYTFGQGTKLEIK |
| 29 | FGGTFSSYAI |
| 30 | IIRFLGIANY |
| 31 | CAGEPGERDPDAVDIW |
| 32 | SGYSFSNYWI |
| 33 | IIYPHDSDARY |
| 34 | CARHVGWGSRYWYFDL |
| 35 | QSIGSSL |
| 36 | LIKYASQSF |
| 37 | HQSSSLPYTF |
| 38 | QGISNYL |
| 39 | LIYAASSLQ |
| 40 | QQYNSYPYTF |
| 41 | MKWKALFTAAILQAQLPITEAQSFGLLDPKLCYLLDGILFIYGVILTALFLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| 42 | MGNSCYNIVATLLLVLNFERTRSLQDPCSNCPAGTFCDNNRNQICSPCPPNSFSSAGGQRTCDICRQCKGVFRTRKECSSTSNAECDCTPGFHCLGAGCSMCEQDCKQGQELTKKGCKDCCFGTFNDQKRGICRPWTNCSLDGKSVLVNGTKERDVVCGPSPADLSPGASSVTPPAPAREPGHSPQIISFFLALTSTALLFLLFFLTLRFSVVKRGRKKLLYIFKQPFMRPVQTTQEEDGCSCRFPEEEGGCEL |
| 43 | MLRLLLALNLFPSIQVTGNKILVKQSPMLVAYDNAVNLSCKYSYNLFSREFRASLHKGLDSAVEVCVVYGNYSQQLVYSKTGFNCDGKLGNESVTFYLQNLYVNQTDIYFCKIEVMYPPPYLDNEKSNGTIIHVKGKHLCPSPLFPGSKPFWVLVVVGGVLACYSLLVTVAFIIFWVRSKRSRLLHSDYMNMTPRRPGPTRKHYQPYAPPRDFAAYRS |

What is claimed is:

1. A method of treating multiple myeloma (MM) in a mammal, the method comprising administering to the mammal a natural killer (NK) cell modified to express a chimeric antigen receptor (CAR) for CD38, wherein the administering kills MM cells expressing CD38, wherein the CD38 CAR comprises (a) a heavy chain variable region comprising SEQ ID NO: 1 or SEQ ID NO: 7, and (b) a light chain variable region comprising SEQ ID NO: 23 or SEQ ID NO: 28.

2. The method according to claim 1, wherein the NK cell expresses E-selectin ligand.

3. The method according to claim 1, wherein the NK cell binds the HECA-452 antibody.

4. The method according to claim 1, wherein the NK cell is a KHYG-1 cell.

5. The method according to claim 1, wherein the CD38 CAR comprises one or more or all of the heavy chain CDRs in SEQ ID NO:s 29, 30 and 31.

6. The method according to claim 1, wherein the CD38 CAR comprises one or more or all of the heavy chain CDRs in SEQ ID NO:s 32, 33 and 34.

7. The method according to claim 1, wherein the CD38 CAR comprises one or more or all of the light chain CDRs in SEQ ID NO:s 35, 36 and 37.

8. The method according to claim 1, wherein the CD38 CAR comprises one or more or all of the light chain CDRs in SEQ ID NO:s 38, 39 and 40.

9. The method according to claim 1, wherein the CD38 CAR comprises one or more co-stimulatory domains selected from SEQ ID NO: 41, SEQ ID NO: 42 and SEQ ID NO: 43.

10. The method according to claim 1, wherein the NK cell has been modified to express a TRAIL variant that has increased affinity for TRAIL death receptors, relative to wildtype TRAIL.

11. A method of treating multiple myeloma (MM) in a mammal, the method comprising administering to the mammal a natural killer (NK) cell modified to express a chimeric antigen receptor (CAR) for CD38, wherein the administration kills MM cells expressing CD38, and wherein the CD38 CAR comprises a heavy chain variable region comprising SEQ ID NO: 1 and a light chain variable region comprising SEQ ID NO: 23.

12. The method according to claim 1, wherein the CAR has an affinity for CD38 that is at least 25% lower than the affinity of Daratumumab for CD38.

\* \* \* \* \*